(12) United States Patent
Aharonov et al.

(10) Patent No.: US 8,802,599 B2
(45) Date of Patent: Aug. 12, 2014

(54) GENE EXPRESSION SIGNATURE FOR CLASSIFICATION OF TISSUE OF ORIGIN OF TUMOR SAMPLES

(75) Inventors: Ranit Aharonov, Tel Aviv (IL); Nitzan Rosenfeld, Omer (IL); Shai Rosenwald, Nes Ziona (IL)

(73) Assignee: Rosetta Genomics, Ltd., Rehovot (IL)

( * ) Notice: Subject to any disclaimer, the term of this patent is extended or adjusted under 35 U.S.C. 154(b) by 0 days.

(21) Appl. No.: 13/167,489

(22) Filed: Jun. 23, 2011

(65) Prior Publication Data

US 2011/0312530 A1 Dec. 22, 2011

Related U.S. Application Data

(63) Continuation-in-part of application No. PCT/IL2009/001212, filed on Dec. 23, 2009, and a continuation-in-part of application No. 12/532,940, filed as application No. PCT/IL2008/000396 on Mar. 20, 2008, now abandoned.

(60) Provisional application No. 61/140,642, filed on Dec. 24, 2008, provisional application No. 60/907,266, filed on Mar. 27, 2007, provisional application No. 60/929,244, filed on Jun. 19, 2007, provisional application No. 61/024,565, filed on Jan. 30, 2008.

(51) Int. Cl.
 *C12Q 1/68* (2006.01)
 *C40B 30/04* (2006.01)

(52) U.S. Cl.
 USPC ............ 506/9; 435/6.11; 435/6.12; 536/23.1; 536/24.3

(58) Field of Classification Search
 None
 See application file for complete search history.

(56) References Cited

U.S. PATENT DOCUMENTS

| | | | |
|---|---|---|---|
| 2003/0225526 A1 | 12/2003 | Golub et al. | |
| 2007/0065844 A1* | 3/2007 | Golub et al. | 435/6 |
| 2008/0269072 A1* | 10/2008 | Hart et al. | 506/16 |
| 2008/0306018 A1* | 12/2008 | Croce et al. | 514/44 |
| 2010/0286044 A1* | 11/2010 | Litman et al. | 514/9.7 |

FOREIGN PATENT DOCUMENTS

| | | |
|---|---|---|
| EP | 1777301 A2 | 4/2007 |
| WO | WO 2005/118806 A2 | 12/2005 |
| WO | WO 2006081284 A2 * | 8/2006 |
| WO | WO 2008029295 A2 * | 3/2008 |

OTHER PUBLICATIONS

Shedden et al. (Accurate Molecular Classification of Human Cancers Based on Gene Expression Using a Simple Classifier with a Pathological Tree-Based Framework, American Journal of Pathology, vol. 163, No. 5, Nov. 2003).*
Golub et al. (MicroRNA expression profiles classify human cancers, Nature, vol. 435, No. 9, Jun. 8, 2005).*
miR200c miRNAMap (hereinafter "Map"; 2005).*
Shi et al. (Facile means for quantifying microRNA expression by real-time PCR, BioTechniques 39:519-525 (Oct. 2005)).*
Xi et al. (Prognostic Values of microRNAs in Colorectal Cancer, Biomarker Insights 2006:1, 113-121, published online Feb. 7, 2007).*
Office Action received in the related U.S. Appl. No. 12/782,067, dated Mar. 18, 2013.
Notterman, et al., "Tumor Biiology and Microarray Analysis of Solid Tumors: Colorectal Cancer as a Model System", *Microarrays and Cancer Research*, 2002, Warrington et al., (eds.), Eaton Publishing, Westborough, MA, pp. 81-111.
Strausberg, et al., "Reading the Molecular Signatures of Cancer", Microarrays and Cancer Research, 2002, Warrington, et al. (eds.), Eaton Publishing, Westborough, MA, pp. 81-111.
The PTO form 892 received in the related U.S. Appl. No. 12/532,940 on Oct. 4, 2011.
Jukic, et al., "Microrna profiling analysis of differences between the melanoma of young adults and older adults", *Journal of Translational Medicine*, 2010, vol. 8, No. 27, pp. 1-23.
Leidinger, et al., "High-throughput miRNA profiling of human melanoma blood samples", *BMC Cancer*, 2010, vol. 10: 262, pp. 1-11.
MIR associated with Melanoma, Sep. 2011.
MIR-509 Results, Sep. 2011.

* cited by examiner

*Primary Examiner* — Christopher M Babic
*Assistant Examiner* — Aaron Priest
(74) *Attorney, Agent, or Firm* — Polsinelli PC; Teddy C. Scott, Jr.; Ron Galant

(57) ABSTRACT

The present invention provides a process for classification of cancers and tissues of origin through the analysis of the expression patterns of specific microRNAs and nucleic acid molecules relating thereto. Classification according to a microRNA tree-based expression framework allows optimization of treatment, and determination of specific therapy.

49 Claims, 11 Drawing Sheets

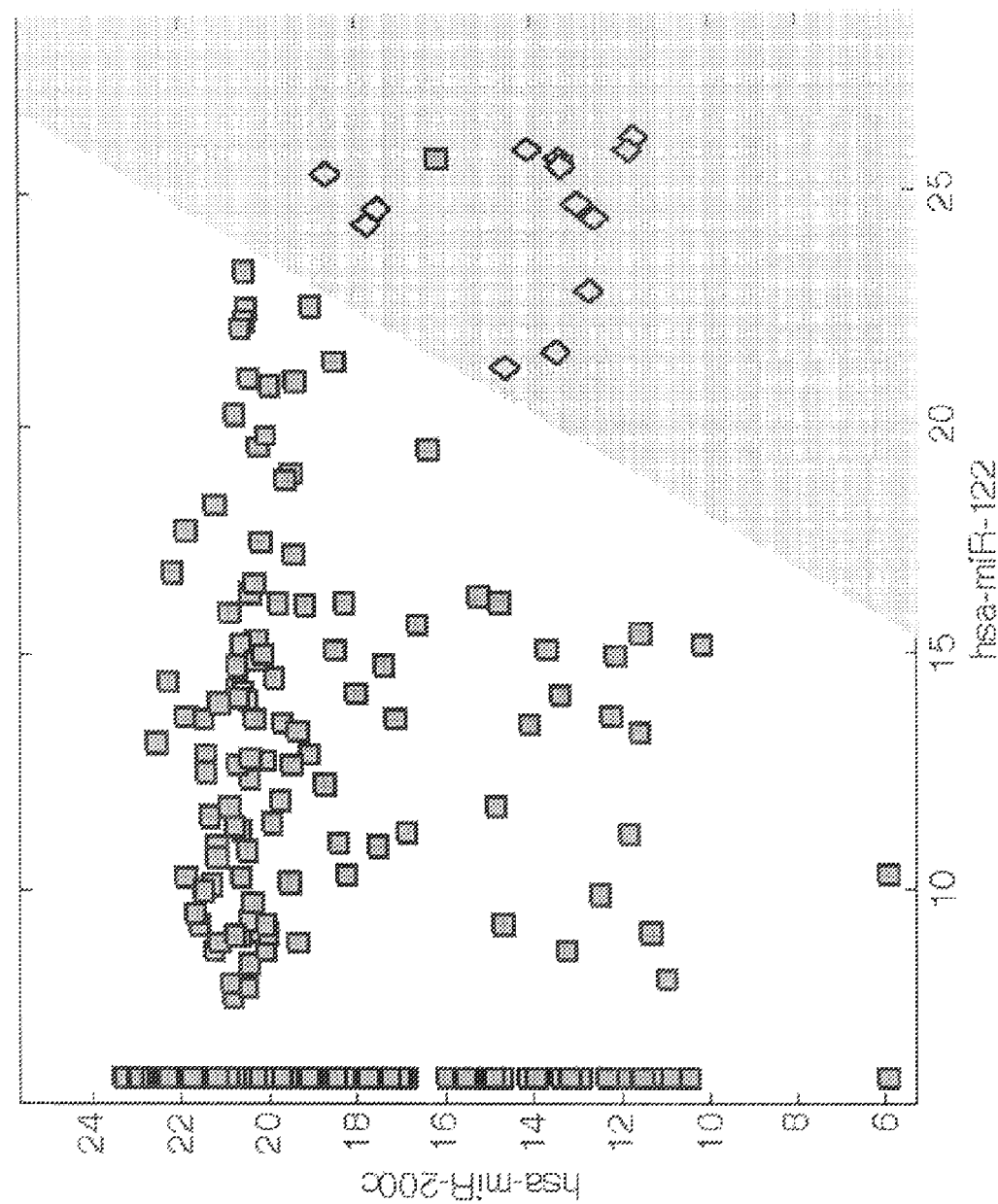

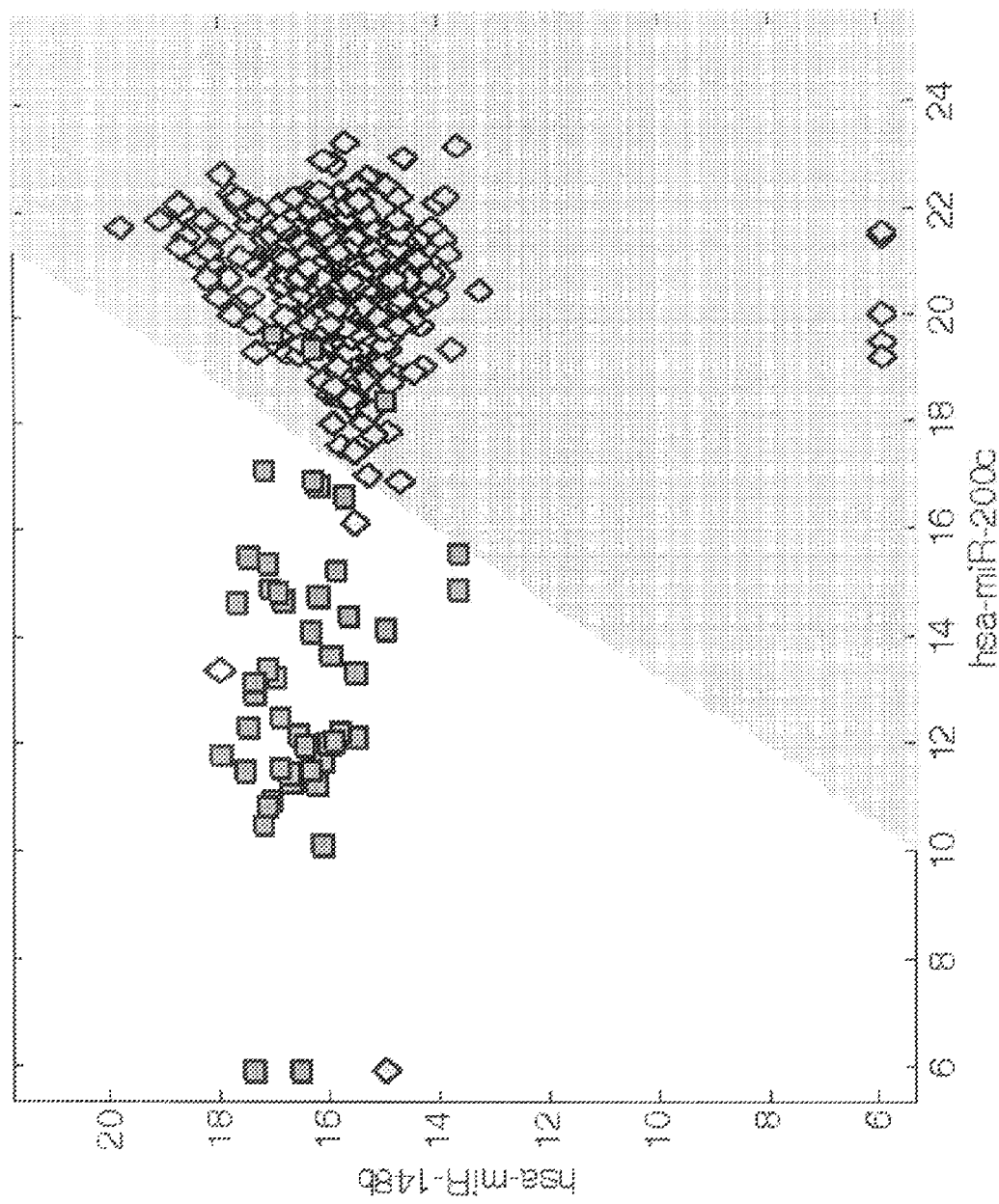

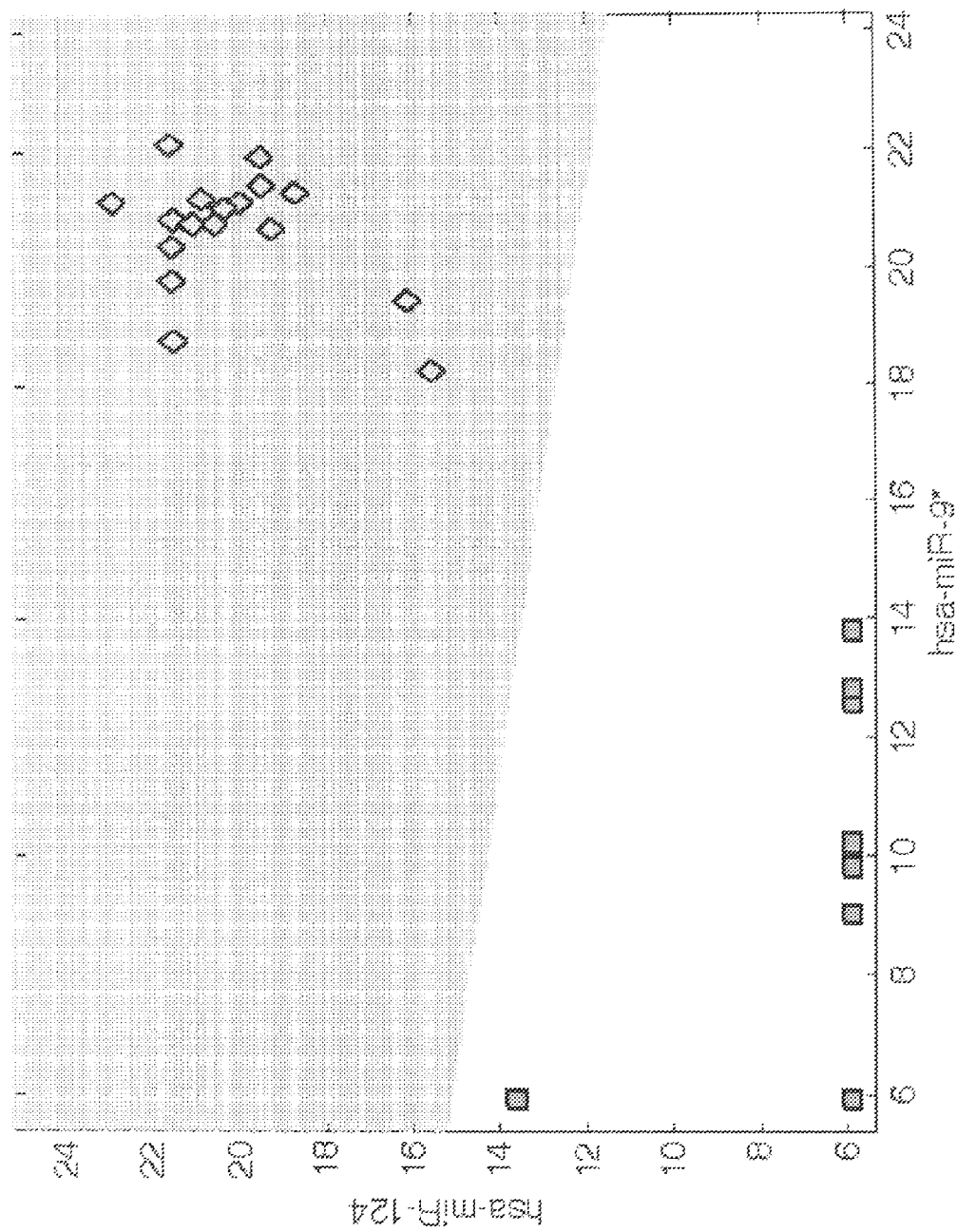

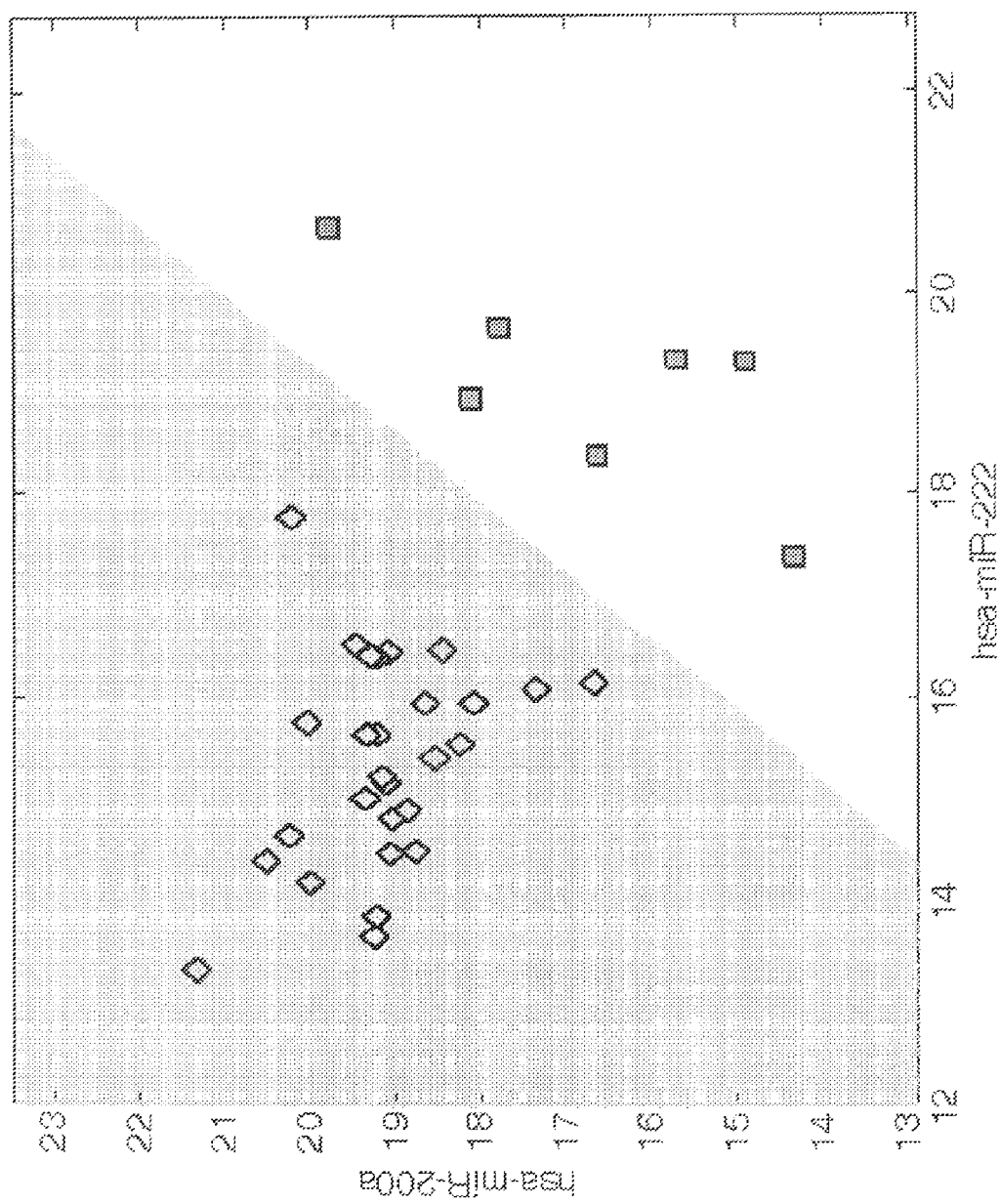

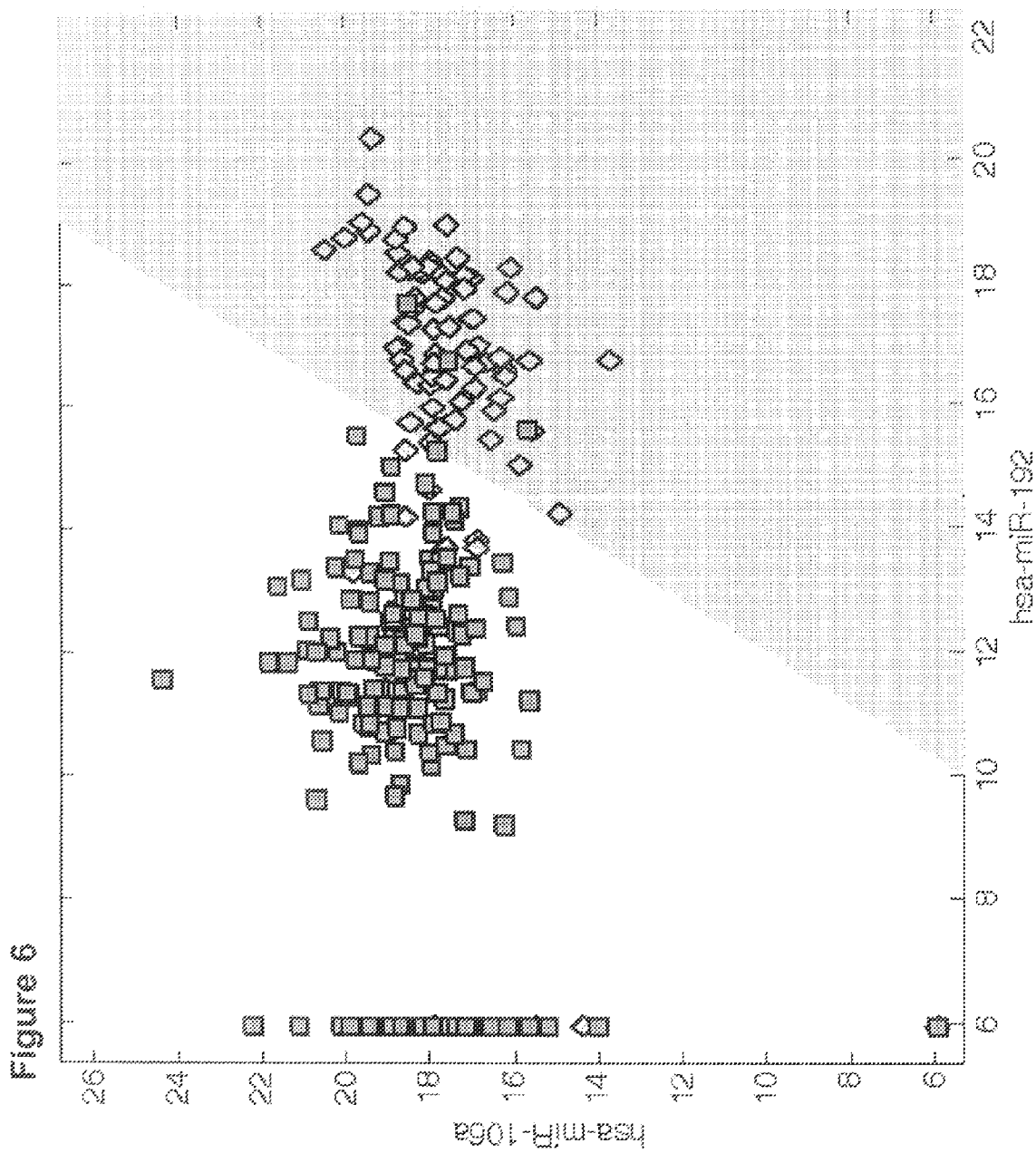

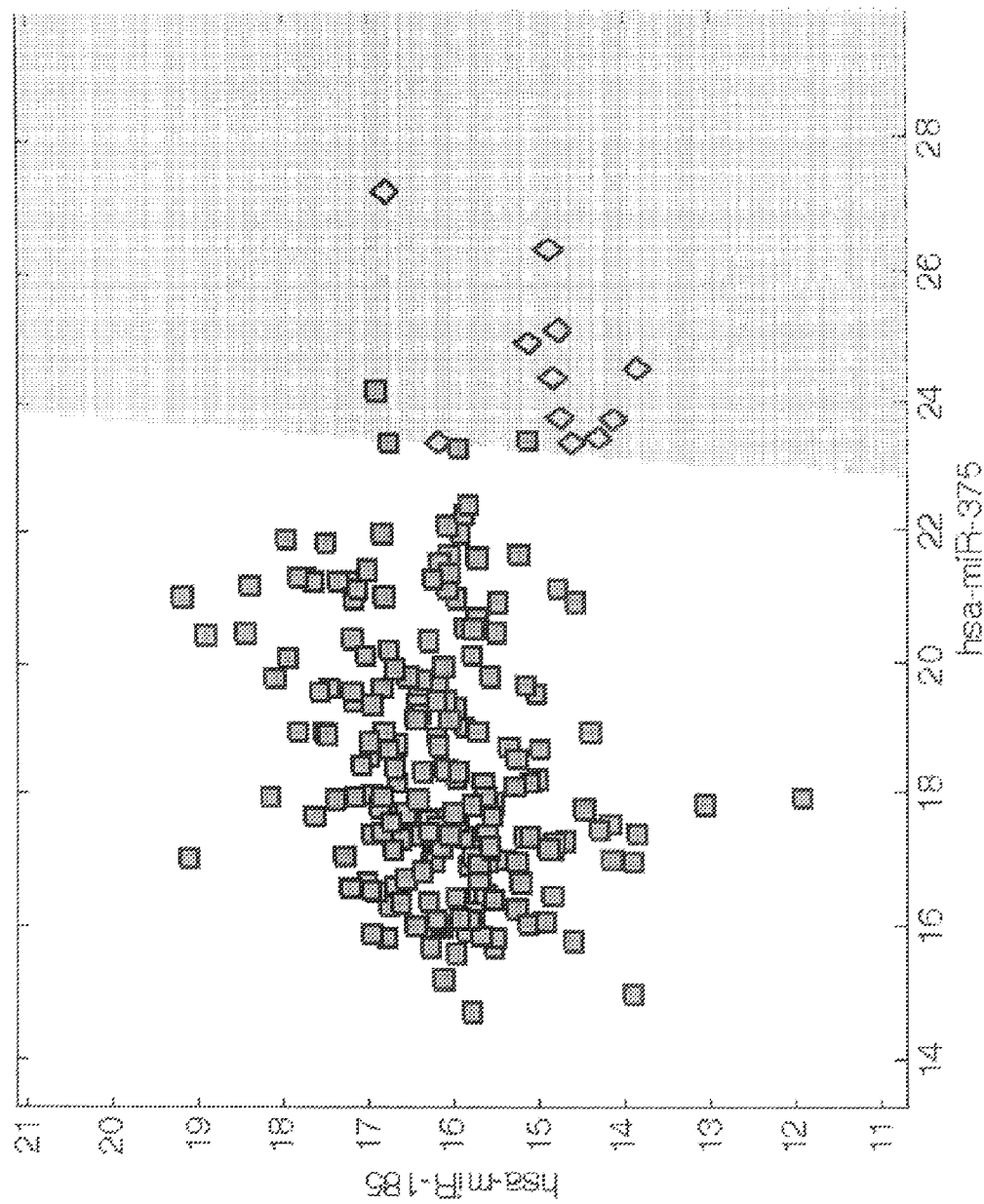

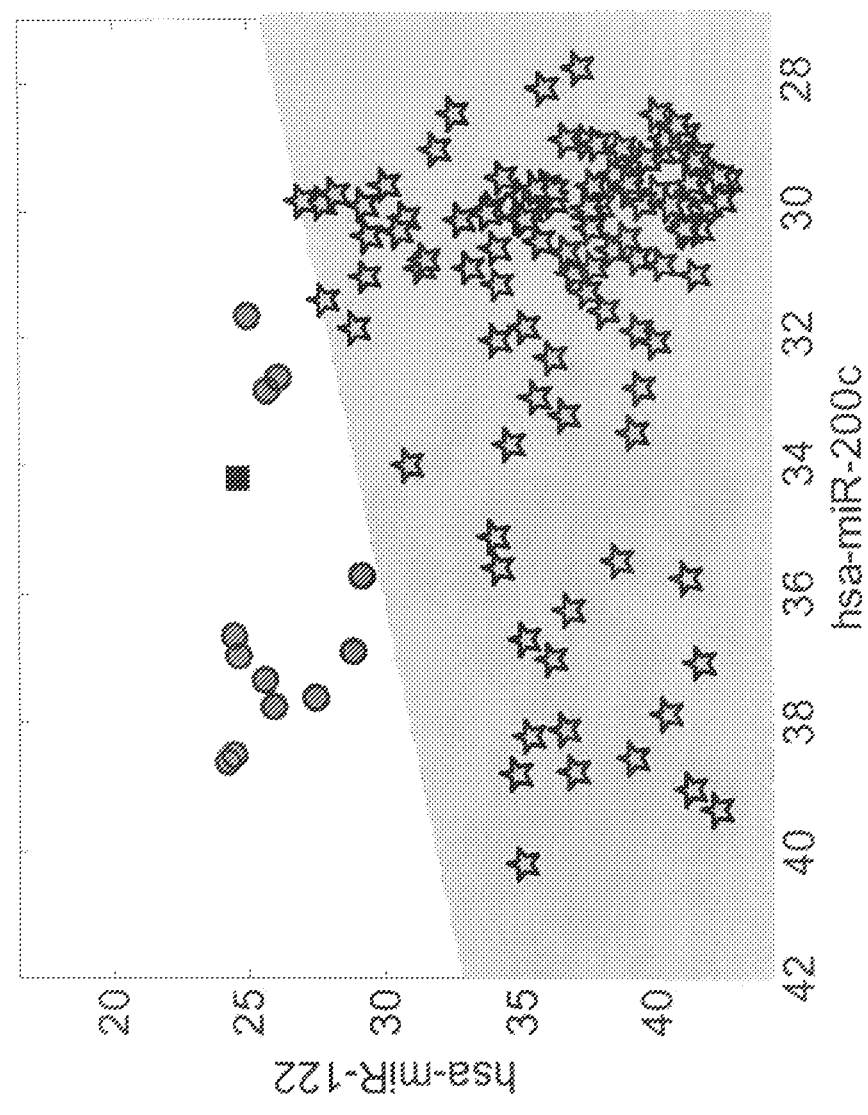

SEQUENCE LISTING

```
<160> NUMBER OF SEQ ID NOS: 288

<210> SEQ ID NO 1
<211> LENGTH: 22
<212> TYPE: RNA
<213> ORGANISM: Homo Sapiens

<400> SEQUENCE: 1
ugagguagua gguugugugg uu                                              22

<210> SEQ ID NO 2
<211> LENGTH: 22
<212> TYPE: RNA
<213> ORGANISM: Homo Sapiens

<400> SEQUENCE: 2
ugagguagua gauuguauag uu                                              22

<210> SEQ ID NO 3
<211> LENGTH: 23
<212> TYPE: RNA
<213> ORGANISM: Homo Sapiens

<400> SEQUENCE: 3
aaaagugcuu acagugcagg uag                                             23

<210> SEQ ID NO 4
<211> LENGTH: 23
<212> TYPE: RNA
<213> ORGANISM: Homo Sapiens

<400> SEQUENCE: 4
uacccuguag auccgaauuu gug                                             23

<210> SEQ ID NO 5
<211> LENGTH: 22
<212> TYPE: RNA
<213> ORGANISM: Homo Sapiens

<400> SEQUENCE: 5
uacccuguag aaccgaauuu gu                                              22

<210> SEQ ID NO 6
<211> LENGTH: 22
<212> TYPE: RNA
<213> ORGANISM: Homo Sapiens

<400> SEQUENCE: 6
uggaguguga caaugguguu ug                                              22

<210> SEQ ID NO 7
<211> LENGTH: 20
<212> TYPE: RNA
<213> ORGANISM: Homo Sapiens

<400> SEQUENCE: 7
uaaggcacgc ggugaaugcc                                                 20

<210> SEQ ID NO 8
<211> LENGTH: 22
<212> TYPE: RNA
<213> ORGANISM: Homo Sapiens

<400> SEQUENCE: 8
```
ucccugagac ccuaacuugu ga                                           22

<210> SEQ ID NO 9
<211> LENGTH: 22
<212> TYPE: RNA
<213> ORGANISM: Homo Sapiens

<400> SEQUENCE: 9
ucguaccgug aguaauaaug cg                                           22

<210> SEQ ID NO 10
<211> LENGTH: 21
<212> TYPE: RNA
<213> ORGANISM: Homo Sapiens

<400> SEQUENCE: 10
ucacagugaa ccggucucuu u                                            21

<210> SEQ ID NO 11
<211> LENGTH: 22
<212> TYPE: RNA
<213> ORGANISM: Homo Sapiens

<400> SEQUENCE: 11
cagugcaaug uuaaaagggc au                                           22

<210> SEQ ID NO 12
<211> LENGTH: 23
<212> TYPE: RNA
<213> ORGANISM: Homo Sapiens

<400> SEQUENCE: 12
agcugguguu gugaaucagg ccg                                          23

<210> SEQ ID NO 13
<211> LENGTH: 23
<212> TYPE: RNA
<213> ORGANISM: Homo Sapiens

<400> SEQUENCE: 13
uguaguguuu ccacuuuau gga                                           23

<210> SEQ ID NO 14
<211> LENGTH: 21
<212> TYPE: RNA
<213> ORGANISM: Homo Sapiens

<400> SEQUENCE: 14
ugagaugaag cacuguagcu c                                            21

<210> SEQ ID NO 15
<211> LENGTH: 22
<212> TYPE: RNA
<213> ORGANISM: Homo Sapiens

<400> SEQUENCE: 15
ugagaacuga auuccauggg uu                                           22

<210> SEQ ID NO 16
<211> LENGTH: 22
<212> TYPE: RNA
<213> ORGANISM: Homo Sapiens

```
<400> SEQUENCE: 16
ugagaacuga auuccauagg cu                                          22

<210> SEQ ID NO 17
<211> LENGTH: 22
<212> TYPE: RNA
<213> ORGANISM: Homo Sapiens

<400> SEQUENCE: 17
ucagugcauc acagaacuuu gu                                          22

<210> SEQ ID NO 18
<211> LENGTH: 21
<212> TYPE: RNA
<213> ORGANISM: Homo Sapiens

<400> SEQUENCE: 18
ucagugcaug acagaacuug g                                           21

<210> SEQ ID NO 19
<211> LENGTH: 22
<212> TYPE: RNA
<213> ORGANISM: Homo Sapiens

<400> SEQUENCE: 19
uagcagcaca ucaugguuua ca                                          22

<210> SEQ ID NO 20
<211> LENGTH: 22
<212> TYPE: RNA
<213> ORGANISM: Homo Sapiens

<400> SEQUENCE: 20
uggagagaaa ggcaguuccu ga                                          22

<210> SEQ ID NO 21
<211> LENGTH: 21
<212> TYPE: RNA
<213> ORGANISM: Homo Sapiens

<400> SEQUENCE: 21
cugaccuaug aauugacagc c                                           21

<210> SEQ ID NO 22
<211> LENGTH: 22
<212> TYPE: RNA
<213> ORGANISM: Homo Sapiens

<400> SEQUENCE: 22
aacuggccua caaaguccca gu                                          22

<210> SEQ ID NO 23
<211> LENGTH: 23
<212> TYPE: RNA
<213> ORGANISM: Homo Sapiens

<400> SEQUENCE: 23
ugugcaaauc caugcaaaac uga                                         23

<210> SEQ ID NO 24
<211> LENGTH: 23
<212> TYPE: RNA
<213> ORGANISM: Homo Sapiens
```

```
<400> SEQUENCE: 24
uaacacuguc ugguaacgau guu                                          23

<210> SEQ ID NO 25
<211> LENGTH: 22
<212> TYPE: RNA
<213> ORGANISM: Homo Sapiens

<400> SEQUENCE: 25
uaauacugcc ugguaaugau ga                                           22

<210> SEQ ID NO 26
<211> LENGTH: 23
<212> TYPE: RNA
<213> ORGANISM: Homo Sapiens

<400> SEQUENCE: 26
uaauacugcc ggguaaugau gga                                          23

<210> SEQ ID NO 27
<211> LENGTH: 22
<212> TYPE: RNA
<213> ORGANISM: Homo Sapiens

<400> SEQUENCE: 27
uccuucauuc caccggaguc ug                                           22

<210> SEQ ID NO 28
<211> LENGTH: 23
<212> TYPE: RNA
<213> ORGANISM: Homo Sapiens

<400> SEQUENCE: 28
uaaagugcuu auagugcagg uag                                          23

<210> SEQ ID NO 29
<211> LENGTH: 22
<212> TYPE: RNA
<213> ORGANISM: Homo Sapiens

<400> SEQUENCE: 29
uagcuuauca gacugauguu ga                                           22

<210> SEQ ID NO 30
<211> LENGTH: 22
<212> TYPE: RNA
<213> ORGANISM: Homo Sapiens

<400> SEQUENCE: 30
cugugcgugu gacagcggcu ga                                           22

<210> SEQ ID NO 31
<211> LENGTH: 23
<212> TYPE: RNA
<213> ORGANISM: Homo Sapiens

<400> SEQUENCE: 31
agcuacauug ucugcugggu uuc                                          23

<210> SEQ ID NO 32
<211> LENGTH: 21
<212> TYPE: RNA
```

<213> ORGANISM: Homo Sapiens

<400> SEQUENCE: 32
agcuacaucu ggcuacuggg u                                      21

<210> SEQ ID NO 33
<211> LENGTH: 22
<212> TYPE: RNA
<213> ORGANISM: Homo Sapiens

<400> SEQUENCE: 33
cauugcacuu gucucggucu ga                                     22

<210> SEQ ID NO 34
<211> LENGTH: 22
<212> TYPE: RNA
<213> ORGANISM: Homo Sapiens

<400> SEQUENCE: 34
uagcaccauc ugaaaucggu ua                                     22

<210> SEQ ID NO 35
<211> LENGTH: 23
<212> TYPE: RNA
<213> ORGANISM: Homo Sapiens

<400> SEQUENCE: 35
uagcaccauu ugaaaucagu guu                                    23

<210> SEQ ID NO 36
<211> LENGTH: 22
<212> TYPE: RNA
<213> ORGANISM: Homo Sapiens

<400> SEQUENCE: 36
uagcaccauu ugaaaucggu ua                                     22

<210> SEQ ID NO 37
<211> LENGTH: 22
<212> TYPE: RNA
<213> ORGANISM: Homo Sapiens

<400> SEQUENCE: 37
uguaaacauc cucgacugga ag                                     22

<210> SEQ ID NO 38
<211> LENGTH: 21
<212> TYPE: RNA
<213> ORGANISM: Homo Sapiens

<400> SEQUENCE: 38
aggcaagaug cuggcauagc u                                      21

<210> SEQ ID NO 39
<211> LENGTH: 23
<212> TYPE: RNA
<213> ORGANISM: Homo Sapiens

<400> SEQUENCE: 39
ucucacacag aaaucgcacc cgu                                    23

<210> SEQ ID NO 40
<211> LENGTH: 22

<212> TYPE: RNA
<213> ORGANISM: Homo Sapiens

<400> SEQUENCE: 40
gcugacuccu aguccagggc uc					22

<210> SEQ ID NO 41
<211> LENGTH: 23
<212> TYPE: RNA
<213> ORGANISM: Homo Sapiens

<400> SEQUENCE: 41
aaagugcugc gacauuugag cgu					23

<210> SEQ ID NO 42
<211> LENGTH: 22
<212> TYPE: RNA
<213> ORGANISM: Homo Sapiens

<400> SEQUENCE: 42
uuuguucguu cggcucgcgu ga					22

<210> SEQ ID NO 43
<211> LENGTH: 21
<212> TYPE: RNA
<213> ORGANISM: Homo Sapiens

<400> SEQUENCE: 43
acuggacuug gagucagaag g						21

<210> SEQ ID NO 44
<211> LENGTH: 23
<212> TYPE: RNA
<213> ORGANISM: Homo Sapiens

<400> SEQUENCE: 44
aaugacacga ucacucccgu uga					23

<210> SEQ ID NO 45
<211> LENGTH: 21
<212> TYPE: RNA
<213> ORGANISM: Homo Sapiens

<400> SEQUENCE: 45
aaaccguuac cauuacugag u						21

<210> SEQ ID NO 46
<211> LENGTH: 21
<212> TYPE: RNA
<213> ORGANISM: Homo Sapiens

<400> SEQUENCE: 46
cagcagcaca cugugguuug u						21

<210> SEQ ID NO 47
<211> LENGTH: 22
<212> TYPE: RNA
<213> ORGANISM: Homo Sapiens

<400> SEQUENCE: 47
auaaagcuag auaaccgaaa gu					22

<210> SEQ ID NO 48

```
<211> LENGTH: 22
<212> TYPE: RNA
<213> ORGANISM: Homo Sapiens

<400> SEQUENCE: 48
uauugcacuc gucccggccu cc                                              22

<210> SEQ ID NO 49
<211> LENGTH: 22
<212> TYPE: RNA
<213> ORGANISM: Homo Sapiens

<400> SEQUENCE: 49 ugauuggua cgucuguggu ag                                               22

<210> SEQ ID NO 50
<211> LENGTH: 28
<212> TYPE: DNA
<213> ORGANISM: Artificial Sequence
<220> FEATURE:
<223> OTHER INFORMATION: Synthetic

<400> SEQUENCE: 50
cagtcatttg gctgaggtag taggttgt                                        28

<210> SEQ ID NO 51
<211> LENGTH: 28
<212> TYPE: DNA
<213> ORGANISM: Artificial Sequence
<220> FEATURE:
<223> OTHER INFORMATION: Synthetic

<400> SEQUENCE: 51
cagtcatttg ggtgaggtag tagattgt                                        28

<210> SEQ ID NO 52
<211> LENGTH: 29
<212> TYPE: DNA
<213> ORGANISM: Artificial Sequence
<220> FEATURE:
<223> OTHER INFORMATION: Synthetic

<400> SEQUENCE: 52
cagtcatttg gaaaagtgct tacagtgca                                       29

<210> SEQ ID NO 53
<211> LENGTH: 28
<212> TYPE: DNA
<213> ORGANISM: Artificial Sequence
<220> FEATURE:
<223> OTHER INFORMATION: Synthetic

<400> SEQUENCE: 53
cagtcatttg gctaccctgt agatccga                                        28

<210> SEQ ID NO 54
<211> LENGTH: 30
<212> TYPE: DNA
<213> ORGANISM: Artificial Sequence
<220> FEATURE:
<223> OTHER INFORMATION: Synthetic

<400> SEQUENCE: 54
cagtcatttg gctaccctgt agaaccgaat                                      30
```

```
<210> SEQ ID NO 55
<211> LENGTH: 28
<212> TYPE: DNA
<213> ORGANISM: Artificial Sequence
<220> FEATURE:
<223> OTHER INFORMATION: Synthetic

<400> SEQUENCE: 55
cagtcatttg ggtggagtgt gacaatgg                                          28

<210> SEQ ID NO 56
<211> LENGTH: 28
<212> TYPE: DNA
<213> ORGANISM: Artificial Sequence
<220> FEATURE:
<223> OTHER INFORMATION: Synthetic

<400> SEQUENCE: 56
cagtcatttg gctaaggcac gcggtgaa                                          28

<210> SEQ ID NO 57
<211> LENGTH: 28
<212> TYPE: DNA
<213> ORGANISM: Artificial Sequence
<220> FEATURE:
<223> OTHER INFORMATION: Synthetic

<400> SEQUENCE: 57
cagtcatttg ggtccctgag accctaac                                          28

<210> SEQ ID NO 58
<211> LENGTH: 28
<212> TYPE: DNA
<213> ORGANISM: Artificial Sequence
<220> FEATURE:
<223> OTHER INFORMATION: Synthetic

<400> SEQUENCE: 58
cagtcatttg ggtcgtaccg tgagtaat                                          28

<210> SEQ ID NO 59
<211> LENGTH: 28
<212> TYPE: DNA
<213> ORGANISM: Artificial Sequence
<220> FEATURE:
<223> OTHER INFORMATION: Synthetic

<400> SEQUENCE: 59
cagtcatttg gctcacagtg aaccggtc                                          28

<210> SEQ ID NO 60
<211> LENGTH: 28
<212> TYPE: DNA
<213> ORGANISM: Artificial Sequence
<220> FEATURE:
<223> OTHER INFORMATION: Synthetic

<400> SEQUENCE: 60
cagtcatttg ggcagtgcaa tgttaaaa                                          28

<210> SEQ ID NO 61
<211> LENGTH: 28
<212> TYPE: DNA
<213> ORGANISM: Artificial Sequence
<220> FEATURE:
<223> OTHER INFORMATION: Synthetic
```

```
<400> SEQUENCE: 61
cagtcatttg gcagctggtg ttgtgaat                                28

<210> SEQ ID NO 62
<211> LENGTH: 28
<212> TYPE: DNA
<213> ORGANISM: Artificial Sequence
<220> FEATURE:
<223> OTHER INFORMATION: Synthetic

<400> SEQUENCE: 62
cagtcatttg ggtgtagtgt ttcctact                                28

<210> SEQ ID NO 63
<211> LENGTH: 28
<212> TYPE: DNA
<213> ORGANISM: Artificial Sequence
<220> FEATURE:
<223> OTHER INFORMATION: Synthetic

<400> SEQUENCE: 63
cagtcatttg gctgagatga agcactgt                                28

<210> SEQ ID NO 64
<211> LENGTH: 28
<212> TYPE: DNA
<213> ORGANISM: Artificial Sequence
<220> FEATURE:
<223> OTHER INFORMATION: Synthetic

<400> SEQUENCE: 64
cagtcatttg gctgagaact gaattcca                                28

<210> SEQ ID NO 65
<211> LENGTH: 28
<212> TYPE: DNA
<213> ORGANISM: Artificial Sequence
<220> FEATURE:
<223> OTHER INFORMATION: Synthetic

<400> SEQUENCE: 65
cagtcatttg gctgagaact gaattcca                                28

<210> SEQ ID NO 66
<211> LENGTH: 28
<212> TYPE: DNA
<213> ORGANISM: Artificial Sequence
<220> FEATURE:
<223> OTHER INFORMATION: Synthetic

<400> SEQUENCE: 66
cagtcatttg gctcagtgca tcacagaa                                28

<210> SEQ ID NO 67
<211> LENGTH: 28
<212> TYPE: DNA
<213> ORGANISM: Artificial Sequence
<220> FEATURE:
<223> OTHER INFORMATION: Synthetic

<400> SEQUENCE: 67
cagtcatttg gctcagtgca tgacagaa                                28

<210> SEQ ID NO 68
<211> LENGTH: 28
```

<212> TYPE: DNA
<213> ORGANISM: Artificial Sequence
<220> FEATURE:
<223> OTHER INFORMATION: Synthetic

<400> SEQUENCE: 68
cagtcatttg gctagcagca catcatgg                                           28

<210> SEQ ID NO 69
<211> LENGTH: 28
<212> TYPE: DNA
<213> ORGANISM: Artificial Sequence
<220> FEATURE:
<223> OTHER INFORMATION: Synthetic

<400> SEQUENCE: 69
cagtcatttg gctggagaga aaggcagt                                           28

<210> SEQ ID NO 70
<211> LENGTH: 28
<212> TYPE: DNA
<213> ORGANISM: Artificial Sequence
<220> FEATURE:
<223> OTHER INFORMATION: Synthetic

<400> SEQUENCE: 70
cagtcatttg ggctgaccta tgaattga                                           28

<210> SEQ ID NO 71
<211> LENGTH: 28
<212> TYPE: DNA
<213> ORGANISM: Artificial Sequence
<220> FEATURE:
<223> OTHER INFORMATION: Synthetic

<400> SEQUENCE: 71
cagtcatttg ggaactggcc tacaaagt                                           28

<210> SEQ ID NO 72
<211> LENGTH: 28
<212> TYPE: DNA
<213> ORGANISM: Artificial Sequence
<220> FEATURE:
<223> OTHER INFORMATION: Synthetic

<400> SEQUENCE: 72
cagtcatttg gctgtgcaaa tccatgca                                           28

<210> SEQ ID NO 73
<211> LENGTH: 28
<212> TYPE: DNA
<213> ORGANISM: Artificial Sequence
<220> FEATURE:
<223> OTHER INFORMATION: Synthetic

<400> SEQUENCE: 73
cagtcatttg ggtaacactg tctggtaa                                           28

<210> SEQ ID NO 74
<211> LENGTH: 28
<212> TYPE: DNA
<213> ORGANISM: Artificial Sequence
<220> FEATURE:
<223> OTHER INFORMATION: Synthetic

<400> SEQUENCE: 74

```
cagtcatttg ggtaatactg cctggtaa                                              28

<210> SEQ ID NO 75
<211> LENGTH: 28
<212> TYPE: DNA
<213> ORGANISM: Artificial Sequence
<220> FEATURE:
<223> OTHER INFORMATION: Synthetic

<400> SEQUENCE: 75
cagtcatttg ggtaatactg ccgggtaa                                              28

<210> SEQ ID NO 76
<211> LENGTH: 28
<212> TYPE: DNA
<213> ORGANISM: Artificial Sequence
<220> FEATURE:
<223> OTHER INFORMATION: Synthetic

<400> SEQUENCE: 76
cagtcatttg gctccttcat tccaccgg                                              28

<210> SEQ ID NO 77
<211> LENGTH: 29
<212> TYPE: DNA
<213> ORGANISM: Artificial Sequence
<220> FEATURE:
<223> OTHER INFORMATION: Synthetic

<400> SEQUENCE: 77
cagtcatttg gtaaagtgct tatagtgca                                             29

<210> SEQ ID NO 78
<211> LENGTH: 28
<212> TYPE: DNA
<213> ORGANISM: Artificial Sequence
<220> FEATURE:
<223> OTHER INFORMATION: Synthetic

<400> SEQUENCE: 78
cagtcatttg gctagcttat cagactga                                              28

<210> SEQ ID NO 79
<211> LENGTH: 28
<212> TYPE: DNA
<213> ORGANISM: Artificial Sequence
<220> FEATURE:
<223> OTHER INFORMATION: Synthetic

<400> SEQUENCE: 79
cagtcatttg ggctgtgcgt gtgacagc                                              28

<210> SEQ ID NO 80
<211> LENGTH: 28
<212> TYPE: DNA
<213> ORGANISM: Artificial Sequence
<220> FEATURE:
<223> OTHER INFORMATION: Synthetic

<400> SEQUENCE: 80
cagtcatttg ggagctacat tgtctgct                                              28

<210> SEQ ID NO 81
<211> LENGTH: 28
<212> TYPE: DNA
<213> ORGANISM: Artificial Sequence
```

<220> FEATURE:
<223> OTHER INFORMATION: Synthetic

<400> SEQUENCE: 81
cagtcatttg ggagctacat ctggctac                28

<210> SEQ ID NO 82
<211> LENGTH: 28
<212> TYPE: DNA
<213> ORGANISM: Artificial Sequence
<220> FEATURE:
<223> OTHER INFORMATION: Synthetic

<400> SEQUENCE: 82
cagtcatttg gccattgcac ttgtctcg                28

<210> SEQ ID NO 83
<211> LENGTH: 29
<212> TYPE: DNA
<213> ORGANISM: Artificial Sequence
<220> FEATURE:
<223> OTHER INFORMATION: Synthetic

<400> SEQUENCE: 83
cagtcatttg gtagcaccat ctgaaatcg               29

<210> SEQ ID NO 84
<211> LENGTH: 28
<212> TYPE: DNA
<213> ORGANISM: Artificial Sequence
<220> FEATURE:
<223> OTHER INFORMATION: Synthetic

<400> SEQUENCE: 84
cagtcatttg gctagcacca tttgaaat                28

<210> SEQ ID NO 85
<211> LENGTH: 28
<212> TYPE: DNA
<213> ORGANISM: Artificial Sequence
<220> FEATURE:
<223> OTHER INFORMATION: Synthetic

<400> SEQUENCE: 85
cagtcatttg gctagcacca tttgaaat                28

<210> SEQ ID NO 86
<211> LENGTH: 28
<212> TYPE: DNA
<213> ORGANISM: Artificial Sequence
<220> FEATURE:
<223> OTHER INFORMATION: Synthetic

<400> SEQUENCE: 86
cagtcatttg ggtgtaaaca tcctcgac                28

<210> SEQ ID NO 87
<211> LENGTH: 28
<212> TYPE: DNA
<213> ORGANISM: Artificial Sequence
<220> FEATURE:
<223> OTHER INFORMATION: Synthetic

<400> SEQUENCE: 87
cagtcatttg gcaggcaaga tgctggca                28

```
<210> SEQ ID NO 88
<211> LENGTH: 28
<212> TYPE: DNA
<213> ORGANISM: Artificial Sequence
<220> FEATURE:
<223> OTHER INFORMATION: Synthetic

<400> SEQUENCE: 88
cagtcatttg ggtctcacac agaaatcg                                    28

<210> SEQ ID NO 89
<211> LENGTH: 28
<212> TYPE: DNA
<213> ORGANISM: Artificial Sequence
<220> FEATURE:
<223> OTHER INFORMATION: Synthetic

<400> SEQUENCE: 89
cagtcatttg gcgctgactc ctagtcca                                    28

<210> SEQ ID NO 90
<211> LENGTH: 28
<212> TYPE: DNA
<213> ORGANISM: Artificial Sequence
<220> FEATURE:
<223> OTHER INFORMATION: Synthetic

<400> SEQUENCE: 90
cagtcatttg ggaaagtgct gcgacatt                                    28

<210> SEQ ID NO 91
<211> LENGTH: 28
<212> TYPE: DNA
<213> ORGANISM: Artificial Sequence
<220> FEATURE:
<223> OTHER INFORMATION: Synthetic

<400> SEQUENCE: 91
cagtcatttg ggtttgttcg ttcggctc                                    28

<210> SEQ ID NO 92
<211> LENGTH: 28
<212> TYPE: DNA
<213> ORGANISM: Artificial Sequence
<220> FEATURE:
<223> OTHER INFORMATION: Synthetic

<400> SEQUENCE: 92
cagtcatttg gcactggact tggagtca                                    28

<210> SEQ ID NO 93
<211> LENGTH: 28
<212> TYPE: DNA
<213> ORGANISM: Artificial Sequence
<220> FEATURE:
<223> OTHER INFORMATION: Synthetic

<400> SEQUENCE: 93
cagtcatttg gcaatgacac gatcactc                                    28

<210> SEQ ID NO 94
<211> LENGTH: 28
<212> TYPE: DNA
<213> ORGANISM: Artificial Sequence
<220> FEATURE:
<223> OTHER INFORMATION: Synthetic
```

<400> SEQUENCE: 94
cagtcatttg ggaaaccgtt accattac                                28

<210> SEQ ID NO 95
<211> LENGTH: 28
<212> TYPE: DNA
<213> ORGANISM: Artificial Sequence
<220> FEATURE:
<223> OTHER INFORMATION: Synthetic

<400> SEQUENCE: 95
cagtcatttg gccagcagca cactgtgg                                28

<210> SEQ ID NO 96
<211> LENGTH: 28
<212> TYPE: DNA
<213> ORGANISM: Artificial Sequence
<220> FEATURE:
<223> OTHER INFORMATION: Synthetic

<400> SEQUENCE: 96
cagtcatttg gcataaagct agataacc                                28

<210> SEQ ID NO 97
<211> LENGTH: 28
<212> TYPE: DNA
<213> ORGANISM: Artificial Sequence
<220> FEATURE:
<223> OTHER INFORMATION: Synthetic

<400> SEQUENCE: 97
cagtcatttg ggtattgcac tcgtcccg                                28

<210> SEQ ID NO 98
<211> LENGTH: 21
<212> TYPE: DNA
<213> ORGANISM: Artificial Sequence
<220> FEATURE:
<223> OTHER INFORMATION: Synthetic

<400> SEQUENCE: 98
gcaaggatga cacgcaaatt c                                       21

<210> SEQ ID NO 99
<211> LENGTH: 23
<212> TYPE: DNA
<213> ORGANISM: Artificial Sequence
<220> FEATURE:
<223> OTHER INFORMATION: Synthetic

<400> SEQUENCE: 99
ccgttttttt tttttaacca cac                                     23

<210> SEQ ID NO 100
<211> LENGTH: 23
<212> TYPE: DNA
<213> ORGANISM: Artificial Sequence
<220> FEATURE:
<223> OTHER INFORMATION: Synthetic

<400> SEQUENCE: 100
ccgttttttt tttttaacta tac                                     23

<210> SEQ ID NO 101

```
<211> LENGTH: 23
<212> TYPE: DNA
<213> ORGANISM: Artificial Sequence
<220> FEATURE:
<223> OTHER INFORMATION: Synthetic

<400> SEQUENCE: 101
ccgttttttt tttttctacc tgc                                              23

<210> SEQ ID NO 102
<211> LENGTH: 22
<212> TYPE: DNA
<213> ORGANISM: Artificial Sequence
<220> FEATURE:
<223> OTHER INFORMATION: Synthetic

<400> SEQUENCE: 102 cgttttttttt ttttcacaaa tt                                              22

<210> SEQ ID NO 103
<211> LENGTH: 22
<212> TYPE: DNA
<213> ORGANISM: Artificial Sequence
<220> FEATURE:
<223> OTHER INFORMATION: Synthetic

<400> SEQUENCE: 103 cgttttttttt tttacaaat tc                                               22

<210> SEQ ID NO 104
<211> LENGTH: 22
<212> TYPE: DNA
<213> ORGANISM: Artificial Sequence
<220> FEATURE:
<223> OTHER INFORMATION: Synthetic

<400> SEQUENCE: 104 cgttttttttt tttcaaaca cc                                               22

<210> SEQ ID NO 105
<211> LENGTH: 23
<212> TYPE: DNA
<213> ORGANISM: Artificial Sequence
<220> FEATURE:
<223> OTHER INFORMATION: Synthetic

<400> SEQUENCE: 105
ccgttttttt tttttggcat tca                                              23

<210> SEQ ID NO 106
<211> LENGTH: 23
<212> TYPE: DNA
<213> ORGANISM: Artificial Sequence
<220> FEATURE:
<223> OTHER INFORMATION: Synthetic

<400> SEQUENCE: 106
ccgttttttt tttttcacaa gtt                                              23

<210> SEQ ID NO 107
<211> LENGTH: 23
<212> TYPE: DNA
<213> ORGANISM: Artificial Sequence
<220> FEATURE:
<223> OTHER INFORMATION: Synthetic

<400> SEQUENCE: 107
``` ccgtttttttt tttttcgcat tat                                          23

<210> SEQ ID NO 108
<211> LENGTH: 23
<212> TYPE: DNA
<213> ORGANISM: Artificial Sequence
<220> FEATURE:
<223> OTHER INFORMATION: Synthetic

<400> SEQUENCE: 108 ccgtttttttt tttttaaaga gac                                          23

<210> SEQ ID NO 109
<211> LENGTH: 23
<212> TYPE: DNA
<213> ORGANISM: Artificial Sequence
<220> FEATURE:
<223> OTHER INFORMATION: Synthetic

<400> SEQUENCE: 109 ccgtttttttt tttttatgcc ctt                                          23

<210> SEQ ID NO 110
<211> LENGTH: 22
<212> TYPE: DNA
<213> ORGANISM: Artificial Sequence
<220> FEATURE:
<223> OTHER INFORMATION: Synthetic

<400> SEQUENCE: 110
cgtttttttt ttttcggcct ga                                            22

<210> SEQ ID NO 111
<211> LENGTH: 23
<212> TYPE: DNA
<213> ORGANISM: Artificial Sequence
<220> FEATURE:
<223> OTHER INFORMATION: Synthetic

<400> SEQUENCE: 111 ccgtttttttt tttttccata aag                                          23

<210> SEQ ID NO 112
<211> LENGTH: 23
<212> TYPE: DNA
<213> ORGANISM: Artificial Sequence
<220> FEATURE:
<223> OTHER INFORMATION: Synthetic

<400> SEQUENCE: 112 ccgtttttttt tttttgagct aca                                          23

<210> SEQ ID NO 113
<211> LENGTH: 23
<212> TYPE: DNA
<213> ORGANISM: Artificial Sequence
<220> FEATURE:
<223> OTHER INFORMATION: Synthetic

<400> SEQUENCE: 113 ccgtttttttt tttttaaccc atg                                          23

<210> SEQ ID NO 114
<211> LENGTH: 23
<212> TYPE: DNA

```
<213> ORGANISM: Artificial Sequence
<220> FEATURE:
<223> OTHER INFORMATION: Synthetic

<400> SEQUENCE: 114 ccgtttttttt tttttagcct atg                                          23

<210> SEQ ID NO 115
<211> LENGTH: 23
<212> TYPE: DNA
<213> ORGANISM: Artificial Sequence
<220> FEATURE:
<223> OTHER INFORMATION: Synthetic

<400> SEQUENCE: 115 ccgtttttttt tttttacaaa gtt                                          23

<210> SEQ ID NO 116
<211> LENGTH: 22
<212> TYPE: DNA
<213> ORGANISM: Artificial Sequence
<220> FEATURE:
<223> OTHER INFORMATION: Synthetic

<400> SEQUENCE: 116
cgtttttttt ttttccaagt tc                                            22

<210> SEQ ID NO 117
<211> LENGTH: 23
<212> TYPE: DNA
<213> ORGANISM: Artificial Sequence
<220> FEATURE:
<223> OTHER INFORMATION: Synthetic

<400> SEQUENCE: 117 ccgtttttttt tttttgtaaa cca                                          23

<210> SEQ ID NO 118
<211> LENGTH: 22
<212> TYPE: DNA
<213> ORGANISM: Artificial Sequence
<220> FEATURE:
<223> OTHER INFORMATION: Synthetic

<400> SEQUENCE: 118
cgtttttttt ttttcaggaa ct                                            22

<210> SEQ ID NO 119
<211> LENGTH: 23
<212> TYPE: DNA
<213> ORGANISM: Artificial Sequence
<220> FEATURE:
<223> OTHER INFORMATION: Synthetic

<400> SEQUENCE: 119 ccgtttttttt tttttggctg tca                                          23

<210> SEQ ID NO 120
<211> LENGTH: 22
<212> TYPE: DNA
<213> ORGANISM: Artificial Sequence
<220> FEATURE:
<223> OTHER INFORMATION: Synthetic

<400> SEQUENCE: 120
cgtttttttt ttttggctgt ca                                            22
```

<210> SEQ ID NO 121
<211> LENGTH: 23
<212> TYPE: DNA
<213> ORGANISM: Artificial Sequence
<220> FEATURE:
<223> OTHER INFORMATION: Synthetic

<400> SEQUENCE: 121 ccgtttttttt tttttactgg gac    23

<210> SEQ ID NO 122
<211> LENGTH: 22
<212> TYPE: DNA
<213> ORGANISM: Artificial Sequence
<220> FEATURE:
<223> OTHER INFORMATION: Synthetic

<400> SEQUENCE: 122
cgtttttttt ttttcagttt tg    22

<210> SEQ ID NO 123
<211> LENGTH: 23
<212> TYPE: DNA
<213> ORGANISM: Artificial Sequence
<220> FEATURE:
<223> OTHER INFORMATION: Synthetic

<400> SEQUENCE: 123 ccgtttttttt tttttaacat cgt    23

<210> SEQ ID NO 124
<211> LENGTH: 23
<212> TYPE: DNA
<213> ORGANISM: Artificial Sequence
<220> FEATURE:
<223> OTHER INFORMATION: Synthetic

<400> SEQUENCE: 124 ccgtttttttt tttttcatca tta    23

<210> SEQ ID NO 125
<211> LENGTH: 23
<212> TYPE: DNA
<213> ORGANISM: Artificial Sequence
<220> FEATURE:
<223> OTHER INFORMATION: Synthetic

<400> SEQUENCE: 125 ccgtttttttt tttttccatc att    23

<210> SEQ ID NO 126
<211> LENGTH: 22
<212> TYPE: DNA
<213> ORGANISM: Artificial Sequence
<220> FEATURE:
<223> OTHER INFORMATION: Synthetic

<400> SEQUENCE: 126
cgtttttttt ttttccatca tt    22

<210> SEQ ID NO 127
<211> LENGTH: 22
<212> TYPE: DNA
<213> ORGANISM: Artificial Sequence
<220> FEATURE:

<223> OTHER INFORMATION: Synthetic

<400> SEQUENCE: 127 cgttttttt ttttcagact cc                                    22

<210> SEQ ID NO 128
<211> LENGTH: 23
<212> TYPE: DNA
<213> ORGANISM: Artificial Sequence
<220> FEATURE:
<223> OTHER INFORMATION: Synthetic

<400> SEQUENCE: 128
ccgttttttt tttttctacc tgc                                   23

<210> SEQ ID NO 129
<211> LENGTH: 23
<212> TYPE: DNA
<213> ORGANISM: Artificial Sequence
<220> FEATURE:
<223> OTHER INFORMATION: Synthetic

<400> SEQUENCE: 129
ccgttttttt tttttcaaca tca                                   23

<210> SEQ ID NO 130
<211> LENGTH: 22
<212> TYPE: DNA
<213> ORGANISM: Artificial Sequence
<220> FEATURE:
<223> OTHER INFORMATION: Synthetic

<400> SEQUENCE: 130 cgttttttt ttttcagccg ct                                    22

<210> SEQ ID NO 131
<211> LENGTH: 22
<212> TYPE: DNA
<213> ORGANISM: Artificial Sequence
<220> FEATURE:
<223> OTHER INFORMATION: Synthetic

<400> SEQUENCE: 131 cgttttttt ttttgaaacc ca                                    22

<210> SEQ ID NO 132
<211> LENGTH: 25
<212> TYPE: DNA
<213> ORGANISM: Artificial Sequence
<220> FEATURE:
<223> OTHER INFORMATION: Synthetic

<400> SEQUENCE: 132
atccgttttt ttttttacc cagta                                  25

<210> SEQ ID NO 133
<211> LENGTH: 23
<212> TYPE: DNA
<213> ORGANISM: Artificial Sequence
<220> FEATURE:
<223> OTHER INFORMATION: Synthetic

<400> SEQUENCE: 133
ccgttttttt tttttcagac cga                                   23

```
<210> SEQ ID NO 134
<211> LENGTH: 23
<212> TYPE: DNA
<213> ORGANISM: Artificial Sequence
<220> FEATURE:
<223> OTHER INFORMATION: Synthetic

<400> SEQUENCE: 134
ccgttttttt tttttaaccg att                                              23

<210> SEQ ID NO 135
<211> LENGTH: 24
<212> TYPE: DNA
<213> ORGANISM: Artificial Sequence
<220> FEATURE:
<223> OTHER INFORMATION: Synthetic

<400> SEQUENCE: 135 tccgttttttt tttttaaca ctga                                             24

<210> SEQ ID NO 136
<211> LENGTH: 23
<212> TYPE: DNA
<213> ORGANISM: Artificial Sequence
<220> FEATURE:
<223> OTHER INFORMATION: Synthetic

<400> SEQUENCE: 136
ccgttttttt tttttaaccg att                                              23

<210> SEQ ID NO 137
<211> LENGTH: 23
<212> TYPE: DNA
<213> ORGANISM: Artificial Sequence
<220> FEATURE:
<223> OTHER INFORMATION: Synthetic

<400> SEQUENCE: 137
ccgttttttt tttttcttcc agt                                              23

<210> SEQ ID NO 138
<211> LENGTH: 23
<212> TYPE: DNA
<213> ORGANISM: Artificial Sequence
<220> FEATURE:
<223> OTHER INFORMATION: Synthetic

<400> SEQUENCE: 138
ccgttttttt tttttagcta tgc                                              23

<210> SEQ ID NO 139
<211> LENGTH: 23
<212> TYPE: DNA
<213> ORGANISM: Artificial Sequence
<220> FEATURE:
<223> OTHER INFORMATION: Synthetic

<400> SEQUENCE: 139
ccgttttttt tttttacggg tgc                                              23

<210> SEQ ID NO 140
<211> LENGTH: 22
<212> TYPE: DNA
<213> ORGANISM: Artificial Sequence
<220> FEATURE:
<223> OTHER INFORMATION: Synthetic
```

```
<400> SEQUENCE: 140 cgttttttt ttttgagccc tg                                           22

<210> SEQ ID NO 141
<211> LENGTH: 23
<212> TYPE: DNA
<213> ORGANISM: Artificial Sequence
<220> FEATURE:
<223> OTHER INFORMATION: Synthetic

<400> SEQUENCE: 141
ccgttttttt tttttacgct caa                                         23

<210> SEQ ID NO 142
<211> LENGTH: 23
<212> TYPE: DNA
<213> ORGANISM: Artificial Sequence
<220> FEATURE:
<223> OTHER INFORMATION: Synthetic

<400> SEQUENCE: 142
ccgttttttt tttttcacgc gag                                         23

<210> SEQ ID NO 143
<211> LENGTH: 23
<212> TYPE: DNA
<213> ORGANISM: Artificial Sequence
<220> FEATURE:
<223> OTHER INFORMATION: Synthetic

<400> SEQUENCE: 143
ccgttttttt tttttccttc tga                                         23

<210> SEQ ID NO 144
<211> LENGTH: 22
<212> TYPE: DNA
<213> ORGANISM: Artificial Sequence
<220> FEATURE:
<223> OTHER INFORMATION: Synthetic

<400> SEQUENCE: 144 cgttttttt ttttcaacgg ga                                           22

<210> SEQ ID NO 145
<211> LENGTH: 24
<212> TYPE: DNA
<213> ORGANISM: Artificial Sequence
<220> FEATURE:
<223> OTHER INFORMATION: Synthetic

<400> SEQUENCE: 145 tccgttttttt tttttactc agta                                        24

<210> SEQ ID NO 146
<211> LENGTH: 23
<212> TYPE: DNA
<213> ORGANISM: Artificial Sequence
<220> FEATURE:
<223> OTHER INFORMATION: Synthetic

<400> SEQUENCE: 146
ccgttttttt tttttacaaa cca                                         23

<210> SEQ ID NO 147
<211> LENGTH: 23
```

```
<212> TYPE: DNA
<213> ORGANISM: Artificial Sequence
<220> FEATURE:
<223> OTHER INFORMATION: Synthetic

<400> SEQUENCE: 147 ccgtttttttt tttttacttt cgg                                            23

<210> SEQ ID NO 148
<211> LENGTH: 22
<212> TYPE: DNA
<213> ORGANISM: Artificial Sequence
<220> FEATURE:
<223> OTHER INFORMATION: Synthetic

<400> SEQUENCE: 148
cgtttttttt ttttggaggc cg                                              22

<210> SEQ ID NO 149
<211> LENGTH: 18
<212> TYPE: DNA
<213> ORGANISM: Artificial Sequence
<220> FEATURE:
<223> OTHER INFORMATION: Synthetic

<400> SEQUENCE: 149
aatatggaac gcttcacg                                                   18

<210> SEQ ID NO 150
<211> LENGTH: 28
<212> TYPE: DNA
<213> ORGANISM: Artificial Sequence
<220> FEATURE:
<223> OTHER INFORMATION: Synthetic

<400> SEQUENCE: 150
cagtcatttg gctgattggt acgtctgt                                        28

<210> SEQ ID NO 151
<211> LENGTH: 23
<212> TYPE: DNA
<213> ORGANISM: Artificial Sequence
<220> FEATURE:
<223> OTHER INFORMATION: Synthetic

<400> SEQUENCE: 151 ccgtttttttt tttttctacc cac                                            23

<210> SEQ ID NO 152
<211> LENGTH: 22
<212> TYPE: RNA
<213> ORGANISM: Homo Sapiens

<400> SEQUENCE: 152
agagguagua gguugcauag uu                                              22

<210> SEQ ID NO 153
<211> LENGTH: 22
<212> TYPE: RNA
<213> ORGANISM: Homo Sapiens

<400> SEQUENCE: 153
ugagguagga gguuguauag uu                                              22

<210> SEQ ID NO 154
```

```
<211> LENGTH: 22
<212> TYPE: RNA
<213> ORGANISM: Homo Sapiens

<400> SEQUENCE: 154
ugagguagua aguuguauug uu                                          22

<210> SEQ ID NO 155
<211> LENGTH: 22
<212> TYPE: RNA
<213> ORGANISM: Homo Sapiens

<400> SEQUENCE: 155
ugagguagua gguuguauag uu                                          22

<210> SEQ ID NO 156
<211> LENGTH: 22
<212> TYPE: RNA
<213> ORGANISM: Homo Sapiens

<400> SEQUENCE: 156
ugagguagua gguuguaugg uu                                          22

<210> SEQ ID NO 157
<211> LENGTH: 22
<212> TYPE: RNA
<213> ORGANISM: Homo Sapiens

<400> SEQUENCE: 157
ugagguagua guuguacag uu                                           22

<210> SEQ ID NO 158
<211> LENGTH: 22
<212> TYPE: RNA
<213> ORGANISM: Homo Sapiens

<400> SEQUENCE: 158
ugagguagua guugugcug uu                                           22

<210> SEQ ID NO 159
<211> LENGTH: 22
<212> TYPE: RNA
<213> ORGANISM: Homo Sapiens

<400> SEQUENCE: 159
caaagugccu cccuuuagag ug                                          22

<210> SEQ ID NO 160
<211> LENGTH: 23
<212> TYPE: RNA
<213> ORGANISM: Homo Sapiens

<400> SEQUENCE: 160
caaagugcuc auagugcagg uag                                         23

<210> SEQ ID NO 161
<211> LENGTH: 23
<212> TYPE: RNA
<213> ORGANISM: Homo Sapiens

<400> SEQUENCE: 161
caaagugcug uucgugcagg uag                                         23
```

```
<210> SEQ ID NO 162
<211> LENGTH: 23
<212> TYPE: RNA
<213> ORGANISM: Homo Sapiens

<400> SEQUENCE: 162
caaagugcuu acagucagg uag                                          23

<210> SEQ ID NO 163
<211> LENGTH: 22
<212> TYPE: RNA
<213> ORGANISM: Homo Sapiens

<400> SEQUENCE: 163
gaaagugcuu ccuuuuagag gc                                          22

<210> SEQ ID NO 164
<211> LENGTH: 21
<212> TYPE: RNA
<213> ORGANISM: Homo Sapiens

<400> SEQUENCE: 164
uaaagugcug acagucaga u                                            21

<210> SEQ ID NO 165
<211> LENGTH: 23
<212> TYPE: RNA
<213> ORGANISM: Homo Sapiens

<400> SEQUENCE: 165
uacccuguag aaccgaauuu gug                                         23

<210> SEQ ID NO 166
<211> LENGTH: 21
<212> TYPE: RNA
<213> ORGANISM: Homo Sapiens

<400> SEQUENCE: 166
uaaggcaccc uucugaguag a                                           21

<210> SEQ ID NO 167
<211> LENGTH: 24
<212> TYPE: RNA
<213> ORGANISM: Homo Sapiens

<400> SEQUENCE: 167
ucccugagac ccuuuaaccu guga                                        24

<210> SEQ ID NO 168
<211> LENGTH: 23
<212> TYPE: RNA
<213> ORGANISM: Homo Sapiens

<400> SEQUENCE: 168
cagugcaaua guauugucaa agc                                         23

<210> SEQ ID NO 169
<211> LENGTH: 23
<212> TYPE: RNA
<213> ORGANISM: Homo Sapiens

<400> SEQUENCE: 169
cagugcaaug auauugucaa agc                                         23
```

```
<210> SEQ ID NO 170
<211> LENGTH: 22
<212> TYPE: RNA
<213> ORGANISM: Homo Sapiens

<400> SEQUENCE: 170
cagugcaaug augaaagggc au                                                  22

<210> SEQ ID NO 171
<211> LENGTH: 23
<212> TYPE: RNA
<213> ORGANISM: Homo Sapiens

<400> SEQUENCE: 171
uagugcaaua uugcuuauag ggu                                                 23

<210> SEQ ID NO 172
<211> LENGTH: 22
<212> TYPE: RNA
<213> ORGANISM: Homo Sapiens

<400> SEQUENCE: 172
ucagugcacu acagaacuuu gu                                                  22

<210> SEQ ID NO 173
<211> LENGTH: 22
<212> TYPE: RNA
<213> ORGANISM: Homo Sapiens

<400> SEQUENCE: 173
cagcagcaau ucauguuuug aa                                                  22

<210> SEQ ID NO 174
<211> LENGTH: 21
<212> TYPE: RNA
<213> ORGANISM: Homo Sapiens

<400> SEQUENCE: 174
uagcagcaca gaaauauugg c                                                   21

<210> SEQ ID NO 175
<211> LENGTH: 22
<212> TYPE: RNA
<213> ORGANISM: Homo Sapiens

<400> SEQUENCE: 175
uagcagcaca uaaugguuug ug                                                  22

<210> SEQ ID NO 176
<211> LENGTH: 22
<212> TYPE: RNA
<213> ORGANISM: Homo Sapiens

<400> SEQUENCE: 176
uagcagcacg uaaauauugg cg                                                  22

<210> SEQ ID NO 177
<211> LENGTH: 21
<212> TYPE: RNA
<213> ORGANISM: Homo Sapiens

<400> SEQUENCE: 177
augaccuaug aauugacaga c                                                   21
```

-continued

```
<210> SEQ ID NO 178
<211> LENGTH: 22
<212> TYPE: RNA
<213> ORGANISM: Homo Sapiens

<400> SEQUENCE: 178
aacuggcccu caaagucccg cu                                            22

<210> SEQ ID NO 179
<211> LENGTH: 23
<212> TYPE: RNA
<213> ORGANISM: Homo Sapiens

<400> SEQUENCE: 179
ugugcaaauc uaugcaaaac uga                                           23

<210> SEQ ID NO 180
<211> LENGTH: 22
<212> TYPE: RNA
<213> ORGANISM: Homo Sapiens

<400> SEQUENCE: 180
uaacacuguc ugguaaagau gg                                            22

<210> SEQ ID NO 181
<211> LENGTH: 22
<212> TYPE: RNA
<213> ORGANISM: Homo Sapiens

<400> SEQUENCE: 181
uaauacuguc ugguaaaacc gu                                            22

<210> SEQ ID NO 182
<211> LENGTH: 22
<212> TYPE: RNA
<213> ORGANISM: Homo Sapiens

<400> SEQUENCE: 182
gagcuuauuc auaaaagugc ag                                            22

<210> SEQ ID NO 183
<211> LENGTH: 21
<212> TYPE: RNA
<213> ORGANISM: Homo Sapiens

<400> SEQUENCE: 183
agcuacaucu ggcuacuggg u                                             21

<210> SEQ ID NO 184
<211> LENGTH: 22
<212> TYPE: RNA
<213> ORGANISM: Homo Sapiens

<400> SEQUENCE: 184
aauugcacgg uauccaucug ua                                            22

<210> SEQ ID NO 185
<211> LENGTH: 22
<212> TYPE: RNA
<213> ORGANISM: Homo Sapiens

<400> SEQUENCE: 185
```
aauugcacuu uagcaauggu ga 22

<210> SEQ ID NO 186
<211> LENGTH: 22
<212> TYPE: RNA
<213> ORGANISM: Homo Sapiens

<400> SEQUENCE: 186
uauugcacau uacuaaguug ca 22

<210> SEQ ID NO 187
<211> LENGTH: 22
<212> TYPE: RNA
<213> ORGANISM: Homo Sapiens

<400> SEQUENCE: 187
uauugcacuu gucccggccu gu 22

<210> SEQ ID NO 188
<211> LENGTH: 22
<212> TYPE: RNA
<213> ORGANISM: Homo Sapiens

<400> SEQUENCE: 188
uguaaacauc cccgacugga ag 22

<210> SEQ ID NO 189
<211> LENGTH: 22
<212> TYPE: RNA
<213> ORGANISM: Homo Sapiens

<400> SEQUENCE: 189
uguaaacauc cuacacucag cu 22

<210> SEQ ID NO 190
<211> LENGTH: 23
<212> TYPE: RNA
<213> ORGANISM: Homo Sapiens

<400> SEQUENCE: 190
uguaaacauc cuacacucuc agc 23

<210> SEQ ID NO 191
<211> LENGTH: 22
<212> TYPE: RNA
<213> ORGANISM: Homo Sapiens

<400> SEQUENCE: 191
uguaaacauc cuugacugga ag 22

<210> SEQ ID NO 192
<211> LENGTH: 22
<212> TYPE: RNA
<213> ORGANISM: Homo Sapiens

<400> SEQUENCE: 192
aaagugcuuc ccuuuggacu gu 22

<210> SEQ ID NO 193
<211> LENGTH: 21
<212> TYPE: RNA
<213> ORGANISM: Homo Sapiens

<400> SEQUENCE: 193

```
aaagugcuuc cuuuuagagg g                                        21

<210> SEQ ID NO 194
<211> LENGTH: 22
<212> TYPE: RNA
<213> ORGANISM: Homo Sapiens

<400> SEQUENCE: 194
aaagugcuuc cuuuuagagg gu                                       22

<210> SEQ ID NO 195
<211> LENGTH: 21
<212> TYPE: RNA
<213> ORGANISM: Homo Sapiens

<400> SEQUENCE: 195
aaagugcuuc cuuuuugagg g                                        21

<210> SEQ ID NO 196
<211> LENGTH: 22
<212> TYPE: RNA
<213> ORGANISM: Homo Sapiens

<400> SEQUENCE: 196
aaagugcuuc ucuuuggugg gu                                       22

<210> SEQ ID NO 197
<211> LENGTH: 23
<212> TYPE: RNA
<213> ORGANISM: Homo Sapiens

<400> SEQUENCE: 197
gaagugcuuc gauuuugggg ugu                                      23

<210> SEQ ID NO 198
<211> LENGTH: 17
<212> TYPE: RNA
<213> ORGANISM: Homo Sapiens

<400> SEQUENCE: 198
uaagugcuuc caugcuu                                             17

<210> SEQ ID NO 199
<211> LENGTH: 23
<212> TYPE: RNA
<213> ORGANISM: Homo Sapiens

<400> SEQUENCE: 199
uaagugcuuc cauguuucag ugg                                      23

<210> SEQ ID NO 200
<211> LENGTH: 23
<212> TYPE: RNA
<213> ORGANISM: Homo Sapiens

<400> SEQUENCE: 200
uaagugcuuc cauguuugag ugu                                      23

<210> SEQ ID NO 201
<211> LENGTH: 23
<212> TYPE: RNA
<213> ORGANISM: Homo Sapiens
```

-continued

<400> SEQUENCE: 201
uaagugcuuc cauguuuuag uag                                    23

<210> SEQ ID NO 202
<211> LENGTH: 23
<212> TYPE: RNA
<213> ORGANISM: Homo Sapiens

<400> SEQUENCE: 202
uaagugcuuc cauguuuugg uga                                    23

<210> SEQ ID NO 203
<211> LENGTH: 22
<212> TYPE: RNA
<213> ORGANISM: Homo Sapiens

<400> SEQUENCE: 203
acuggacuua gggucagaag gc                                     22

<210> SEQ ID NO 204
<211> LENGTH: 21
<212> TYPE: RNA
<213> ORGANISM: Homo Sapiens

<400> SEQUENCE: 204
cuauacaauc uacugucuuu c                                      21

<210> SEQ ID NO 205
<211> LENGTH: 22
<212> TYPE: RNA
<213> ORGANISM: Homo Sapiens

<400> SEQUENCE: 205
cuauacaacc uacugccuuc cc                                     22

<210> SEQ ID NO 206
<211> LENGTH: 22
<212> TYPE: RNA
<213> ORGANISM: Homo Sapiens

<400> SEQUENCE: 206
cuauacgacc ugcugccuuu cu                                     22

<210> SEQ ID NO 207
<211> LENGTH: 22
<212> TYPE: RNA
<213> ORGANISM: Homo Sapiens

<400> SEQUENCE: 207
cuauacaauc uauugccuuc cc                                     22

<210> SEQ ID NO 208
<211> LENGTH: 22
<212> TYPE: RNA
<213> ORGANISM: Homo Sapiens

<400> SEQUENCE: 208
cuauacaguc uacugucuuu cc                                     22

<210> SEQ ID NO 209
<211> LENGTH: 22
<212> TYPE: RNA
<213> ORGANISM: Homo Sapiens

```
<400> SEQUENCE: 209
aguuuugcag guuugcauuu ca                                           22

<210> SEQ ID NO 210
<211> LENGTH: 22
<212> TYPE: RNA
<213> ORGANISM: Homo Sapiens

<400> SEQUENCE: 210
acuguaguau gggcacuucc ag                                           22

<210> SEQ ID NO 211
<211> LENGTH: 22
<212> TYPE: RNA
<213> ORGANISM: Homo Sapiens

<400> SEQUENCE: 211
cggguggauc acgaugcaau uu                                           22

<210> SEQ ID NO 212
<211> LENGTH: 22
<212> TYPE: RNA
<213> ORGANISM: Homo Sapiens

<400> SEQUENCE: 212
ggguggggau uuguugcauu ac                                           22

<210> SEQ ID NO 213
<211> LENGTH: 22
<212> TYPE: RNA
<213> ORGANISM: Homo Sapiens

<400> SEQUENCE: 213
cugcaaugua agcacuucuu ac                                           22

<210> SEQ ID NO 214
<211> LENGTH: 23
<212> TYPE: RNA
<213> ORGANISM: Homo Sapiens

<400> SEQUENCE: 214
uaaggugcau cuagugcagu uag                                          23

<210> SEQ ID NO 215
<211> LENGTH: 22
<212> TYPE: RNA
<213> ORGANISM: Homo Sapiens

<400> SEQUENCE: 215
ugcccuaaau gccccuucug gc                                           22

<210> SEQ ID NO 216
<211> LENGTH: 22
<212> TYPE: RNA
<213> ORGANISM: Homo Sapiens

<400> SEQUENCE: 216
caaauucgua ucuaggggaa ua                                           22

<210> SEQ ID NO 217
<211> LENGTH: 22
<212> TYPE: RNA
```

```
<213> ORGANISM: Homo Sapiens

<400> SEQUENCE: 217
acagauucga uucuagggga au                                           22

<210> SEQ ID NO 218
<211> LENGTH: 22
<212> TYPE: RNA
<213> ORGANISM: Homo Sapiens

<400> SEQUENCE: 218
aacgccauua ucacacuaaa ua                                           22

<210> SEQ ID NO 219
<211> LENGTH: 22
<212> TYPE: RNA
<213> ORGANISM: Homo Sapiens

<400> SEQUENCE: 219
cguguucaca gcggaccuug au                                           22

<210> SEQ ID NO 220
<211> LENGTH: 22
<212> TYPE: RNA
<213> ORGANISM: Homo Sapiens

<400> SEQUENCE: 220
acggguuagg cucuugggag cu                                           22

<210> SEQ ID NO 221
<211> LENGTH: 22
<212> TYPE: RNA
<213> ORGANISM: Homo Sapiens

<400> SEQUENCE: 221
ucacaaguca ggcucuuggg ac                                           22

<210> SEQ ID NO 222
<211> LENGTH: 22
<212> TYPE: RNA
<213> ORGANISM: Homo Sapiens

<400> SEQUENCE: 222
aacccguaga uccgaucuug ug                                           22

<210> SEQ ID NO 223
<211> LENGTH: 22
<212> TYPE: RNA
<213> ORGANISM: Homo Sapiens

<400> SEQUENCE: 223
caagcucgcu ucuaugguc ug                                            22

<210> SEQ ID NO 224
<211> LENGTH: 22
<212> TYPE: RNA
<213> ORGANISM: Homo Sapiens

<400> SEQUENCE: 224
aacccguaga uccgaacuug ug                                           22

<210> SEQ ID NO 225
<211> LENGTH: 22
```

```
<212> TYPE: RNA
<213> ORGANISM: Homo Sapiens

<400> SEQUENCE: 225
caagcuugua ucuauaggua ug                                             22

<210> SEQ ID NO 226
<211> LENGTH: 22
<212> TYPE: RNA
<213> ORGANISM: Homo Sapiens

<400> SEQUENCE: 226
uagaguuaca cccugggagu ua                                             22

<210> SEQ ID NO 227
<211> LENGTH: 21
<212> TYPE: RNA
<213> ORGANISM: Homo Sapiens

<400> SEQUENCE: 227
cauuauuacu uuugguacgc g                                              21

<210> SEQ ID NO 228
<211> LENGTH: 22
<212> TYPE: RNA
<213> ORGANISM: Homo Sapiens

<400> SEQUENCE: 228
uucacauugu gcuacugucu gc                                             22

<210> SEQ ID NO 229
<211> LENGTH: 22
<212> TYPE: RNA
<213> ORGANISM: Homo Sapiens

<400> SEQUENCE: 229
gcuacuucac aacaccaggg cc                                             22

<210> SEQ ID NO 230
<211> LENGTH: 22
<212> TYPE: RNA
<213> ORGANISM: Homo Sapiens

<400> SEQUENCE: 230
gcuauuucac gacaccaggg uu                                             22

<210> SEQ ID NO 231
<211> LENGTH: 21
<212> TYPE: RNA
<213> ORGANISM: Homo Sapiens

<400> SEQUENCE: 231
cauaaaguag aaagcacuac u                                              21

<210> SEQ ID NO 232
<211> LENGTH: 22
<212> TYPE: RNA
<213> ORGANISM: Homo Sapiens

<400> SEQUENCE: 232
ggugcagugc ugcaucucug gu                                             22

<210> SEQ ID NO 233
```

```
<211> LENGTH: 23
<212> TYPE: RNA
<213> ORGANISM: Homo Sapiens

<400> SEQUENCE: 233
guccaguuuu cccaggaauc ccu                                              23

<210> SEQ ID NO 234
<211> LENGTH: 22
<212> TYPE: RNA
<213> ORGANISM: Homo Sapiens

<400> SEQUENCE: 234 ggauccugg aaauacuguu cu                                                22

<210> SEQ ID NO 235
<211> LENGTH: 22
<212> TYPE: RNA
<213> ORGANISM: Homo Sapiens

<400> SEQUENCE: 235
ccucugaaau ucaguucuuc ag                                               22

<210> SEQ ID NO 236
<211> LENGTH: 22
<212> TYPE: RNA
<213> ORGANISM: Homo Sapiens

<400> SEQUENCE: 236
ugcccugugg acucaguucu gg                                               22

<210> SEQ ID NO 237
<211> LENGTH: 22
<212> TYPE: RNA
<213> ORGANISM: Homo Sapiens

<400> SEQUENCE: 237
aaguucuguu auacacucag gc                                               22

<210> SEQ ID NO 238
<211> LENGTH: 22
<212> TYPE: RNA
<213> ORGANISM: Homo Sapiens

<400> SEQUENCE: 238
cgaaucauua uuugcugcuc ua                                               22

<210> SEQ ID NO 239
<211> LENGTH: 22
<212> TYPE: RNA
<213> ORGANISM: Homo Sapiens

<400> SEQUENCE: 239
ccaauauuac ugugcugcuu ua                                               22

<210> SEQ ID NO 240
<211> LENGTH: 22
<212> TYPE: RNA
<213> ORGANISM: Homo Sapiens

<400> SEQUENCE: 240
aggggcuggc uuuccucugg uc                                               22
```

```
<210> SEQ ID NO 241
<211> LENGTH: 18
<212> TYPE: RNA
<213> ORGANISM: Homo Sapiens

<400> SEQUENCE: 241
acguuggcuc ugguggug                                               18

<210> SEQ ID NO 242
<211> LENGTH: 22
<212> TYPE: RNA
<213> ORGANISM: Homo Sapiens

<400> SEQUENCE: 242
cugccaauuc cauaggucac ag                                          22

<210> SEQ ID NO 243
<211> LENGTH: 22
<212> TYPE: RNA
<213> ORGANISM: Homo Sapiens

<400> SEQUENCE: 243
uguaacagca acuccaugug ga                                          22

<210> SEQ ID NO 244
<211> LENGTH: 22
<212> TYPE: RNA
<213> ORGANISM: Homo Sapiens

<400> SEQUENCE: 244
ccaguggggc ugcuguuauc ug                                          22

<210> SEQ ID NO 245
<211> LENGTH: 22
<212> TYPE: RNA
<213> ORGANISM: Homo Sapiens

<400> SEQUENCE: 245
ugggucuuug cgggcgagau ga                                          22

<210> SEQ ID NO 246
<211> LENGTH: 22
<212> TYPE: RNA
<213> ORGANISM: Homo Sapiens

<400> SEQUENCE: 246
uaaugccccu aaaaauccuu au                                          22

<210> SEQ ID NO 247
<211> LENGTH: 22
<212> TYPE: RNA
<213> ORGANISM: Homo Sapiens

<400> SEQUENCE: 247
aguuuugcau aguugcacua ca                                          22

<210> SEQ ID NO 248
<211> LENGTH: 23
<212> TYPE: RNA
<213> ORGANISM: Homo Sapiens

<400> SEQUENCE: 248
uaaggugcau cuagugcaga uag                                         23
```

```
<210> SEQ ID NO 249
<211> LENGTH: 23
<212> TYPE: RNA
<213> ORGANISM: Homo Sapiens

<400> SEQUENCE: 249
acugcccuaa gugcuccuuc ugg                                              23

<210> SEQ ID NO 250
<211> LENGTH: 22
<212> TYPE: RNA
<213> ORGANISM: Homo Sapiens

<400> SEQUENCE: 250
acugcaguga aggcacuugu ag                                               22

<210> SEQ ID NO 251
<211> LENGTH: 22
<212> TYPE: RNA
<213> ORGANISM: Homo Sapiens

<400> SEQUENCE: 251
acugcauuau gagcacuuaa ag                                               22

<210> SEQ ID NO 252
<211> LENGTH: 23
<212> TYPE: RNA
<213> ORGANISM: Homo Sapiens

<400> SEQUENCE: 252
agguugggau cgguugcaau gcu                                              23

<210> SEQ ID NO 253
<211> LENGTH: 23
<212> TYPE: RNA
<213> ORGANISM: Homo Sapiens

<400> SEQUENCE: 253
aguuuugcag guuugcaucc agc                                              23

<210> SEQ ID NO 254
<211> LENGTH: 22
<212> TYPE: RNA
<213> ORGANISM: Homo Sapiens

<400> SEQUENCE: 254
caucuuacug ggcagcauug ga                                               22

<210> SEQ ID NO 255
<211> LENGTH: 22
<212> TYPE: RNA
<213> ORGANISM: Homo Sapiens

<400> SEQUENCE: 255
caucuuaccg gacagugcug ga                                               22

<210> SEQ ID NO 256
<211> LENGTH: 22
<212> TYPE: RNA
<213> ORGANISM: Homo Sapiens

<400> SEQUENCE: 256
cgucuuaccc agcaguguuu gg                                               22
```

<210> SEQ ID NO 257
<211> LENGTH: 22
<212> TYPE: RNA
<213> ORGANISM: Homo Sapiens

<400> SEQUENCE: 257
caucuuccag uacaguguug ga                                              22

<210> SEQ ID NO 258
<211> LENGTH: 21
<212> TYPE: RNA
<213> ORGANISM: Homo Sapiens

<400> SEQUENCE: 258
caacaccagu cgaugggcug u                                               21

<210> SEQ ID NO 259
<211> LENGTH: 22
<212> TYPE: RNA
<213> ORGANISM: Homo Sapiens

<400> SEQUENCE: 259
accuggcaua caauguagau uu                                              22

<210> SEQ ID NO 260
<211> LENGTH: 22
<212> TYPE: RNA
<213> ORGANISM: Homo Sapiens

<400> SEQUENCE: 260
cucaguagcc aguguagauc cu                                              22

<210> SEQ ID NO 261
<211> LENGTH: 21
<212> TYPE: RNA
<213> ORGANISM: Homo Sapiens

<400> SEQUENCE: 261
aggcggagac uugggcaauu g                                               21

<210> SEQ ID NO 262
<211> LENGTH: 22
<212> TYPE: RNA
<213> ORGANISM: Homo Sapiens

<400> SEQUENCE: 262
acugcugagc uagcacuucc cg                                              22

<210> SEQ ID NO 263
<211> LENGTH: 22
<212> TYPE: RNA
<213> ORGANISM: Homo Sapiens

<400> SEQUENCE: 263
ccgcacugug gguacuugcu gc                                              22

<210> SEQ ID NO 264
<211> LENGTH: 22
<212> TYPE: RNA
<213> ORGANISM: Homo Sapiens

<400> SEQUENCE: 264

```
acugauuucu uuuggguguuc ag                                          22

<210> SEQ ID NO 265
<211> LENGTH: 24
<212> TYPE: RNA
<213> ORGANISM: Homo Sapiens

<400> SEQUENCE: 265
gcugguuuca uauggugguu uaga                                         24

<210> SEQ ID NO 266
<211> LENGTH: 22
<212> TYPE: RNA
<213> ORGANISM: Homo Sapiens

<400> SEQUENCE: 266
cugguuucac augguggcuu ag                                           22

<210> SEQ ID NO 267
<211> LENGTH: 22
<212> TYPE: RNA
<213> ORGANISM: Homo Sapiens

<400> SEQUENCE: 267
ugaccgauuu cuccuggugu uc                                           22

<210> SEQ ID NO 268
<211> LENGTH: 22
<212> TYPE: RNA
<213> ORGANISM: Homo Sapiens

<400> SEQUENCE: 268
cuuucagucg gauguuugca gc                                           22

<210> SEQ ID NO 269
<211> LENGTH: 22
<212> TYPE: RNA
<213> ORGANISM: Homo Sapiens

<400> SEQUENCE: 269
cugggagaag gcuguuuacu cu                                           22

<210> SEQ ID NO 270
<211> LENGTH: 22
<212> TYPE: RNA
<213> ORGANISM: Homo Sapiens

<400> SEQUENCE: 270
ugcuaugcca acauauugcc au                                           22

<210> SEQ ID NO 271
<211> LENGTH: 21
<212> TYPE: RNA
<213> ORGANISM: Homo Sapiens

<400> SEQUENCE: 271
aggggugcua ucugugauug a                                            21

<210> SEQ ID NO 272
<211> LENGTH: 23
<212> TYPE: RNA
<213> ORGANISM: Homo Sapiens

<400> SEQUENCE: 272
```

-continued aagugccgcc aucuuuugag ugu                      23

<210> SEQ ID NO 273
<211> LENGTH: 20
<212> TYPE: RNA
<213> ORGANISM: Homo Sapiens

<400> SEQUENCE: 273
acucaaacug uggggggcacu                         20

<210> SEQ ID NO 274
<211> LENGTH: 22
<212> TYPE: RNA
<213> ORGANISM: Homo Sapiens

<400> SEQUENCE: 274
acucaaaaug ggggcgcuuu cc                       22

<210> SEQ ID NO 275
<211> LENGTH: 22
<212> TYPE: RNA
<213> ORGANISM: Homo Sapiens

<400> SEQUENCE: 275
cuccugacuc cagguccugu gu                       22

<210> SEQ ID NO 276
<211> LENGTH: 22
<212> TYPE: RNA
<213> ORGANISM: Homo Sapiens

<400> SEQUENCE: 276
aucgggaaug ucguguccgc cc                       22

<210> SEQ ID NO 277
<211> LENGTH: 23
<212> TYPE: RNA
<213> ORGANISM: Homo Sapiens

<400> SEQUENCE: 277
caacggaauc ccaaaagcag cug                      23

<210> SEQ ID NO 278
<211> LENGTH: 22
<212> TYPE: RNA
<213> ORGANISM: Homo Sapiens

<400> SEQUENCE: 278
gcugcgcuug gauuucgucc cc                       22

<210> SEQ ID NO 279
<211> LENGTH: 20
<212> TYPE: RNA
<213> ORGANISM: Homo Sapiens

<400> SEQUENCE: 279
uacaguauag augauguacu                          20

<210> SEQ ID NO 280
<211> LENGTH: 22
<212> TYPE: RNA
<213> ORGANISM: Homo Sapiens

```
<400> SEQUENCE: 280
ggauaucauc auauacugua ag                                        22

<210> SEQ ID NO 281
<211> LENGTH: 22
<212> TYPE: RNA
<213> ORGANISM: Homo Sapiens

<400> SEQUENCE: 281
ccaauauugg cugugcugcu cc                                        22

<210> SEQ ID NO 282
<211> LENGTH: 22
<212> TYPE: RNA
<213> ORGANISM: Homo Sapiens

<400> SEQUENCE: 282
caaaccacac uguggguguua ga                                       22

<210> SEQ ID NO 283
<211> LENGTH: 23
<212> TYPE: RNA
<213> ORGANISM: Homo Sapiens

<400> SEQUENCE: 283
ucuuugguua ucuagcugua uga                                       23

<210> SEQ ID NO 284
<211> LENGTH: 22
<212> TYPE: RNA
<213> ORGANISM: Homo Sapiens

<400> SEQUENCE: 284
agggacggga cgcggugcag ug                                        22

<210> SEQ ID NO 285
<211> LENGTH: 18
<212> TYPE: RNA
<213> ORGANISM: Homo Sapiens

<400> SEQUENCE: 285
ugaggcagua gauugaau                                             18

<210> SEQ ID NO 286
<211> LENGTH: 23
<212> TYPE: RNA
<213> ORGANISM: Homo Sapiens

<400> SEQUENCE: 286
uacccuguag aaccgaauuu gug                                       23

<210> SEQ ID NO 287
<211> LENGTH: 46
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (46)..(46)
<223> OTHER INFORMATION: n is a, c, g or t
<220> FEATURE:
<221> NAME/KEY: misc_feature
<222> LOCATION: (45)..(45)
<223> OTHER INFORMATION: v is a, c or g
```

```
<400> SEQUENCE: 287
gcgagcacag aattaatacg actcactatc ggttttttt ttttvn          46

<210> SEQ ID NO 288
<211> LENGTH: 22
<212> TYPE: DNA
<213> ORGANISM: Artificial Sequence
<220> FEATURE:
<223> OTHER INFORMATION: Synthetic

<400> SEQUENCE: 288
gcgagcacag aattaatacg ac                                  22
```

GENE EXPRESSION SIGNATURE FOR CLASSIFICATION OF TISSUE OF ORIGIN OF TUMOR SAMPLES

CROSS REFERENCE TO RELATED APPLICATIONS

This application is a Continuation in part of International Patent Application PCT/IL2009/001212, filed Dec. 23, 2009, which claims priority from 61/140,642, filed Dec. 24, 2008 and is a Continuation in Part of Ser. No. 12/532,940, filed Sep. 24, 2009, which is a U.S. National Stage of International Patent Application PCT/IL2008/000396, filed Mar. 20, 2008, which claims priority from 60/907,266, filed Mar. 27, 2007, 60/929,244, filed Jun. 19, 2007 and 61/024,565 filed Jan. 30, 2008, the contents of which are incorporated herein by reference.

FIELD OF THE INVENTION

The present invention relates to methods for classification of cancers and the identification of their tissue of origin. Specifically the invention relates to microRNA molecules associated with specific cancers, as well as various nucleic acid molecules relating thereto or derived therefrom.

BACKGROUND OF THE INVENTION microRNAs (miRs, miRNAs) are a novel class of non-coding, regulatory RNA genes[1-3] which are involved in oncogenesis[4] and show remarkable tissue-specificity[5-7]. They have emerged as highly tissue-specific biomarkers[2,5,6] postulated to play important roles in encoding developmental decisions of differentiation. Various studies have tied microRNAs to the development of specific malignancies[4]. MicroRNAs are also stable in tissue, stored frozen or as formalin-fixed, paraffin-embedded (FFPE) samples, and in serum.

Hundreds of thousands of patients in the U.S. are diagnosed each year with a cancer that has already metastasized, without a clearly identified primary site. Oncologists and pathologists are constantly faced with a diagnostic dilemma when trying to identify the primary origin of a patient's metastasis. As metastases need to be treated according to their primary origin, accurate identification of the metastases' primary origin can be critical for determining appropriate treatment.

Once a metastatic tumor is found, the patient may undergo a wide range of costly, time consuming, and at times inefficient tests, including physical examination of the patient, histopathology analysis of the biopsy, imaging methods such as chest X-ray, CT and PET scans, in order to identify the primary origin of the metastasis.

Metastatic cancer of unknown primary (CUP) accounts for 3-5% of all new cancer cases, and as a group is usually a very aggressive disease with a poor prognosis[10]. The concept of CUP comes from the limitation of present methods to identify cancer origin, despite an often complicated and costly process which can significantly delay proper treatment of such patients. Recent studies revealed a high degree of variation in clinical management, in the absence of evidence based treatment for CUP[11]. Many protocols were evaluated[12] but have shown relatively small benefit[13]. Determining tumor tissue of origin is thus an important clinical application of molecular diagnostics[9].

Molecular classification studies for tumor tissue origin[14-17] have generally used classification algorithms that did not utilize domain-specific knowledge: tissues were treated as a-priori equivalents, ignoring underlying similarities between tissue types with a common developmental origin in embryogenesis. An exception of note is the study by Shedden and co-workers[18], that was based on a pathology classification tree. These studies used machine-learning methods that average effects of biological features (e.g., mRNA expression levels), an approach which is more amenable to automated processing but does not use or generate mechanistic insights.

Various markers have been proposed to indicate specific types of cancers and tumor tissue of origin. However, the diagnostic accuracy of tumor markers has not yet been defined. There is thus a need for a more efficient and effective method for diagnosing and classifying specific types of cancers.

SUMMARY OF THE INVENTION

The present invention provides specific nucleic acid sequences for use in the identification, classification and diagnosis of specific cancers and tumor tissue of origin. The nucleic acid sequences can also be used as prognostic markers for prognostic evaluation and determination of appropriate treatment of a subject based on the abundance of the nucleic acid sequences in a biological sample. The present invention further provides a method for accurate identification of tumor tissue origin.

The invention is based in part on the development of a microRNA-based classifier for tumor classification. microRNA expression levels were measured in 903 paraffin-embedded samples from 26 different tumor classes, corresponding to 18 distinct tissues and organs, including primary and metastatic tumors. microRNA microarray, of the samples as well as qRT-PCR data, were used to construct a classifier, based on 48 tissue-specific microRNAs, each linked to specific differential-diagnosis roles.

The overall sensitivity of the independent blinded test in identifying the tumor tissue of origin is 84%, with 97% specificity. High confidence predictions reach 90% sensitivity with 99% specificity.

The findings demonstrate the utility of microRNA as novel biomarkers for the tissue of origin of a metastatic tumor. The classifier has wide biological as well as diagnostic applications.

According to a first aspect, the present invention provides a method of identifying a tissue of origin of a biological sample, the method comprising: obtaining a biological sample from a subject; determining an expression profile of individual nucleic acids for a predetermined set of microRNAs; and classifying the tissue of origin for said sample by a classifier. According to one embodiment, said classifier is a decision tree model.

According to another aspect, the present invention provides a method of classifying a tissue of origin of a biological sample, the method comprising: obtaining a biological sample from a subject; determining an expression profile in said sample of nucleic acid sequences selected from the group consisting of SEQ ID NOS: 1-49, or a sequence having at least about 80% identity thereto; and comparing said expression profile to a reference expression profile by using a classifier algorithm; whereby the expression of any of said nucleic acid sequences or combinations thereof allows the identification of the tissue of origin of said sample.

According to one embodiment, said classifier algorithm is a decision tree classifier, logistic regression classifier, linear regression classifier, nearest neighbor classifier (including K nearest neighbors), neural network classifier, Gaussian mixture model (GMM) classifier and Support Vector Machine (SVM) classifier, nearest centroid classifier, random forest classifier or any boosting or bootstrap aggregating (bagging) of those classifiers.

According to certain embodiments, said tissue is selected from the group consisting of liver, lung, bladder, prostate, breast, colon, ovary, testis, stomach, thyroid, pancreas, brain, head and neck, kidney, melanocytes, thymus, biliary tract and esophagus.

According to some embodiments said biological sample is a cancerous sample.

According to another aspect, the present invention provides a method of classifying a cancer, the method comprising: obtaining a biological sample from a subject; measuring the relative abundance in said sample of nucleic acid sequences selected from the group consisting of SEQ ID NOS: 1-49 or a sequence having at least about 80% identity thereto; and comparing said obtained measurement to reference values representing abundance of said nucleic acid sequences by using a classifier algorithm; whereby the relative abundance of said nucleic acid sequences allows the classification of said cancer.

According to some embodiments, said reference values are predetermined thresholds.

According to one embodiment, said sample is obtained from a subject with a metastatic cancer. According to another embodiment, said sample is obtained from a subject with cancer of unknown primary (CUP). According to a further embodiment, said sample is obtained from a subject with a primary cancer. According to still another embodiment, said sample is a tumor of unidentified origin, a metastatic tumor or a primary tumor.

According to certain embodiments, said cancer is selected from the group consisting of liver cancer, biliary tract cancer, lung cancer, bladder cancer, prostate cancer, breast cancer, colon cancer, ovarian cancer, testicular cancer, stomach cancer, thyroid cancer, pancreas cancer, brain cancer, head and neck cancer, kidney cancer, melanoma, thymus cancer and esophagus cancer.

According to some embodiments, said lung cancer is selected from the group consisting of lung carcinoid, lung small cell carcinoma, lung adenocarcinoma, and lung squamous cell carcinoma.

According to some embodiments, said brain cancer is selected from the group consisting of brain astrocytoma and brain oligodendroglioma.

According to some embodiments, said thyroid cancer is selected from the group consisting of thyroid follicular, thyroid papillary and thyroid medullary cancer.

According to some embodiments, said ovarian cancer is selected from the group consisting of ovarian endometrioid and ovarian serous cancer.

According to some embodiments, said testicular cancer is selected from the group consisting of testicular non-seminoma and testicular seminoma.

According to some embodiments, said esophagus cancer is selected from the group consisting of esophagus adenocarcinoma and esophagus squamous cell carcinoma.

According to some embodiments, said head and neck cancer is selected from the group consisting of larynx carcinoma, pharynx carcinoma and nose carcinoma.

According to some embodiments, said biliary tract cancer is selected from the group consisting of cholangiocarcinoma and gallbladder adenocarcinoma.

According to other embodiments, said biological sample is selected from the group consisting of bodily fluid, a cell line, a tissue sample, a biopsy sample, a needle biopsy sample, a surgically removed sample, and a sample obtained by tissue-sampling procedures. According to some embodiments the biological sample is a fine needle aspiration (FNA) sample. According to some embodiments, said tissue is a fresh, frozen, fixed, wax-embedded or formalin-fixed paraffin-embedded (FFPE) tissue.

The classification method of the present invention comprises the use of at least one classifier algorithm, said classifier algorithm is selected from the group consisting of decision tree classifier, logistic regression classifier, linear regression classifier, nearest neighbor classifier (including K nearest neighbors), neural network classifier, Gaussian mixture model (GMM) classifier and Support Vector Machine (SVM) classifier, nearest centroid classifier, random forest classifier or any boosting or bootstrap aggregating (bagging) of those classifiers.

The classifier may use a decision tree structure (including binary tree) or a voting (including weighted voting) scheme to compare the classification of one or more classifier algorithms in order to reach a unified or majority decision.

The invention further provides a method for classifying a cancer of liver origin, the method comprising measuring the relative abundance of a nucleic acid sequence selected from the group consisting of SEQ ID NOS: 6, 9, 25, 26, or a sequence having at least about 80% identity thereto in a sample obtained from a subject; wherein the abundance of said nucleic acid sequence is indicative of a cancer of liver origin.

The invention further provides a method for classifying a cancer of testicular origin, the method comprising measuring the relative abundance of a nucleic acid sequence selected from the group consisting of SEQ ID NOS: 6, 26, 41, or a sequence having at least about 80% identity thereto in a sample obtained from a subject; wherein the abundance of said nucleic acid sequence is indicative of a cancer of testicular origin.

The invention further provides a method for classifying a cancer of testicular seminoma origin, the method comprising measuring the relative abundance of a nucleic acid sequence selected from the group consisting of SEQ ID NOS: 6, 26, 31, 41, 45, 48 or a sequence having at least about 80% identity thereto in a sample obtained from a subject; wherein the abundance of said nucleic acid sequence is indicative of a cancer of testicular seminoma origin.

The invention further provides a method for classifying a cancer of melanoma origin, the method comprising measuring the relative abundance of a nucleic acid sequence selected from the group consisting of SEQ ID NOS: 6, 15, 17, 26, 41, 46, or a sequence having at least about 80% identity thereto in a sample obtained from a subject; wherein the abundance of said nucleic acid sequence is indicative of a cancer of melanoma origin.

The invention further provides a method for classifying a cancer of kidney origin, the method comprising measuring the relative abundance of a nucleic acid sequence selected from the group consisting of SEQ ID NOS: 6, 7, 15, 17, 26, 41, 46, 47, or a sequence having at least about 80% identity thereto in a sample obtained from a subject; wherein the abundance of said nucleic acid sequence is indicative of a cancer of kidney origin.

The invention further provides a method for classifying a cancer of brain origin, the method comprising measuring the relative abundance of a nucleic acid sequence selected from the group consisting of SEQ ID NOS: 6, 7, 15, 17, 26, 41, 46, 47, or a sequence having at least about 80% identity thereto in a sample obtained from a subject; wherein the abundance of said nucleic acid sequence is indicative of a cancer of brain origin.

The invention further provides a method for classifying a cancer of brain astrocytoma origin, the method comprising measuring the relative abundance of a nucleic acid sequence selected from the group consisting of SEQ ID NOS: 6, 7, 10, 15, 17, 26, 41, 46, 47, or a sequence having at least about 80% identity thereto in said sample; wherein the abundance of said nucleic acid sequence is indicative of a cancer of brain astrocytoma origin.

The invention further provides a method for classifying a cancer of brain oligodendroglioma origin, the method comprising measuring the relative abundance of a nucleic acid sequence selected from the group consisting of SEQ ID NOS: 6, 7, 10, 15, 17, 26, 41, 46, 47, or a sequence having at least about 80% identity thereto in said sample; wherein the abundance of said nucleic acid sequence is indicative of a cancer of brain oligodendroglioma origin.

The invention further provides a method for classifying a cancer of thyroid medullary origin, the method comprising measuring the relative abundance of a nucleic acid sequence selected from the group consisting of SEQ ID NOS: 6, 17-19, 24, 26, 32, 41, 42, or a sequence having at least about 80% identity thereto in a sample obtained from a subject; wherein the abundance of said nucleic acid sequence is indicative of a cancer of thyroid medullary origin.

The invention further provides a method for classifying a cancer of lung carcinoid origin, the method comprising measuring the relative abundance of a nucleic acid sequence selected from the group consisting of SEQ ID NOS: 3, 6, 17-19, 24, 26, 32, 36, 41, 42, or a sequence having at least about 80% identity thereto in a sample obtained from a subject; wherein the abundance of said nucleic acid sequence is indicative of a cancer of lung carcinoid origin.

The invention further provides a method for classifying a cancer of lung small cell carcinoma origin, the method comprising measuring the relative abundance of a nucleic acid sequence selected from the group consisting of SEQ ID NOS: 3, 6, 17-19, 24, 26, 32, 36, 41, 42, or a sequence having at least about 80% identity thereto in a sample obtained from a subject; wherein the abundance of said nucleic acid sequence is indicative of a cancer of lung small cell carcinoma origin.

The invention further provides a method for classifying a cancer of colon origin, the method comprising measuring the relative abundance of a nucleic acid sequence selected from the group consisting of SEQ ID NOS: 1, 3, 4, 6, 17-19, 21, 26, 29, 34, 37, 41, 42, 48, or a sequence having at least about 80% identity thereto in a sample obtained from a subject; wherein the abundance of said nucleic acid sequence is indicative of a cancer of colon origin.

The invention further provides a method for classifying a cancer of stomach origin, the method comprising measuring the relative abundance of a nucleic acid sequence selected from the group consisting of SEQ ID NOS: 1, 3, 4, 6, 17-19, 21, 26, 29, 34, 37, 41, 42, 48, or a sequence having at least about 80% identity thereto in a sample obtained from a subject; wherein the abundance of said nucleic acid sequence is indicative of a cancer of stomach origin.

The invention further provides a method for classifying a cancer of pancreas origin, the method comprising measuring the relative abundance of a nucleic acid sequence selected from the group consisting of SEQ ID NOS: 1, 3, 6, 17-19, 21, 26, 28, 29, 33, 37, 41, 42, or a sequence having at least about 80% identity thereto in a sample obtained from a subject; wherein the abundance of said nucleic acid sequence is indicative of a cancer of pancreas origin.

The invention further provides a method for classifying a cancer of biliary tract origin, the method comprising measuring the relative abundance of a nucleic acid sequence selected from the group consisting of SEQ ID NOS: 1, 3, 6, 9, 17-19, 21, 25, 26, 28, 29, 33, 37, 41, 42, or a sequence having at least about 80% identity thereto in a sample obtained from a subject; wherein the abundance of said nucleic acid sequence is indicative of a cancer of biliary tract origin.

The invention further provides a method for classifying a cancer of prostate origin, the method comprising measuring the relative abundance of a nucleic acid sequence selected from the group consisting of SEQ ID NOS: 3, 6, 17-21, 26, 41, 42, or a sequence having at least about 80% identity thereto in a sample obtained from a subject; wherein the abundance of said nucleic acid sequence is indicative of a cancer of prostate origin.

The invention further provides a method for classifying a cancer of ovarian origin, the method comprising measuring the relative abundance of a nucleic acid sequence selected from the group consisting of SEQ ID NOS: 3, 5, 6, 11, 17-21, 26, 30, 41, 42, or a sequence having at least about 80% identity thereto in a sample obtained from a subject; wherein the abundance of said nucleic acid sequence is indicative of a cancer of ovarian origin.

The invention further provides a method for classifying a cancer of ovarian endometrioid origin, the method comprising measuring the relative abundance of a nucleic acid sequence selected from the group consisting of SEQ ID NOS: 2, 3, 5, 6, 11, 17-22, 26, 30, 41, 42, or a sequence having at least about 80% identity thereto in a sample obtained from a subject; wherein the abundance of said nucleic acid sequence is indicative of a cancer of ovarian endometrioid origin.

The invention further provides a method for classifying a cancer of ovarian serous origin, the method comprising measuring the relative abundance of a nucleic acid sequence selected from the group consisting of SEQ ID NOS: 2, 3, 5, 6, 11, 17-22, 26, 30, 41, 42, or a sequence having at least about 80% identity thereto in a sample obtained from a subject; wherein the abundance of said nucleic acid sequence is indicative of a cancer of ovarian serous origin.

The invention further provides a method for classifying a cancer of breast origin, the method comprising measuring the relative abundance of a nucleic acid sequence selected from the group consisting of SEQ ID NOS: 3, 5, 6, 11, 17-22, 26, 30, 39, 41, 42, or a sequence having at least about 80% identity thereto in a sample obtained from a subject; wherein the abundance of said nucleic acid sequence is indicative of a cancer of breast origin.

The invention further provides a method for classifying a cancer of lung adenocarcinoma origin, the method comprising measuring the relative abundance of a nucleic acid sequence selected from the group consisting of SEQ ID NOS: 3, 5, 6, 8, 11, 16-22, 26, 27, 30, 37, 39, 41, 42, or a sequence having at least about 80% identity thereto in a sample obtained from a subject; wherein the abundance of said nucleic acid sequence is indicative of a cancer of lung adenocarcinoma origin.

The invention further provides a method for classifying a cancer of papillary thyroid origin, the method comprising measuring the relative abundance of a nucleic acid sequence selected from the group consisting of SEQ ID NOS: 3, 5, 6, 8, 11, 16-22, 26, 27, 29, 30, 37-39, 41, 42, or a sequence having at least about 80% identity thereto in a sample obtained from a subject; wherein the abundance of said nucleic acid sequence is indicative of a cancer of papillary thyroid origin.

The invention further provides a method for classifying a cancer of follicular thyroid origin, the method comprising measuring the relative abundance of a nucleic acid sequence selected from the group consisting of SEQ ID NOS: 3, 5, 6, 8, 11, 16-22, 26, 27, 29, 30, 37-39, 41, 42, or a sequence having at least about 80% identity thereto in said sample; wherein the abundance of said nucleic acid sequence is indicative of a cancer of follicular thyroid origin.

The invention further provides a method for classifying a cancer of thymus origin, the method comprising measuring the relative abundance of a nucleic acid sequence selected from the group consisting of SEQ ID NOS: 3, 5, 6, 11, 16-22, 26, 27, 29, 30, 35, 39, 41, 42, or a sequence having at least about 80% identity thereto in a sample obtained from a subject; wherein the abundance of said nucleic acid sequence is indicative of a cancer of thymus origin.

The invention further provides a method for classifying a cancer of bladder origin, the method comprising measuring the relative abundance of a nucleic acid sequence selected from the group consisting of SEQ ID NOS: 3-6, 11, 16-22, 26, 27, 29, 30, 35, 39, 41, 42, 44, or a sequence having at least about 80% identity thereto in a sample obtained from a subject; wherein the abundance of said nucleic acid sequence is indicative of a cancer of bladder origin.

The invention further provides a method for classifying a cancer of lung sq uamous origin, the method comprising measuring the relative abundance of a nucleic acid sequence selected from the group consisting of SEQ ID NOS: 3-6, 11, 16-23, 26, 27, 29, 30, 32, 35, 39, 41, 42, 44, or a sequence having at least about 80% identity thereto in a sample obtained from a subject; wherein the abundance of said nucleic acid sequence is indicative of a cancer of lung squamous origin.

The invention further provides a method for classifying a cancer of head and neck origin, the method comprising measuring the relative abundance of a nucleic acid sequence selected from the group consisting of SEQ ID NOS: 3-6, 11, 14, 16-23, 26, 27, 29, 30, 32, 35, 37, 39, 41, 42, 44, 45, or a sequence having at least about 80% identity thereto in a sample obtained from a subject; wherein the abundance of said nucleic acid sequence is indicative of a cancer of head and neck origin.

The invention further provides a method for classifying a cancer of esophagus origin, the method comprising measuring the relative abundance of a nucleic acid sequence selected from the group consisting of SEQ ID NOS: 3-6, 11, 14, 16-23, 26, 27, 29, 30, 32, 35, 37, 39, 41, 42, 44, 45, or a sequence having at least about 80% identity thereto in said sample; wherein the abundance of said nucleic acid sequence is indicative of a cancer of esophagus origin.

According to some embodiments the nucleic acid sequence expression profile or relative abundance is determined by a method selected from the group consisting of nucleic acid hybridization and nucleic acid amplification. According to some embodiments the nucleic acid hybridization is performed using a solid-phase nucleic acid biochip array or in situ hybridization.

According to some embodiments the nucleic acid amplification method is real-time PCR. The real-time PCR method may comprise forward and reverse primers. According to some embodiments the forward primer comprises a sequence selected from the group consisting of SEQ ID NOS: 50-98 and 150. According to some embodiments the reverse primer comprises SEQ ID NO: 288.

According to additional embodiments the real-time PCR method further comprises a probe. According to some embodiments the probe comprises a sequence selected from the group consisting of a sequence that is complementary to a sequence selected from SEQ ID NOS: 1-49; a fragment thereof and a sequence having at least about 80% identity thereto. According to additional embodiments the probe comprises a sequence selected from the group consisting of SEQ ID NOS: 99-149 and 151.

According to another aspect, the present invention provides a kit for cancer classification, said kit comprising a probe comprising a sequence selected from the group consisting of a sequence that is complementary to a sequence selected from SEQ ID NOS: 1-49; a fragment thereof and a sequence having at least about 80% identity thereto.

According to additional embodiments the probe comprises a sequence selected from the group consisting of SEQ ID NOS: 99-149 and 151.

According to certain embodiments, said cancer is selected from the group consisting of liver cancer, biliary tract cancer, lung cancer, bladder cancer, prostate cancer, breast cancer, colon cancer, ovarian cancer, testicular cancer, stomach cancer, thyroid cancer, pancreas cancer, brain cancer, head and neck cancer, kidney cancer, melanoma, thymus cancer and esophagus cancer.

These and other embodiments of the present invention will become apparent in conjunction with the figures, description and claims that follow.

Figure 1A:
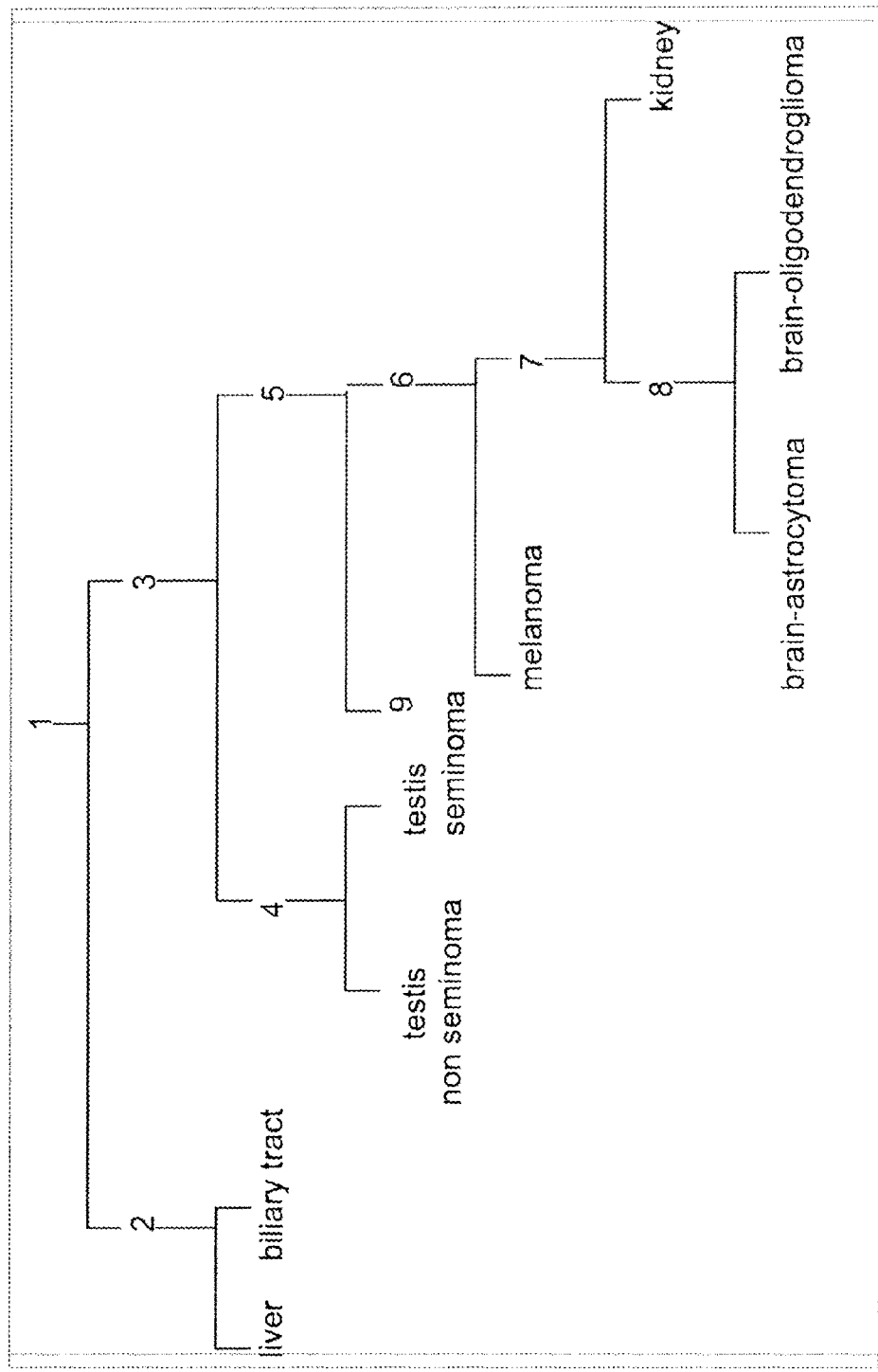
FIGS. 1A-1C demonstrate the structure of the binary decision-tree classifier, with 26 nodes (numbered, Table 3) and 27 leaves. Each node is a binary decision between two sets of samples, those to the left and right of the node. A series of binary decisions, starting at node #1 and moving downwards, lead to one of the possible tumor types, which are the "leaves" of the tree. A sample which is classified to the left branch at node #1 continues to node #2, otherwise it continues to node #3. A sample that reaches node #2, is further classified to either the left branch at node #2, and is assigned to the "liver" class, or to the right branch at node #2, and is assigned to the "biliary tract carcinoma" class.

Decisions are made at consecutive nodes using microRNA expression levels, until an end-point ("leaf" of the tree) is reached, indicating the predicted class for this sample. In specifying the tree structure, clinico-pathological considerations were combined with properties observed in the training set data.

Developing a different classifier for e.g. male and female cases or for different tumor sites would inefficiently exploit measured data and would require unwieldy numbers of samples. Instead, exceptions were noted for several special cases: For samples from female patients, testis or prostate origins were excluded from the KNN database, and the right branch was automatically taken in node 3 and node 16 in the decision-tree. For samples from male patients, ovary origin was excluded and the right branch taken at node 17. For samples that were indicated as metastases to the liver, liver origin (hepatocellular carcinoma and biliary tract carcinomas from within the liver) was excluded and the right branch taken at node 1. For samples indicated as brain metastases, brain origin was excluded and the right branch taken at node 7. Additional information is thus incorporated into the classification decision without loss of generality or need to retrain the classifier.

FIG. 2 demonstrates binary decisions at node #1 of the decision-tree. When training a decision algorithm for a given node, only samples from classes which are possible outcomes ("leaves") of this node are used for training. Tumors originating from tissues at the left branch at node #1, including tumors from the "liver" class and the "biliary tract" class (liver-cholangio; diamonds) are easily separated from tumors of non-liver and non-biliary tract origins (right branch at node #2; gray squares) using the expression levels of hsa-miR-200c (SEQ ID NO: 26) and hsa-miR-122 (SEQ ID NO: 6) (with one outlier), with a linear classifier (the diagonal line).

FIG. 3 demonstrates binary decisions at node #5 of the decision-tree. Tumors of epithelial origin (left branch at node #5, marked by diamonds) are easily separated from tumors of non-epithelial origin (right branch at node #5, marked by squares) using the expression levels of hsa-miR-200c (SEQ ID NO: 26) and hsa-miR-148b (SEQ ID NO: 17). The gray area (with higher levels of hsa-miR-200c) marks the region classified as epithelial (left branch) at this node.

FIG. 4 demonstrates binary decisions at node #7 of the decision-tree. Tumors originating in the brain (diamonds) are easily separated from tumors of kidney origin (squares) using the expression levels of hsa-miR-124 (SEQ ID NO: 7) and hsa-miR-9* (SEQ ID NO: 47).

FIG. 5 demonstrates binary decisions at node #10 of the decision-tree. Neuroendocrine tumors originating in the lung (diamonds) are easily separated from tumors of thyroid-medullary origin (squares) using the expression levels of hsa-miR-200a (SEQ ID NO: 24) and hsa-miR-222 (SEQ ID NO: 32).

FIG. 6 demonstrates binary decisions at node #12 of the decision-tree. Tumors originating in the gastrointestinal tract (left branch at node #12, marked by diamonds) are easily separated from tumors of non digestive origins (right branch at node #12, marked by squares) using the expression levels of hsa-miR-106a (SEQ ID NO: 3) and hsa-miR-192 (SEQ ID NO: 21).

FIG. 7 demonstrates binary decisions at node #16 of the decision-tree. Tumors originating in the prostate (left branch at node #16, marked by diamonds) are easily separated from tumors of other origins (right branch at node #16, marked by squares) using the expression levels of hsa-miR-185 (SEQ ID NO: 20) and hsa-miR-375 (SEQ ID NO: 42).

Figure 8B:
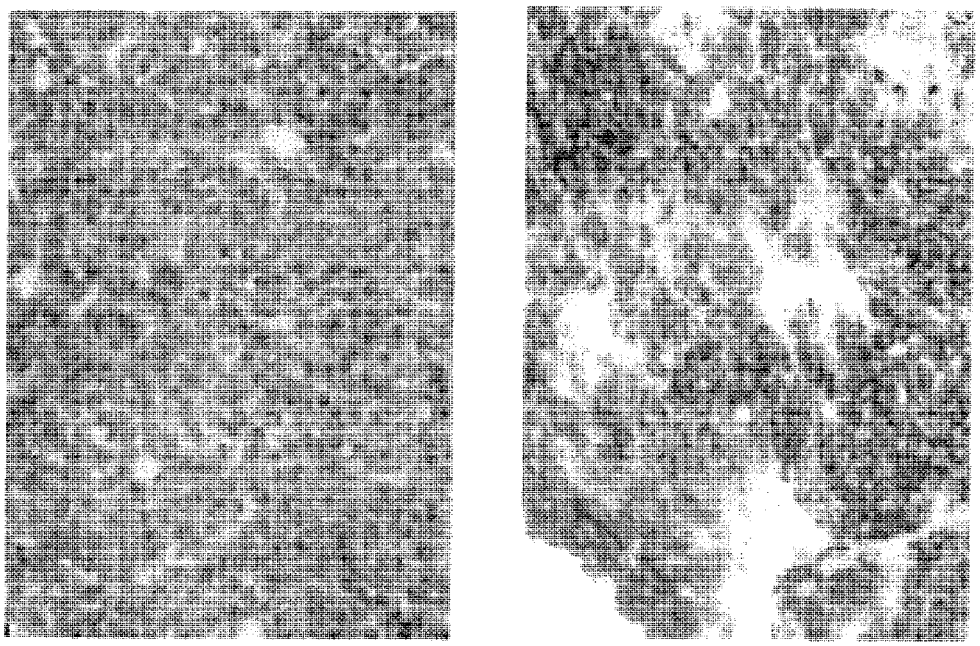

FIGS. 8A-8B demonstrate classification example. FIG. 8A shows that the measured levels (normalized Ct, inversely proportional to log(abundance)) of hsa-miR-200c (SEQ ID NO: 26) and hsa-miR-122 (SEQ ID NO: 6) are compared for all training set samples, indicating the left and right branches of node #1 (circles and stars respectively). One metastatic tumor excised from the brain (square), from a patient that had a concomitant tumor in the lung, and was therefore originally diagnosed as a lung cancer. However, this sample showed an uncharacteristic high expression of hsa-miR-122, a strong hepatic marker, and was consequently classified as possibly originating from the liver by the microRNA classifier. FIG. 8B shows that upon re-examination of the metastatic brain tumor by immunohistochemistry (blinded to the results of the microRNA classifier), this tumor was indeed found to be negative for lung specific markers: the sample was negative for immunohistochemical staining by both CK7 and TTF1, as well as CK20, CEA, CA125, s-100, thyroglobulin, chromogranin, synaptophysin, CD56, GFAP, calcitonin, and anterior pituitary hormones, while staining positive for CAM5.5' and AE1/AE3. This staining pattern was compatible with hepatocellular carcinoma, prompting further staining for HEPA1 and alpha fetoprotein. The tumor stained positive for both stains, consistent with a diagnosis of hepatocellular carcinoma (FIG. 8B). H&E staining (upper panel) showed that the metastasis is composed of sheets of cells with abundant eosinophilic cytoplasm and round to oval nuclei. Among many immunostains used to evaluate the origin of the tumor, HEPA-1 showed strong and specific immunopositivity (lower panel).

DETAILED DESCRIPTION OF THE INVENTION

Identification of the tissue-of-origin of a tumor is vital to its management. The present invention is based in part on the discovery that specific nucleic acid sequences can be used for the identification of the tissue-of-origin of a tumor. The present invention provides a sensitive, specific and accurate method which can be used to distinguish between different tissues and tumor origins. A new microRNA-based classifier was developed for determining tissue origin of tumors based on a surprisingly small number of 48 microRNAs markers. The classifier uses a specific algorithm and allows a clear interpretation of the specific biomarkers. High confidence predictions reach 90% sensitivity and 99% specificity.

According to the present invention each node in the classification tree may be used as an independent differential diagnosis tool, for example in the identification of different types of lung cancer. The performance of the classifier using a small number of markers highlights the utility of microRNA as tissue-specific cancer biomarkers, and provides an effective means for facilitating diagnosis of CUP and more generally of identifying tumor origins of metastases.

The possibility to distinguish between different tumor origins facilitates providing the patient with the best and most suitable treatment.

The present invention provides diagnostic assays and methods, both quantitative and qualitative for detecting, diagnosing, monitoring, staging and prognosticating cancers by comparing the levels of the specific microRNA molecules of the invention. Such levels are preferably measured in at least one of biopsies, tumor samples, fine-needle aspiration (FNA), cells, tissues and/or bodily fluids. The present invention provides methods for diagnosing the presence of a specific cancer by analyzing the levels of said microRNA molecules in biopsies, tumor samples, cells, tissues or bodily fluids.

In the present invention, determining the levels of said microRNA in biopsies, tumor samples, cells, tissues or bodily fluid, is particularly useful for discriminating between different cancers.

All the methods of the present invention may optionally further include measuring levels of other cancer markers. Other cancer markers, in addition to said microRNA molecules, useful in the present invention will depend on the cancer being tested and are known to those of skill in the art.

Assay techniques that can be used to determine levels of gene expression, such as the nucleic acid sequence of the present invention, in a sample derived from a patient are well known to those of skill in the art. Such assay methods include, but are not limited to, reverse transcriptase PCR (RT-PCR) assays, nucleic acid microarrays and biochip analysis, immunohistochemistry assays, in situ hybridization assays, competitive-binding assays, northern blot analyses and ELISA assays.

According to one embodiment, the assay is based on expression level of 48 microRNAs in RNA extracted from FFPE metastatic tumor tissue. The test is a quantitative real time reverse transcriptase polymerase chain reaction (qRT-PCR) test. RNA is first polyadenylated and then reverse transcribed using universal poly(T) adapter to create cDNA. The cDNA is amplified using specific forward primer and universal reverse primer (with a sequence complementary to the 5' tail of the poly(T) adapter), and detected by specific MGB probes (see specific sequences in Table 1).

The expression levels are used to infer the sample origin using analysis techniques such as but not limit to decision tree classifier, logistic regression classifier, linear regression classifier, nearest neighbor classifier (including K nearest neighbors), neural network classifier and nearest centroid classifier.

The expression levels are used to make binary decisions (at each relevant node) following the pre-defined structure of the binary decision-tree (defined using the training set). At each node, the expressions of one or several microRNAs are combined together using a simple function of the form P=exp(b0+b1*mir1+b2*mir2+b3*mir3 ... ), where the values of b0, b1, b2 ... and the identities of the microRNAs have been pre-determined (using the training set). The resulting P is compared to a threshold level PTH (which was also determined using the training set), and the classification continues to the left or right branch according to whether P is larger or smaller than PTH for that node. This continues until an end-point ("leaf") of the tree is reached.

Training the tree algorithm means determining: the tree structure (which nodes there are and what is on each side), which miRs are used in each node and the values of b0, b1, b2 ... and PTH. These were determined by a combination of machine learning, optimization algorithm, and trial and error by experts in machine learning and diagnostic algorithms.

In some embodiments of the invention, correlations and/or hierarchical clustering can be used to assess the similarity of the expression level of the nucleic acid sequences of the invention between a specific sample and different exemplars of cancer samples. An arbitrary threshold on the expression level of one or more nucleic acid sequences can be set for assigning a sample or cancer sample to one of two groups. Alternatively, in a preferred embodiment, expression levels of one or more nucleic acid sequences of the invention are combined by a method such as logistic regression to define a metric which is then compared to previously measured samples or to a threshold. The threshold for assignment is treated as a parameter, which can be used to quantify the confidence with which samples are assigned to each class. The threshold for assignment can be scaled to favor sensitivity or specificity, depending on the clinical scenario. The correlation value to the reference data generates a continuous score that can be scaled and provides diagnostic information on the likelihood that a sample belongs to a certain class of cancer origin or type. In multivariate analysis, the microRNA signature provides a high level of prognostic information.

In another preferred embodiment, expression level of the nucleic acids is used to classify a test sample by comparison to a training set of samples. In this embodiment, the test sample is compared in turn to each one of the training set samples. Each such pairwise comparison is performed by comparing the expression levels of one or multiple nucleic acids between the test sample and the specific training sample. Each such pairwise comparison generates a combined metric for the multiple nucleic acids, which can be calculated by various numeric methods such as correlation, cosine, Euclidian distance, mean square distance, or other methods known to those skilled in the art. The training samples are then ranked according to this metric, and the samples with the highest values of the metric (or lowest values, according to the type of metric) are identified, indicating those samples that are most similar to the test sample. By choosing a parameter K, this generates a list that includes the K training samples that are most similar to the test sample. Various methods can then be applied to identify from this list the predicted class of the test sample. In a favored embodiment, the test sample is predicted to belong to the class that has the highest number of representative in the list of K most-similar training samples (this method is known as the K Nearest Neighbors method). Other embodiments may provide a list of predictions including all or part of the classes represented in the list, those classes that are represented more than a given minimum number of times, or other voting schemes whereby classes are grouped together.

DEFINITIONS

It is to be understood that the terminology used herein is for the purpose of describing particular embodiments only and is not intended to be limiting. It must be noted that, as used in the specification and the appended claims, the singular forms "a," "an" and "the" include plural referents unless the context clearly dictates otherwise.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9 and 7.0 are explicitly contemplated.

About

As used herein, the term "about" refers to +/−10%.

Attached

"Attached" or "immobilized," as used herein, to refer to a probe and a solid support means that the binding between the probe and the solid support is sufficient to be stable under conditions of binding, washing, analysis, and removal. The binding may be covalent or non-covalent. Covalent bonds may be formed directly between the probe and the solid support or may be formed by a cross linker or by inclusion of a specific reactive group on either the solid support or the probe or both molecules. Non-covalent binding may be one or more of electrostatic, hydrophilic, and hydrophobic interactions. Included in non-covalent binding is the covalent attachment of a molecule, such as streptavidin, to the support and the non-covalent binding of a biotinylated probe to the streptavidin. Immobilization may also involve a combination of covalent and non-covalent interactions.

Baseline

"Baseline," as used herein, means the initial cycles of PCR, in which there is little change in fluorescence signal.

Biological Sample

"Biological sample," as used herein, means a sample of biological tissue or fluid that comprises nucleic acids. Such samples include, but are not limited to, tissue or fluid isolated from subjects. Biological samples may also include sections of tissues such as biopsy and autopsy samples, FFPE samples, frozen sections taken for histological purposes, blood, blood fraction, plasma, serum, sputum, stool, tears, mucus, hair, skin, urine, effusions, ascitic fluid, amniotic fluid, saliva, cerebrospinal fluid, cervical secretions, vaginal secretions, endometrial secretions, gastrointestinal secretions, bronchial secretions, cell line, tissue sample, or secretions from the breast. A biological sample may be provided by fine-needle aspiration (FNA). A biological sample may be provided by removing a sample of cells from a subject but can also be accomplished by using previously isolated cells (e.g., isolated by another person, at another time, and/or for another purpose), or by performing the methods described herein in vivo. Archival tissues, such as those having treatment or outcome history, may also be used. Biological samples also include explants and primary and/or transformed cell cultures derived from animal or human tissues.

Cancer

The term "cancer" is meant to include all types of cancerous growths or oncogenic processes, metastatic tissues or malignantly transformed cells, tissues, or organs, irrespective of histopathologic type or stage of invasiveness. Examples of cancers include, but are not limited, to solid tumors and leukemias, including: apudoma, choristoma, branchioma, malignant carcinoid syndrome, carcinoid heart disease, carcinoma (e.g., Walker, basal cell, basosquamous, Brown-Pearce, ductal, Ehrlich tumor, non-small cell lung (e.g., lung squamous cell carcinoma, lung adenocarcinoma and lung undifferentiated large cell carcinoma), oat cell, papillary, bronchiolar, bronchogenic, squamous cell, and transitional cell), histiocytic disorders, leukemia (e.g., B cell, mixed cell, null cell, T cell, T-cell chronic, HTLV-II-associated, lymphocytic acute, lymphocytic chronic, mast cell, and myeloid), histiocytosis malignant, Hodgkin disease, immunoproliferative small, non-Hodgkin lymphoma, plasmacytoma, reticuloendotheliosis, melanoma, chondroblastoma, chondroma, chondrosarcoma, fibroma, fibrosarcoma, giant cell tumors, histiocytoma, lipoma, liposarcoma, mesothelioma, myxoma, myxosarcoma, osteoma, osteosarcoma, Ewing sarcoma, synovioma, adenofibroma, adenolymphoma, carcinosarcoma, chordoma, craniopharyngioma, dysgerminoma, hamartoma, mesenchymoma, mesonephroma, myosarcoma, ameloblastoma, cementoma, odontoma, teratoma, thymoma, trophoblastic tumor, adeno-carcinoma, adenoma, cholangioma, cholesteatoma, cylindroma, cystadenocarcinoma, cystadenoma, granulosa cell tumor, gynandroblastoma, hepatoma, hidradenoma, islet cell tumor, Leydig cell tumor, papilloma, Sertoli cell tumor, theca cell tumor, leiomyoma, leiomyosarcoma, myoblastoma, myosarcoma, rhabdomyoma, rhabdomyosarcoma, ependymoma, ganglioneuroma, glioma, medulloblastoma, meningioma, neurilemmoma, neuroblastoma, neuroepithelioma, neurofibroma, neuroma, paraganglioma, paraganglioma nonchromaffin, angiokeratoma, angiolymphoid hyperplasia with eosinophilia, angioma sclerosing, angiomatosis, glomangioma, hemangioendothelioma, hemangioma, hemangiopericytoma, hemangiosarcoma, lymphangioma, lymphangiomyoma, lymphangiosarcoma, pinealoma, carcinosarcoma, chondrosarcoma, cystosarcoma, phyllodes, fibrosarcoma, hemangiosarcoma, leimyosarcoma, leukosarcoma, liposarcoma, lymphangiosarcoma, myosarcoma, myxosarcoma, ovarian carcinoma, rhabdomyosarcoma, sarcoma (e.g., Ewing, experimental, Kaposi, and mast cell), neurofibromatosis, and cervical dysplasia, and other conditions in which cells have become immortalized or transformed.

Classification

The term classification refers to a procedure and/or algorithm in which individual items are placed into groups or classes based on quantitative information on one or more characteristics inherent in the items (referred to as traits, variables, characters, features, etc.) and based on a statistical model and/or a training set of previously labeled items. A "classification tree" is a decision tree that places categorical variables into classes.

Complement

"Complement" or "complementary" is used herein to refer to a nucleic acid may mean Watson-Crick (e.g., A-T/U and C-G) or Hoogsteen base pairing between nucleotides or nucleotide analogs of nucleic acid molecules. A full complement or fully complementary means 100% complementary base pairing between nucleotides or nucleotide analogs of nucleic acid molecules. In some embodiments, the complementary sequence has a reverse orientation (5'-3').

Ct

Ct signals represent the first cycle of PCR where amplification crosses a threshold (cycle threshold) of fluorescence. Accordingly, low values of Ct represent high abundance or expression levels of the microRNA.

In some embodiments the PCR Ct signal is normalized such that the normalized Ct remains inversed from the expression level. In other embodiments the PCR Ct signal may be normalized and then inverted such that low normalized-inverted Ct represents low abundance or expression levels of the microRNA.

Data Processing Routine

As used herein, a "data processing routine" refers to a process that can be embodied in software that determines the biological significance of acquired data (i.e., the ultimate results of an assay or analysis). For example, the data processing routine can make determination of tissue of origin based upon the data collected. In the systems and methods herein, the data processing routine can also control the data collection routine based upon the results determined. The data processing routine and the data collection routines can be integrated and provide feedback to operate the data acquisition, and hence provide assay-based judging methods.

Data Set

As use herein, the term "data set" refers to numerical values obtained from the analysis. These numerical values associated with analysis may be values such as peak height and area under the curve.

Data Structure

As used herein, the term "data structure" refers to a combination of two or more data sets, applying one or more mathematical manipulations to one or more data sets to obtain one or more new data sets, or manipulating two or more data sets into a form that provides a visual illustration of the data in a new way. An example of a data structure prepared from manipulation of two or more data sets would be a hierarchical cluster.

Detection

"Detection" means detecting the presence of a component in a sample. Detection also means detecting the absence of a component. Detection also means determining the level of a component, either quantitatively or qualitatively.

Differential Expression

"Differential expression" means qualitative or quantitative differences in the temporal and/or spatial gene expression patterns within and among cells and tissue. Thus, a differentially expressed gene may qualitatively have its expression altered, including an activation or inactivation, in, e.g., normal versus diseased tissue. Genes may be turned on or turned off in a particular state, relative to another state, thus permitting comparison of two or more states. A qualitatively regulated gene may exhibit an expression pattern within a state or cell type which may be detectable by standard techniques. Some genes may be expressed in one state or cell type, but not in both. Alternatively, the difference in expression may be quantitative, e.g., in that expression is modulated, up-regulated, resulting in an increased amount of transcript, or down-regulated, resulting in a decreased amount of transcript. The degree to which expression differs needs only to be large enough to quantify via standard characterization techniques such as expression arrays, quantitative reverse transcriptase PCR, northern blot analysis, real-time PCR, in situ hybridization and RNase protection.

expression profile

The term "expression profile" is used broadly to include a genomic expression profile, e.g., an expression profile of microRNAs. Profiles may be generated by any convenient means for determining a level of a nucleic acid sequence, e.g., quantitative hybridization of microRNA, labeled microRNA, amplified microRNA, cDNA, etc., quantitative PCR, ELISA for quantitation, and the like, and allow the analysis of differential gene expression between two samples. A subject or patient tumor sample, e.g., cells or collections thereof, e.g., tissues, is assayed. Samples are collected by any convenient method, as known in the art. Nucleic acid sequences of interest are nucleic acid sequences that are found to be predictive, including the nucleic acid sequences provided above, where the expression profile may include expression data for 5, 10, 20, 25, 50, 100 or more of the nucleic acid sequences, including all of the listed nucleic acid sequences. According to some embodiments, the term "expression profile" means measuring the relative abundance of the nucleic acid sequences in the measured samples.

Expression Ratio

"Expression ratio," as used herein, refers to relative expression levels of two or more nucleic acids as determined by detecting the relative expression levels of the corresponding nucleic acids in a biological sample.

FDR

When performing multiple statistical tests, for example in comparing the signal between two groups in multiple data features, there is an increasingly high probability of obtaining false positive results, by random differences between the groups that can reach levels that would otherwise be considered statistically significant. In order to limit the proportion of such false discoveries, statistical significance is defined only for data features in which the differences reached a p-value (by two-sided t-test) below a threshold, which is dependent on the number of tests performed and the distribution of p-values obtained in these tests.

Fragment "Fragment" is used herein to indicate a non-full-length part of a nucleic acid. Thus, a fragment is itself also a nucleic acid.

Gene

"Gene," as used herein, may be a natural (e.g., genomic) or synthetic gene comprising transcriptional and/or translational regulatory sequences and/or a coding region and/or non-translated sequences (e.g., introns, 5'- and 3'-untranslated sequences). The coding region of a gene may be a nucleotide sequence coding for an amino acid sequence or a functional RNA, such as tRNA, rRNA, catalytic RNA, siRNA, miRNA or antisense RNA. A gene may also be an mRNA or cDNA corresponding to the coding regions (e.g., exons and miRNA) optionally comprising 5'- or 3'-untranslated sequences linked thereto. A gene may also be an amplified nucleic acid molecule produced in vitro, comprising all or a part of the coding region and/or 5'- or 3'-untranslated sequences linked thereto.

Groove Binder/Minor Groove Binder (MGB)

"Groove binder" and/or "minor groove binder" may be used interchangeably and refer to small molecules that fit into the minor groove of double-stranded DNA, typically in a sequence-specific manner. Minor groove binders may be long, flat molecules that can adopt a crescent-like shape and thus fit snugly into the minor groove of a double helix, often displacing water. Minor groove binding molecules may typically comprise several aromatic rings connected by bonds with torsional freedom such as furan, benzene, or pyrrole rings. Minor groove binders may be antibiotics such as netropsin, distamycin, berenil, pentamidine and other aromatic diamidines, Hoechst 33258, SN 6999, aureolic antitumor drugs such as chromomycin and mithramycin, CC-1065, dihydrocyclopyrroloindole tripeptide (DPI3), 1,2-dihydro-(3H)-pyrrolo[3,2-e]indole-7-carboxylate (CDPI3), and related compounds and analogues, including those described in Nucleic Acids in Chemistry and Biology, 2nd ed., Blackburn and Gait, eds., Oxford University Press, 1996, and PCT Published Application No. WO 03/078450, the contents of which are incorporated herein by reference. A minor groove binder may be a component of a primer, a probe, a hybridization tag complement, or combinations thereof. Minor groove binders may increase the Tm of the primer or a probe to which they are attached, allowing such primers or probes to effectively hybridize at higher temperatures.

Host Cell

"Host cell," as used herein, may be a naturally occurring cell or a transformed cell that may contain a vector and may support replication of the vector. Host cells may be cultured cells, explants, cells in vivo, and the like. Host cells may be prokaryotic cells, such as $E.\ coli$, or eukaryotic cells, such as yeast, insect, amphibian, or mammalian cells, such as CHO and HeLa cells.

Identity

"Identical" or "identity," as used herein, in the context of two or more nucleic acids or polypeptide sequences mean that the sequences have a specified percentage of residues that are the same over a specified region. The percentage may be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of single sequence are included in the denominator but not the numerator of the calculation. When comparing DNA and RNA sequences, thymine (T) and uracil (U) may be considered equivalent. Identity may be performed manually or by using a computer sequence algorithm such as BLAST or BLAST 2.0.

In Situ Detection

"In situ detection," as used herein, means the detection of expression or expression levels in the original site, hereby meaning in a tissue sample such as biopsy.

K-Nearest Neighbor

The phrase "k-nearest neighbor" refers to a classification method that classifies a point by calculating the distances between the point and points in the training data set. It then assigns the point to the class that is most common among its k-nearest neighbors (where k is an integer).

Label

"Label," as used herein, means a composition detectable by spectroscopic, photochemical, biochemical, immunochemical, chemical, or other physical means. For example, useful labels include 32P, fluorescent dyes, electron-dense reagents, enzymes (e.g., as commonly used in an ELISA), biotin, digoxigenin, or haptens and other entities which can be made detectable. A label may be incorporated into nucleic acids and proteins at any position.

Logistic Regression

Logistic regression is part of a category of statistical models called generalized linear models. Logistic regression can allow one to predict a discrete outcome, such as group membership, from a set of variables that may be continuous, discrete, dichotomous, or a mix of any of these. The dependent or response variable can be dichotomous, for example, one of two possible types of cancer. Logistic regression models the natural log of the odds ratio, i.e., the ratio of the probability of belonging to the first group (P) over the probability of belonging to the second group (1-P), as a linear combination of the different expression levels (in log-space). The logistic regression output can be used as a classifier by prescribing that a case or sample will be classified into the first type if P is greater than 0.5 or 50%. Alternatively, the calculated probability P can be used as a variable in other contexts, such as a 1D or 2D threshold classifier.

1D/2D Threshold Classifier

"1D/2D threshold classifier," as used herein, may mean an algorithm for classifying a case or sample such as a cancer sample into one of two possible types such as two types of cancer. For a 1D threshold classifier, the decision is based on one variable and one predetermined threshold value; the sample is assigned to one class if the variable exceeds the threshold and to the other class if the variable is less than the threshold. A 2D threshold classifier is an algorithm for classifying into one of two types based on the values of two variables. A threshold may be calculated as a function (usually a continuous or even a monotonic function) of the first variable; the decision is then reached by comparing the second variable to the calculated threshold, similar to the 1D threshold classifier.

Metastasis

"Metastasis" means the process by which cancer spreads from the place at which it first arose as a primary tumor to other locations in the body. The metastatic progression of a primary tumor reflects multiple stages, including dissociation from neighboring primary tumor cells, survival in the circulation, and growth in a secondary location.

Node

A "node" is a decision point in a classification (i.e., decision) tree. Also, a point in a neural net that combines input from other nodes and produces an output through application of an activation function. A "leaf" is a node not further split, the terminal grouping in a classification or decision tree.

Nucleic Acid

"Nucleic acid" or "oligonucleotide" or "polynucleotide," as used herein, mean at least two nucleotides covalently linked together. The depiction of a single strand also defines the sequence of the complementary strand. Thus, a nucleic acid also encompasses the complementary strand of a depicted single strand. Many variants of a nucleic acid may be used for the same purpose as a given nucleic acid. Thus, a nucleic acid also encompasses substantially identical nucleic acids and complements thereof. A single strand provides a probe that may hybridize to a target sequence under stringent hybridization conditions. Thus, a nucleic acid also encompasses a probe that hybridizes under stringent hybridization conditions.

Nucleic acids may be single-stranded or double-stranded, or may contain portions of both double-stranded and single-stranded sequences. The nucleic acid may be DNA, both genomic and cDNA, RNA, or a hybrid, where the nucleic acid may contain combinations of deoxyribo- and ribo-nucleotides, and combinations of bases including uracil, adenine, thymine, cytosine, guanine, inosine, xanthine hypoxanthine, isocytosine and isoguanine. Nucleic acids may be obtained by chemical synthesis methods or by recombinant methods.

A nucleic acid will generally contain phosphodiester bonds, although nucleic acid analogs may be included that may have at least one different linkage, e.g., phosphoramidate, phosphorothioate, phosphorodithioate, or O-methylphosphoroamidite linkages and peptide nucleic acid backbones and linkages. Other analog nucleic acids include those with positive backbones, non-ionic backbones and non-ribose backbones, including those described in U.S. Pat. Nos. 5,235,033 and 5,034,506, which are incorporated herein by reference. Nucleic acids containing one or more non-naturally occurring or modified nucleotides are also included within one definition of nucleic acids. The modified nucleotide analog may be located for example at the 5'-end and/or the 3'-end of the nucleic acid molecule. Representative examples of nucleotide analogs may be selected from sugar- or backbone-modified ribonucleotides. It should be noted, however, that also nucleobase-modified ribonucleotides, i.e., ribonucleotides, containing a non-naturally occurring nucleobase instead of a naturally occurring nucleobase such as uridine or cytidine modified at the 5-position, e.g., 5-(2-amino) propyl uridine, 5-bromo uridine; adenosine and guanosine modified at the 8-position, e.g., 8-bromo guanosine; deaza nucleotides, e.g., 7-deaza-adenosine; O- and N-alkylated nucleotides, e.g., N6-methyl adenosine are suitable. The 2'-OH-group may be replaced by a group selected from H, OR, R, halo, SH, SR, NH2, NHR, NR2 or CN, wherein R is C1-C6 alkyl, alkenyl or alkynyl and halo is F, Cl, Br or I. Modified nucleotides also include nucleotides conjugated with cholesterol through, e.g., a hydroxyprolinol linkage as described in Krutzfeldt et al., Nature 2005; 438:685-689, Soutschek et al., Nature 2004; 432:173-178, and U.S. Patent Publication No. 20050107325, which are incorporated herein by reference. Additional modified nucleotides and nucleic acids are described in U.S. Patent Publication No. 20050182005, which is incorporated herein by reference. Modifications of the ribose-phosphate backbone may be done for a variety of reasons, e.g., to increase the stability and half-life of such molecules in physiological environments, to enhance diffusion across cell membranes, or as probes on a biochip. The backbone modification may also enhance resistance to degradation, such as in the harsh endocytic environment of cells. The backbone modification may also reduce nucleic acid clearance by hepatocytes, such as in the liver and kidney. Mixtures of naturally occurring nucleic acids and analogs may be made; alternatively, mixtures of different nucleic acid analogs, and mixtures of naturally occurring nucleic acids and analogs may be made.

Probe

"Probe," as used herein, means an oligonucleotide capable of binding to a target nucleic acid of complementary sequence through one or more types of chemical bonds, usually through complementary base pairing, usually through hydrogen bond formation. Probes may bind target sequences lacking complete complementarity with the probe sequence depending upon the stringency of the hybridization conditions. There may be any number of base pair mismatches which will interfere with hybridization between the target sequence and the single-stranded nucleic acids described herein. However, if the number of mutations is so great that no hybridization can occur under even the least stringent of hybridization conditions, the sequence is not a complementary target sequence. A probe may be single-stranded or partially single- and partially double-stranded. The strandedness of the probe is dictated by the structure, composition, and properties of the target sequence. Probes may be directly labeled or indirectly labeled such as with biotin to which a streptavidin complex may later bind.

Reference Value

As used herein, the term "reference value" or "reference expression profile" refers to a criterion expression value to which measured values are compared in order to determine the detection of a specific cancer. The reference value may be based on the abundance of the nucleic acids, or may be based on a combined metric score thereof.

In preferred embodiments the reference value is determined from statistical analysis of studies that compare microRNA expression with known clinical outcomes.

Sensitivity

"Sensitivity," as used herein, may mean a statistical measure of how well a binary classification test correctly identifies a condition, for example, how frequently it correctly classifies a cancer into the correct type out of two possible types. The sensitivity for class A is the proportion of cases that are determined to belong to class "A" by the test out of the cases that are in class "A," as determined by some absolute or gold standard.

Specificity

"Specificity," as used herein, may mean a statistical measure of how well a binary classification test correctly identifies a condition, for example, how frequently it correctly classifies a cancer into the correct type out of two possible types. The sensitivity for class A is the proportion of cases that are determined to belong to class "not A" by the test out of the cases that are in class "not A," as determined by some absolute or gold standard.

Stringent Hybridization Conditions

"Stringent hybridization conditions," as used herein, mean conditions under which a first nucleic acid sequence (e.g., probe) will hybridize to a second nucleic acid sequence (e.g., target), such as in a complex mixture of nucleic acids. Stringent conditions are sequence-dependent and will be different in different circumstances. Stringent conditions may be selected to be about 5-10° C. lower than the thermal melting point ($T_m$) for the specific sequence at a defined ionic strength pH. The $T_m$ may be the temperature (under defined ionic strength, pH, and nucleic concentration) at which 50% of the probes complementary to the target hybridize to the target sequence at equilibrium (as the target sequences are present in excess, at Tm, 50% of the probes are occupied at equilibrium). Stringent conditions may be those in which the salt concentration is less than about 1.0 M sodium ion, such as about 0.01-1.0 M sodium ion concentration (or other salts) at pH 7.0 to 8.3 and the temperature is at least about 30° C. for short probes (e.g., about 10-50 nucleotides) and at least about 60° C. for long probes (e.g., greater than about 50 nucleotides). Stringent conditions may also be achieved with the addition of destabilizing agents such as formamide. For selective or specific hybridization, a positive signal may be at least 2 to 10 times background hybridization. Exemplary stringent hybridization conditions include the following: 50% formamide, 5×SSC, and 1% SDS, incubating at 42° C., or, 5×SSC, 1% SDS, incubating at 65° C., with wash in 0.2×SSC, and 0.1% SDS at 65° C.

Substantially Complementary

"Substantially complementary," as used herein, means that a first sequence is at least 60%, 65%, 70%, 75%, 80%, 85%, 90%, 95%, 97%, 98% or 99% identical to the complement of a second sequence over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100 or more nucleotides, or that the two sequences hybridize under stringent hybridization conditions.

Substantially Identical

"Substantially identical," as used herein, means that a first and a second sequence are at least 60%, 65%, 70%, 75%, 80%, 85%, 90%, 95%, 97%, 98% or 99% identical over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100 or more nucleotides or amino acids, or with respect to nucleic acids, if the first sequence is substantially complementary to the complement of the second sequence.

Subject

As used herein, the term "subject" refers to a mammal, including both human and other mammals. The methods of the present invention are preferably applied to human subjects.

Target Nucleic Acid

"Target nucleic acid," as used herein, means a nucleic acid or variant thereof that may be bound by another nucleic acid. A target nucleic acid may be a DNA sequence. The target nucleic acid may be RNA. The target nucleic acid may comprise a mRNA, tRNA, shRNA, siRNA or Piwi-interacting RNA, or a pri-miRNA, pre-miRNA, miRNA, or anti-miRNA.

The target nucleic acid may comprise a target miRNA binding site or a variant thereof. One or more probes may bind the target nucleic acid. The target binding site may comprise 5-100 or 10-60 nucleotides. The target binding site may comprise a total of 5, 6, 7, 8, 9, 10, 11, 12, 13, 14, 15, 16, 17, 18, 19, 20, 21, 22, 23, 24, 25, 26, 27, 28, 29, 30-40, 40-50, 50-60, 61, 62 or 63 nucleotides. The target site sequence may comprise at least 5 nucleotides of the sequence of a target miRNA binding site disclosed in U.S. patent application Ser. Nos. 11/384,049, 11/418,870 or 11/429,720, the contents of which are incorporated herein.

Threshold

As used herein, the term "threshold" means the numerical value assigned for each run, which reflects a statistically significant point above the calculated PCR baseline.

Tissue Sample

As used herein, a tissue sample is tissue obtained from a tissue biopsy using methods well known to those of ordinary skill in the related medical arts. The phrase "suspected of being cancerous," as used herein, means a cancer tissue sample believed by one of ordinary skill in the medical arts to contain cancerous cells. Methods for obtaining the sample from the biopsy include gross apportioning of a mass, microdissection, laser-based microdissection, or other art-known cell-separation methods.

Tumor

"Tumor," as used herein, refers to all neoplastic cell growth and proliferation, whether malignant or benign, and all precancerous and cancerous cells and tissues.

Variant

"Variant," as used herein, referring to a nucleic acid means (i) a portion of a referenced nucleotide sequence; (ii) the complement of a referenced nucleotide sequence or portion thereof; (iii) a nucleic acid that is substantially identical to a referenced nucleic acid or the complement thereof; or (iv) a nucleic acid that hybridizes under stringent conditions to the referenced nucleic acid, complement thereof, or a sequence substantially identical thereto.

Wild Type

As used herein, the term "wild-type" sequence refers to a coding, a non-coding or an interface sequence which is an allelic form of sequence that performs the natural or normal function for that sequence. Wild-type sequences include multiple allelic forms of a cognate sequence, for example, multiple alleles of a wild type sequence may encode silent or conservative changes to the protein sequence that a coding sequence encodes.

The present invention employs miRNAs for the identification, classification and diagnosis of specific cancers and the identification of their tissues of origin.

1. microRNA Processing

A gene coding for microRNA (miRNA) may be transcribed leading to production of a miRNA primary transcript known as the pri-miRNA. The pri-miRNA may comprise a hairpin with a stem and loop structure. The stem of the hairpin may comprise mismatched bases. The pri-miRNA may comprise several hairpins in a polycistronic structure.

The hairpin structure of the pri-miRNA may be recognized by Drosha, which is an RNase III endonuclease. Drosha may recognize terminal loops in the pri-miRNA and cleave approximately two helical turns into the stem to produce a 60-70 nt precursor known as the pre-miRNA. Drosha may cleave the pri-miRNA with a staggered cut typical of RNase III endonucleases yielding a pre-miRNA stem loop with a 5' phosphate and ~2 nucleotide 3' overhang. Approximately one helical turn of stem (~10 nucleotides) extending beyond the Drosha cleavage site may be essential for efficient processing. The pre-miRNA may then be actively transported from the nucleus to the cytoplasm by Ran-GTP and the export receptor Ex-portin-5.

The pre-miRNA may be recognized by Dicer, which is also an RNase III endonuclease. Dicer may recognize the double-stranded stem of the pre-miRNA. Dicer may also cut off the terminal loop two helical turns away from the base of the stem loop, leaving an additional 5' phosphate and a ~2 nucleotide 3' overhang. The resulting siRNA-like duplex, which may comprise mismatches, comprises the mature miRNA and a similar-sized fragment known as the miRNA*. The miRNA and miRNA* may be derived from opposing arms of the pri-miRNA and pre-miRNA. mRNA* sequences may be found in libraries of cloned miRNAs, but typically at lower frequency than the miRNAs.

Although initially present as a double-stranded species with miRNA*, the miRNA may eventually become incorporated as a single-stranded RNA into a ribonucleoprotein complex known as the RNA-induced silencing complex (RISC). Various proteins can form the RISC, which can lead to variability in specificity for miRNA/miRNA* duplexes, binding site of the target gene, activity of miRNA (repress or activate), and which strand of the miRNA/miRNA* duplex is loaded in to the RISC.

When the miRNA strand of the miRNA:miRNA* duplex is loaded into the RISC, the miRNA* may be removed and degraded. The strand of the miRNA:miRNA* duplex that is loaded into the RISC may be the strand whose 5' end is less tightly paired. In cases where both ends of the miRNA:miRNA* have roughly equivalent 5' pairing, both miRNA and miRNA* may have gene silencing activity.

The RISC may identify target nucleic acids based on high levels of complementarity between the miRNA and the mRNA, especially by nucleotides 2-7 of the miRNA. Only one case has been reported in animals where the interaction between the miRNA and its target was along the entire length of the miRNA. This was shown for miR-196 and Hox B8 and it was further shown that miR-196 mediates the cleavage of the Hox B8 mRNA (Yekta et al. Science 2004; 304:594-596). Otherwise, such interactions are known only in plants (Bartel & Bartel 2003; 132:709-717).

A number of studies have looked at the base-pairing requirement between miRNA and its mRNA target for achieving efficient inhibition of translation (reviewed by Bartel 2004; 116:281-297). In mammalian cells, the first 8 nucleotides of the miRNA may be important (Doench & Sharp GenesDev 2004; 18:504-511). However, other parts of the microRNA may also participate in mRNA binding. Moreover, sufficient base pairing at the 3' can compensate for insufficient pairing at the 5' (Brennecke et al., PloS Biol 2005; 3:e85). Computation studies, analyzing miRNA binding on whole genomes have suggested a specific role for bases 2-7 at the 5' of the miRNA in target binding but the role of the first nucleotide, found usually to be "A" was also recognized (Lewis et al. Cell 2005; 120:15-20). Similarly, nucleotides 1-7 or 2-8 were used to identify and validate targets by Krek et al. (Nat Genet. 2005; 37:495-500).

The target sites in the mRNA may be in the 5' UTR, the 3' UTR or in the coding region. Interestingly, multiple miRNAs may regulate the same mRNA target by recognizing the same or multiple sites. The presence of multiple miRNA binding sites in most genetically identified targets may indicate that the cooperative action of multiple RISCs provides the most efficient translational inhibition.

miRNAs may direct the RISC to down-regulate gene expression by either of two mechanisms: mRNA cleavage or translational repression. The miRNA may specify cleavage of the mRNA if the mRNA has a certain degree of complementarity to the miRNA. When a miRNA guides cleavage, the cut may be between the nucleotides pairing to residues 10 and 11 of the miRNA. Alternatively, the miRNA may repress translation if the miRNA does not have the requisite degree of complementarity to the miRNA. Translational repression may be more prevalent in animals since animals may have a lower degree of complementarity between the miRNA and binding site.

It should be noted that there may be variability in the 5' and 3' ends of any pair of miRNA and miRNA*. This variability may be due to variability in the enzymatic processing of Drosha and Dicer with respect to the site of cleavage. Variability at the 5' and 3' ends of miRNA and miRNA* may also be due to mismatches in the stem structures of the pri-miRNA and pre-miRNA. The mismatches of the stem strands may lead to a population of different hairpin structures. Variability in the stem structures may also lead to variability in the products of cleavage by Drosha and Dicer.

2. Nucleic Acids

Nucleic acids are provided herein. The nucleic acids comprise the sequences of SEQ ID NOS: 1-288 or variants thereof. The variant may be a complement of the referenced nucleotide sequence. The variant may also be a nucleotide sequence that is substantially identical to the referenced nucleotide sequence or the complement thereof. The variant may also be a nucleotide sequence which hybridizes under stringent conditions to the referenced nucleotide sequence, complements thereof, or nucleotide sequences substantially identical thereto.

The nucleic acid may have a length of from about 10 to about 250 nucleotides. The nucleic acid may have a length of at least 10, 11, 12, 13, 14, 15, 16, 17, 18, 19, 20, 21, 22, 23, 24, 25, 26, 27, 28, 29, 30, 35, 40, 45, 50, 60, 70, 80, 90, 100, 125, 150, 175, 200 or 250 nucleotides. The nucleic acid may be synthesized or expressed in a cell (in vitro or in vivo) using a synthetic gene described herein. The nucleic acid may be synthesized as a single-strand molecule and hybridized to a substantially complementary nucleic acid to form a duplex. The nucleic acid may be introduced to a cell, tissue or organ in a single- or double-stranded form or capable of being expressed by a synthetic gene using methods well known to those skilled in the art, including as described in U.S. Pat. No. 6,506,559, which is incorporated herein by reference.

TABLE 1

SEQ ID NOS of miRs, forward primers and MGB probes

| Sanger miR name | miR SEQ ID NO: | FW primer SEQ ID NO: | MGB probe SEQ ID NO: |
|---|---|---|---|
| hsa-let-7b | 1 | 50 | 99 |
| hsa-let-7f | 2 | 51 | 100 |
| hsa-miR-106a | 3 | 52 | 101 |
| hsa-miR-10a | 4 | 53 | 102 |
| hsa-miR-10b | 5 | 54 | 103 |
| hsa-miR-122 | 6 | 55 | 104 |
| hsa-miR-124 | 7 | 56 | 105 |
| hsa-miR-125b | 8 | 57 | 106 |
| hsa-miR-126 | 9 | 58 | 107 |
| hsa-miR-128 | 10 | 59 | 108 |

TABLE 1-continued

SEQ ID NOS of miRs, forward primers and MGB probes

| Sanger miR name | miR SEQ ID NO: | FW primer SEQ ID NO: | MGB probe SEQ ID NO: |
|---|---|---|---|
| hsa-miR-130a | 11 | 60 | 109 |
| hsa-miR-138 | 12 | 61 | 110 |
| hsa-miR-142-3p | 13 | 62 | 111 |
| hsa-miR-143 | 14 | 63 | 112 |
| hsa-miR-146a | 15 | 64 | 113 |
| hsa-miR-146b-5p | 16 | 65 | 114 |
| hsa-miR-148b | 17 | 66 | 115 |
| hsa-miR-152 | 18 | 67 | 116 |
| hsa-miR-15b | 19 | 68 | 117 |
| hsa-miR-185 | 20 | 69 | 118 |
| hsa-miR-192 | 21 | 70 | 119, 120 |
| hsa-miR-193a-3p | 22 | 71 | 121 |
| hsa-miR-19b | 23 | 72 | 122 |
| hsa-miR-200a | 24 | 73 | 123 |
| hsa-miR-200b | 25 | 74 | 124 |
| hsa-miR-200c | 26 | 75 | 125, 126 |
| hsa-miR-205 | 27 | 76 | 127 |
| hsa-miR-20a | 28 | 77 | 128 |
| hsa-miR-21 | 29 | 78 | 129 |
| hsa-miR-210 | 30 | 79 | 130 |
| hsa-miR-221 | 31 | 80 | 131 |
| hsa-miR-222 | 32 | 81 | 132 |
| hsa-miR-25 | 33 | 82 | 133 |
| hsa-miR-29a | 34 | 83 | 134 |
| hsa-miR-29b | 35 | 84 | 135 |
| hsa-miR-29c | 36 | 85 | 136 |
| hsa-miR-30a | 37 | 86 | 137 |
| hsa-miR-31 | 38 | 87 | 138 |
| hsa-miR-342-3p | 39 | 88 | 139 |
| hsa-miR-345 | 40 | 89 | 140 |
| hsa-miR-372 | 41 | 90 | 141 |
| hsa-miR-375 | 42 | 91 | 142 |
| hsa-miR-378 | 43 | 92 | 143 |
| hsa-miR-425 | 44 | 93 | 144 |
| hsa-miR-451 | 45 | 94 | 145 |
| hsa-miR-497 | 46 | 95 | 146 |
| hsa-miR-9* | 47 | 96 | 147 |
| hsa-mir-92b | 48 | 97 | 148 |
| hsa-miR-509-3p | 49 | 150 | 151 |
| U6 |  | 98 | 149 |

Sanger miR name: the miRBase registry name (release 9-12)

3. Nucleic Acid Complexes

The nucleic acid may further comprise one or more of the following: a peptide, a protein, a RNA-DNA hybrid, an antibody, an antibody fragment, a Fab fragment, and an aptamer.

4. Pri-miRNA

The nucleic acid may comprise a sequence of a pri-miRNA or a variant thereof. The pri-miRNA sequence may comprise from 45-30,000, 50-25,000, 100-20,000, 1,000-1,500 or 80-100 nucleotides. The sequence of the pri-miRNA may comprise a pre-miRNA, miRNA and miRNA*, as set forth herein, and variants thereof. The sequence of the pri-miRNA may comprise any of the sequences of SEQ ID NOS: 1-49 or variants thereof.

The pri-miRNA may comprise a hairpin structure. The hairpin may comprise a first and a second nucleic acid sequence that are substantially complimentary. The first and second nucleic acid sequence may be from 37-50 nucleotides. The first and second nucleic acid sequence may be separated by a third sequence of from 8-12 nucleotides. The hairpin structure may have a free energy of less than −25 Kcal/mole, as calculated by the Vienna algorithm with default parameters, as described in Hofacker et al. (Monatshefte f. Chemie 1994; 125:167-188), the contents of which are incorporated herein by reference. The hairpin may comprise a terminal loop of 4-20, 8-12 or 10 nucleotides. The pri-miRNA may comprise at least 19% adenosine nucleotides, at least 16% cytosine nucleotides, at least 23% thymine nucleotides and at least 19% guanine nucleotides.

5. Pre-miRNA

The nucleic acid may also comprise a sequence of a pre-miRNA or a variant thereof. The pre-miRNA sequence may comprise from 45-90, 60-80 or 60-70 nucleotides. The sequence of the pre-miRNA may comprise a miRNA and a miRNA* as set forth herein. The sequence of the pre-miRNA may also be that of a pri-miRNA excluding from 0-160 nucleotides from the 5' and 3' ends of the pri-miRNA. The sequence of the pre-miRNA may comprise the sequence of SEQ ID NOS: 1-49 or variants thereof.

6. miRNA

The nucleic acid may also comprise a sequence of a miRNA (including miRNA*) or a variant thereof. The miRNA sequence may comprise from 13-33, 18-24 or 21-23 nucleotides. The miRNA may also comprise a total of at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 nucleotides. The sequence of the miRNA may be the first 13-33 nucleotides of the pre-miRNA. The sequence of the miRNA may also be the last 13-33 nucleotides of the pre-miRNA. The sequence of the miRNA may comprise the sequence of SEQ ID NOS: 1-49 or variants thereof 7. Probes A probe comprising a nucleic acid described herein is also provided. Probes may be used for screening and diagnostic methods, as outlined below. The probe may be attached or immobilized to a solid substrate, such as a biochip.

The probe may have a length of from 8 to 500, 10 to 100 or 20 to 60 nucleotides. The probe may also have a length of at least 8, 9, 10, 11, 12, 13, 14, 15, 16, 17, 18, 19, 20, 21, 22, 23, 24, 25, 26, 27, 28, 29, 30, 35, 40, 45, 50, 60, 70, 80, 90, 100, 120, 140, 160, 180, 200, 220, 240, 260, 280 or 300 nucleotides. The probe may further comprise a linker sequence of from 10-60 nucleotides. The probe may comprise a nucleic acid that is complementary to a sequence selected from the group consisting of SEQ ID NOS: 1-49 or variants thereof. The probe may comprise a sequence selected from the group consisting of SEQ ID NOS: 99-149 and 151.

8. Biochip

A biochip is also provided. The biochip may comprise a solid substrate comprising an attached probe or plurality of probes described herein. The probes may be capable of hybridizing to a target sequence under stringent hybridization conditions. The probes may be attached at spatially defined addresses on the substrate. More than one probe per target sequence may be used, with either overlapping probes or probes to different sections of a particular target sequence. The probes may be capable of hybridizing to target sequences associated with a single disorder appreciated by those in the art. The probes may either be synthesized first, with subsequent attachment to the biochip, or may be directly synthesized on the biochip.

The solid substrate may be a material that may be modified to contain discrete individual sites appropriate for the attachment or association of the probes and is amenable to at least one detection method. Representative examples of substrates include glass and modified or functionalized glass, plastics (including acrylics, polystyrene and copolymers of styrene and other materials, polypropylene, polyethylene, polybutylene, polyurethanes, TeflonJ, etc.), polysaccharides, nylon or nitrocellulose, resins, silica or silica-based materials including silicon and modified silicon, carbon, metals, inorganic glasses and plastics. The substrates may allow optical detection without appreciably fluorescing.

The substrate may be planar, although other configurations of substrates may be used as well. For example, probes may be placed on the inside surface of a tube, for flow-through sample analysis to minimize sample volume. Similarly, the substrate may be flexible, such as flexible foam, including closed cell foams made of particular plastics.

The biochip and the probe may be derivatized with chemical functional groups for subsequent attachment of the two. For example, the biochip may be derivatized with a chemical functional group including, but not limited to, amino groups, carboxyl groups, oxo groups or thiol groups. Using these functional groups, the probes may be attached using functional groups on the probes either directly or indirectly using a linker. The probes may be attached to the solid support by either the 5' terminus, 3' terminus, or via an internal nucleotide.

The probe may also be attached to the solid support non-covalently. For example, biotinylated oligonucleotides can be made, which may bind to surfaces covalently coated with streptavidin, resulting in attachment. Alternatively, probes may be synthesized on the surface using techniques such as photopolymerization and photolithography.

9. Diagnostics

As used herein, the term "diagnosing" refers to classifying pathology, or a symptom, determining a severity of the pathology (grade or stage), monitoring pathology progression, forecasting an outcome of pathology and/or prospects of recovery.

As used herein, the phrase "subject in need thereof" refers to an animal or human subject who is known to have cancer, at risk of having cancer (e.g., a genetically predisposed subject, a subject with medical and/or family history of cancer, a subject who has been exposed to carcinogens, occupational hazard, environmental hazard) and/or a subject who exhibits suspicious clinical signs of cancer (e.g., blood in the stool or melena, unexplained pain, sweating, unexplained fever, unexplained loss of weight up to anorexia, changes in bowel habits (constipation and/or diarrhea), tenesmus (sense of incomplete defecation, for rectal cancer specifically), anemia and/or general weakness). Additionally or alternatively, the subject in need thereof can be a healthy human subject undergoing a routine well-being check up.

Analyzing presence of malignant or pre-malignant cells can be effected in vivo or ex vivo, whereby a biological sample (e.g., biopsy) is retrieved. Such biopsy samples comprise cells and may be an incisional or excisional biopsy. Alternatively, the cells may be retrieved from a complete resection.

While employing the present teachings, additional information may be gleaned pertaining to the determination of treatment regimen, treatment course and/or to the measurement of the severity of the disease.

As used herein the phrase "treatment regimen" refers to a treatment plan that specifies the type of treatment, dosage, schedule and/or duration of a treatment provided to a subject in need thereof (e.g., a subject diagnosed with a pathology). The selected treatment regimen can be an aggressive one which is expected to result in the best clinical outcome (e.g., complete cure of the pathology) or a more moderate one which may relieve symptoms of the pathology yet results in incomplete cure of the pathology. It will be appreciated that in certain cases the treatment regimen may be associated with some discomfort to the subject or adverse side effects (e.g., damage to healthy cells or tissue). The type of treatment can include a surgical intervention (e.g., removal of lesion, diseased cells, tissue, or organ), a cell replacement therapy, an administration of a therapeutic drug (e.g., receptor agonists, antagonists, hormones, chemotherapy agents) in a local or a systemic mode, an exposure to radiation therapy using an external source (e.g., external beam) and/or an internal source (e.g., brachytherapy) and/or any combination thereof. The dosage, schedule and duration of treatment can vary, depending on the severity of pathology and the selected type of treatment, and those of skill in the art are capable of adjusting the type of treatment with the dosage, schedule and duration of treatment.

A method of diagnosis is also provided. The method comprises detecting an expression level of a specific cancer-associated nucleic acid in a biological sample. The sample may be derived from a patient. Diagnosis of a specific cancer state in a patient may allow for prognosis and selection of therapeutic strategy. Further, the developmental stage of cells may be classified by determining temporarily expressed specific cancer-associated nucleic acids.

In situ hybridization of labeled probes to tissue arrays may be performed. When comparing the fingerprints between individual samples the skilled artisan can make a diagnosis, a prognosis, or a prediction based on the findings. It is further understood that the nucleic acid sequence which indicate the diagnosis may differ from those which indicate the prognosis and molecular profiling of the condition of the cells may lead to distinctions between responsive or refractory conditions or may be predictive of outcomes.

10. Kits

A kit is also provided and may comprise a nucleic acid described herein together with any or all of the following: assay reagents, buffers, probes and/or primers, and sterile saline or another pharmaceutically acceptable emulsion and suspension base. In addition, the kits may include instructional materials containing directions (e.g., protocols) for the practice of the methods described herein. The kit may further comprise a software package for data analysis of expression profiles.

For example, the kit may be a kit for the amplification, detection, identification or quantification of a target nucleic acid sequence. The kit may comprise a poly (T) primer, a forward primer, a reverse primer, and a probe.

Any of the compositions described herein may be comprised in a kit. In a non-limiting example, reagents for isolating miRNA, labeling miRNA, and/or evaluating a miRNA population using an array are included in a kit. The kit may further include reagents for creating or synthesizing miRNA probes. The kits will thus comprise, in suitable container means, an enzyme for labeling the miRNA by incorporating labeled nucleotide or unlabeled nucleotides that are subsequently labeled. It may also include one or more buffers, such as reaction buffer, labeling buffer, washing buffer, or a hybridization buffer, compounds for preparing the miRNA probes, components for in situ hybridization and components for isolating miRNA. Other kits of the invention may include components for making a nucleic acid array comprising miRNA, and thus may include, for example, a solid support.

The following examples are presented in order to more fully illustrate some embodiments of the invention. They should, in no way be construed, however, as limiting the broad scope of the invention.

EXAMPLES

Methods

1. Tumor Samples 903 tumor samples took part in the study. These included 252 that were part of a preliminary study and 651 additional formalin-fixed paraffin-embedded (FFPE) samples. Tumor samples were obtained from several sources. Institutional review approvals were obtained for all samples in accordance with each institute's institutional review board or IRB equivalent guidelines. Samples included primary tumors and metastases of defined origins, according to clinical records. Tumor content was at least 50% for >95% of samples, as determined by a pathologist based on hematoxylin-eosin (H&E) stained slides. 204 of the 903 samples were used only in the validation phase, as an independent blinded test set. The reference diagnosis of these samples from the original clinical record was confirmed by an additional review of pathological specimens.

2. RNA Extraction

For FFPE samples, total RNA was isolated from seven to ten 10-m-thick tissue sections using the miR extraction protocol developed at Rosetta Genomics. Briefly, the sample was incubated a few times in xylene at 57° C. to remove paraffin excess, followed by ethanol washes. Proteins were degraded by proteinase K solution at 45° C. for a few hours. The RNA was extracted with acid phenol:chloroform followed by ethanol precipitation and DNAse digestion. Total RNA quantity and quality was checked by spectrophotometer (Nanodrop ND-1000).

3. miR Array Platform

Custom microarrays (Agilent Technologies, Santa Clara, Calif.) were produced by printing DNA oligonucleotide probes to more than 900 human microRNAs. Each probe, printed in triplicate, carried up to 22-nucleotide (nt) linker at the 3' end of the microRNA's complement sequence, in addition to an amine group used to couple the probes to coated glass slides. Twenty μM of each probe were dissolved in 2×SSC+0.0035% SDS and spotted in triplicate on Schott Nexterion® Slide E-coated microarray slides using a Genomic Solutions® BioRobotics MicroGrid II according the MicroGrid manufacturer's directions. Fifty-four negative control probes were designed using the sense sequences of different microRNAs. Two groups of positive control probes were designed to hybridize to miR array: (i) synthetic small RNAs were spiked to the RNA before labeling to verify the labeling efficiency; and (ii) probes for abundant small RNA (e.g., small nuclear RNAs (U43, U49, U24, Z30, U6, U48, U44), 5.8s and 5s ribosomal RNA) are spotted on the array to verify RNA quality. The slides were blocked in a solution containing 50 mM ethanolamine, 1 M Tris (pH9.0) and 0.1% SDS for 20 min at 500 C, then thoroughly rinsed with water and spun dry.

4. Cy-Dye Labeling of miRNA for miR Array

Five μg of total RNA were labeled by ligation (Thomson et al. Nature Methods 2004; 1:47-53) of an RNA-linker, p-rCrU-Cy/dye (Dharmacon), to the 3' end with Cy3 or Cy5. The labeling reaction contained total RNA, spikes (0.1-20 fmoles), 300 ng RNA-linker-dye, 15% DMSO, 1× ligase buffer and 20 units of T4 RNA ligase (NEB), and proceeded at 4° C. for 1 h, followed by 1 h at 37° C. The labeled RNA was mixed with 3× hybridization buffer (Ambion), heated to 95° C. for 3 min and then added on top of the miR array. Slides were hybridized for 12-16 h at 42° C., followed by two washes at room temperature with 1×SSC and 0.2% SDS and a final wash with 0.1×SSC.

Arrays were scanned using an Agilent Microarray Scanner Bundle G2565BA (resolution of 10 μm at 100% power). Array images were analyzed using SpotReader software (Niles Scientific).

5. Array Signal Calculation and Normalization

Triplicate spots were combined to produce one signal for each probe by taking the logarithmic mean of reliable spots. All data were log-transformed (natural base) and the analysis was performed in log-space. A reference data vector for normalization R was calculated by taking the median expression level for each probe across all samples. For each sample data vector S, a 2nd degree polynomial F was found so as to provide the best fit between the sample data and the reference data, such that R≈F(S). Remote data points ("outliers") were not used for fitting the polynomial F. For each probe in the sample (element Si in the vector S), the normalized value (in log-space) Mi was calculated from the initial value Si by transforming it with the polynomial function F, so that Mi=F(Si). Data were translated back to linear-space (by taking the exponent). Using only the training set samples to generate the reference data vector did not affect the results.

6. Logistic Regression

The aim of a logistic regression model is to use several features, such as expression levels of several microRNAs, to assign a probability of belonging to one of two possible groups, such as two branches of a node in a binary decision-tree. Logistic regression models the natural log of the odds ratio, i.e., the ratio of the probability of belonging to the first group, for example, the left branch in a node of a binary decision-tree (P) over the probability of belonging to the second group, for example, the right branch in such a node (1-P), as a linear combination of the different expression levels (in log-space). The logistic regression assumes that:

$$\ln\left(\frac{P}{1-P}\right) = \beta_0 + \sum_{i=1}^{N} \beta_i \cdot M_i = \beta_0 + \beta_1 \cdot M_1 + \beta_2 \cdot M_2 + \ldots,$$

where $\beta_0$ is the bias, $M_i$ is the expression level (normalized, in log-space) of the i-th microRNA used in the decision node, and $\beta_i$ is its corresponding coefficient. $\beta i > 0$ indicates that the probability to take the left branch (P) increases when the expression level of this microRNA (Mi) increases, and the opposite for $\beta i < 0$. If a node uses only a single microRNA (M) then solving for P results in:

$$P = \frac{e^{\beta_0 + \beta_1 \cdot M}}{1 + e^{\beta_0 + \beta_1 \cdot M}}.$$

The regression error on each sample is the difference between the assigned probability P and the true "probability" of this sample, i.e., 1 if this sample is in the left branch group and 0 otherwise. The training and optimization of the logistic regression model calculates the parameters β and the p-values (for each microRNA by the Wald statistic and for the overall model by the $\chi^2$ (chi-square) difference), maximizing the likelihood of the data given the model and minimizing the total regression error $$\sum_{\substack{Samples \\ in \\ first \\ group}} (1 - P_j) + \sum_{\substack{Samples \\ in \\ second \\ group}} P_j.$$

The probability output of the logistic model is here converted to a binary decision by comparing P to a threshold, denoted by $P_{TH}$, i.e., if $P > P_{TH}$ then the sample belongs to the left branch ("first group") and vice versa. Choosing at each node the branch which has a probability>0.5, i.e., using a probability threshold of 0.5, leads to a minimization of the sum of the regression errors. However, as the goal was the minimization of the overall number of misclassifications (and not of their probability), a modification which adjusts the probability threshold ($P_{TH}$) was used in order to minimize the overall number of mistakes at each node (Table 3). For each node the threshold to a new probability threshold $P_{TH}$ was optimized such that the number of classification errors is minimized. This change of probability threshold is equivalent (in terms of classifications) to a modification of the bias $\beta_0$, which may reflect a change in the prior frequencies of the classes.

7. Stepwise Logistic Regression and Feature Selection

The original data contain the expression levels of multiple microRNAs for each sample, i.e., multiple of data features. In training the classifier for each node, only a small subset of these features was selected and used for optimizing a logistic regression model. In the initial training this was done using a forward stepwise scheme. The features were sorted in order of decreasing log-likelihoods, and the logistic model was started off and optimized with the first feature. The second feature was then added, and the model re-optimized. The regression error of the two models was compared: if the addition of the feature did not provide a significant advantage (a $\chi 2$ difference less than 7.88, p-value of 0.005), the new feature was discarded. Otherwise, the added feature was kept. Adding a new feature may make a previous feature redundant (e.g., if they are very highly correlated). To check for this, the process iteratively checks if the feature with lowest likelihood can be discarded (without losing $\chi 2$ difference as above). After ensuring that the current set of features is compact in this sense, the process continues to test the next feature in the sorted list, until features are exhausted. No limitation on the number of feature was inserted into the algorithm, but in most cases 2-3 features were selected.

The stepwise logistic regression method was used on subsets of the training set samples by re-sampling the training set with repetition ("bootstrap"), so that each of the 20 runs contained about two-thirds of the samples at least once, and any one sample had >99% chance of being left out at least once. This resulted in an average of 2-3 features per node (4-8 in more difficult nodes). A robust set of 2-3 features per each node was selected (Table 3) by comparing features that were repeatedly chosen in the bootstrap sets to previous evidence, and considering their signal strengths and reliability. When using these selected features to construct the classifier, the stepwise process was not used and the training optimized the logistic regression model parameters only.

8. K-Nearest-Neighbors (KNN) Classification Algorithm

The KNN algorithm (see e.g., Ma et al., Arch Pathol Lab Med 2006; 130:465-73) calculated the distance (Pearson correlation) of any sample to all samples in the training set, and classifies the sample by the majority vote of the k samples which are most similar (k being a parameter of the classifier). The correlation is calculated on the pre-defined set of microRNAs (the 48 microRNAs that were used by the decision-tree). KNN algorithms with k=1; 10 were compared, and the optimal performer was selected, using k=7.

9. qRT-PCR

Total RNA (1 µg) is subjected to polyadenylation reaction as described before (Gilad et al., PLoS ONE 2008; 3:e3148). Briefly, RNA is incubated in the presence of poly (A) polymerase (PAP) (Takara-2180A), MnC12, and ATP for 1 h at 37° C. Reverse transcription is performed on the total RNA. An oligodT primer harboring a consensus sequence (complementary to the reverse primer, oligodT starch, an N nucleotide (a mixture of all A, C, and G) and V nucleotide (mixture of four nucleotides) was used for the reverse transcription reaction. The primer was first annealed to the polyA-RNA and then subjected to a reverse transcription reaction of SuperScript II RT (Invitrogen). The cDNA was then amplified by a real-time PCR reaction, using a microRNA-specific forward primer, TaqMan probe and universal reverse primer that is complementary to the 3' sequence of the oligo dT tail. The reactions were incubated for 10 min at 95° C., followed by 42 cycles of 95° C. for 15 s and 60° C. for 1 min. qRT-PCR was performed using probes for the 104 candidate microRNAs, of which 5 were tested with two different forward primers, and for U6 snoRNA.

10. Feature Selection and Training

The training samples were kept with average Ct below 36 and at least 30 microRNAs detected (Ct<38). Each sample was normalized by subtracting from the Ct of each microRNA the average Ct of all microRNAs of the sample, and adding back a scaling constant (the average Ct over the entire sample set). Feature selection and classifier training were using the scaled Ct as the input signal. The feature selection resulted in a set of 48 microRNAs. The decision-tree (FIG. 1) used logistic regression on combinations of two-to-three microRNAs in each node to make binary decisions. The KNN was based on comparing the expression of all 48 microRNAs in each sample to all other samples in the training database. The decision-tree and KNN each return a predicted tissue of origin and histological type where applicable. The classifier returns the two different predictions or a single consensus prediction if the predictions concur. When the decision-tree and KNN predict different histological types of the same tissue of origin, the tissue of origin is returned as a consensus prediction with no histological type indicated.

11. Test Protocol

RNA was extracted in batches together with a negative control. The negative control was a no-RNA sample that served to detect potential contaminations, and should not give any signal in the PCR reaction. The extracted RNA, together with a positive control sample, underwent cDNA preparation and 48 microRNAs were measured by qRT-PCR in duplicates in one 96-well plate per sample. The positive control was a specific RNA sample that should meet defined Ct ranges in the assay. Quality assessment of each well was based on the fluorescence amplification curve, using thresholds on the maximal fluorescence and the linear slope as a function of the measured Ct. For each microRNA, CtmiR was calculated by taking the average Ct of the two repeats. Quality assessment for each sample was based on the number and identity of expressed microRNAs (Ct<38) and the average Ct of the measured microRNAs. CtmiR values for each sample were normalized by rescaling as described above. The rescaled values were used as input to the classifier that was trained using qRT-PCR data (as described above).

Example 1

Samples and Profiling

A discovery process that profiled hundreds of samples on the array platforms was performed to identify candidate biomarkers. A training set of ~400 FFPE samples was used. RNA was extracted from these samples and qRT-PCR was preformed. An assay was constructed using 48 microRNAs (Table 3; FIGS. 1-7), to differentiate between 26 classes representing 18 tissue origins. An alternative assay was constructed, which does not identify bladder as an origin, i.e., differentiates between 25 classes representing 17 tissue origins.

A validation set of 255 new FFPE tumor samples was used to assess the performance of the assay, representing 26 different tumor origins or "classes" (see Table 2 for a summary of samples). About half of the samples in the set were metastatic tumors to different sites (e.g., lung, bone, brain and liver). Tumor percentage was at least 50% for all samples in the set.

TABLE 2

Cancer types, classes and histology

| Class | Cancer types and histological classifications |
|---|---|
| 1 bladder | transitional cell carcinoma |
| 2 biliary tract | cholangiocarcinoma, gallbladder adenocarcinoma |
| 3 brain-astrocytoma | astrocytic tumor; astrocytic tumor, anaplastic astrocytoma; astrocytic tumor, glioblastoma multiforme |
| 4 brain-oligodendroglioma | oligodendroglial tumor, anaplastic oligodendroglioma; oligodendroglial tumor, oligodendroglioma |
| 5 breast | adenocarcinoma; invasive ductal carcinoma |
| 6 colon | adenocarcinoma |
| 7 esophagus-squamous | squamous cell carcinoma |
| 8 esophagus-stomach | esophagus adenocarcinoma; stomach adenocarcinoma |
| 9 head & neck | squamous cell carcinoma of the larynx, pharynx and nose |
| 10 kidney | renal cell carcinoma; clear cell carcinoma |
| 11 liver | hepatocellular carcinoma |
| 12 lung-carcinoid | neuroendocrine, carcinoid |
| 13 lung-squamous | NSCLC, squamous cell carcinoma |
| 14 lung-adeno-large | non-small, adenocarcinoma; non-small, large cell carcinoma |
| 15 lung-small | neuroendocrine, small |
| 16 melanoma | malignant melanoma |
| 17 ovary-serous | ovary serous adenocarcinoma |
| 18 ovary-endometrioid | ovary endometrioid adenocarcinoma |
| 19 pancreas | adenocarcinoma |
| 20 prostate | adenocarcinoma |
| 21 testis-seminoma | GCT; seminoma |
| 22 testis-non-seminoma | GCT; non-seminoma |
| 23 thymus | thymoma-type B2; thymoma-type B3 |
| 24 thyroid-follicular | follicular carcinoma |
| 25 thyroid-medullary | neuroendocrine; medullary |
| 26 thyroid-papillary | papillary carcinoma; tall cell |

Example 2

Decision-Tree Classification Algorithm

Figure 1B:
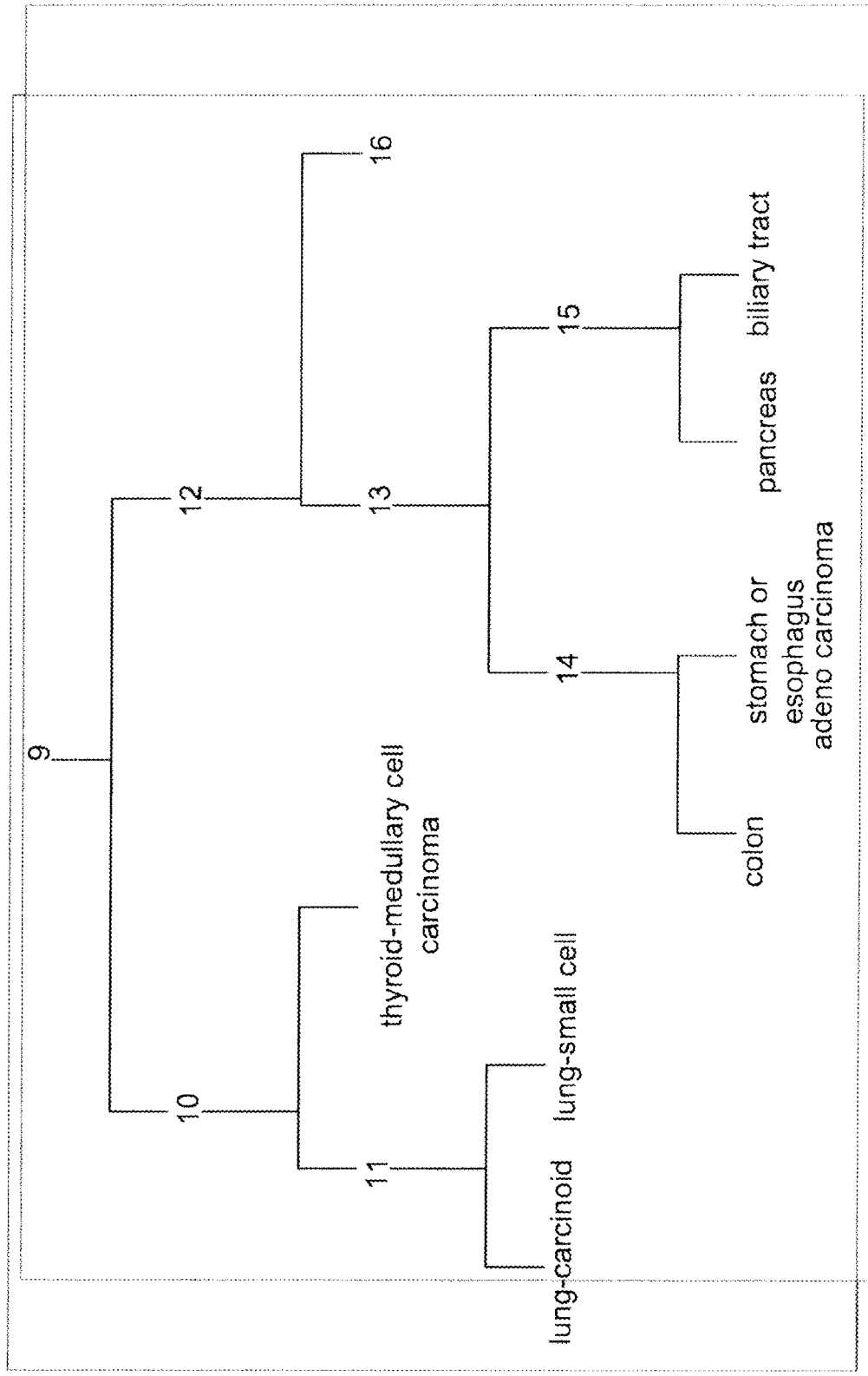
Figure 1C:
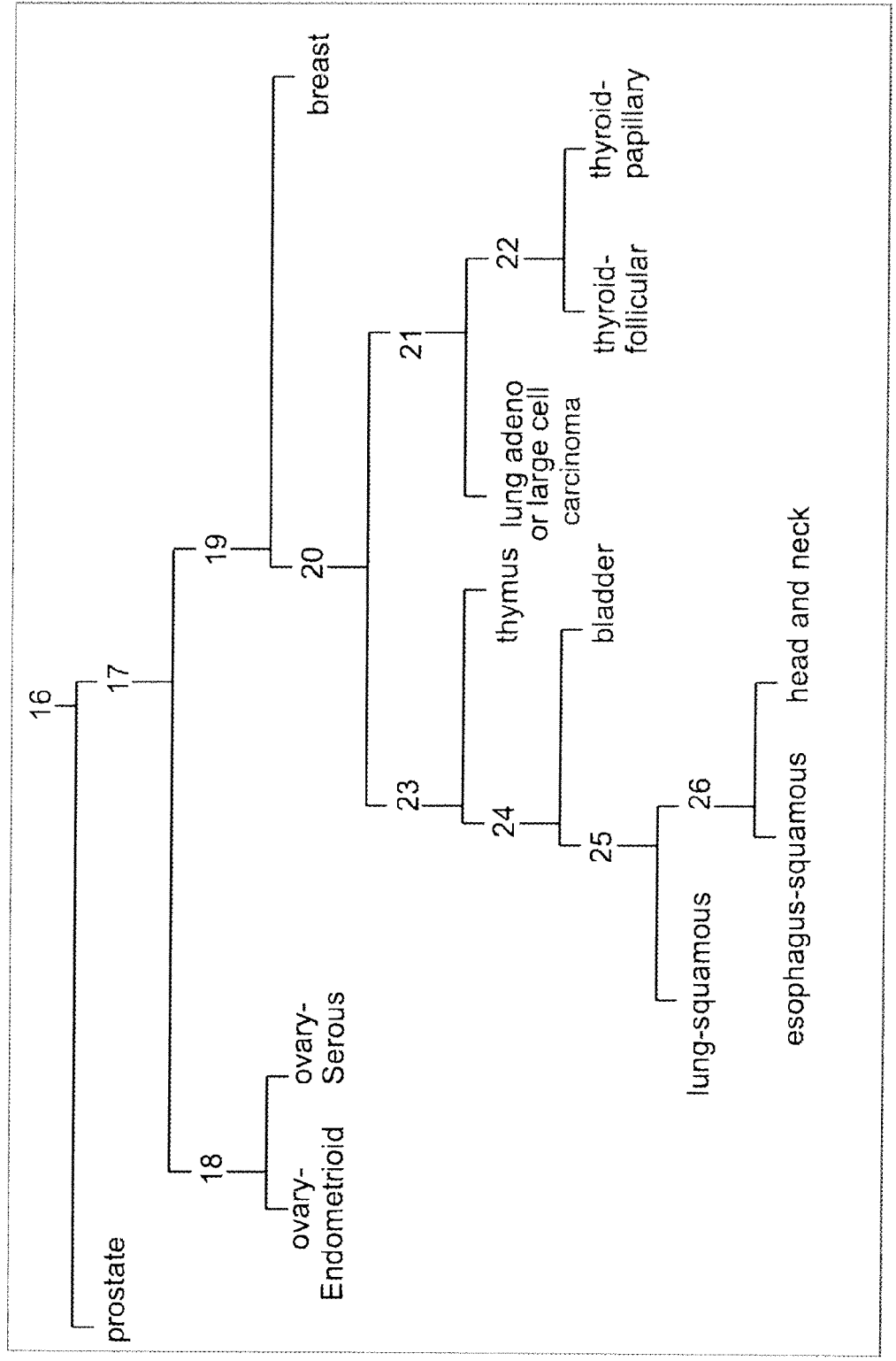

A tumor classifier was built using the microRNA expression levels by applying a binary tree classification scheme (FIG. 1). This framework is set up to utilize the specificity of microRNAs in tissue differentiation and embryogenesis: different microRNAs are involved in various stages of tissue specification, and are used by the algorithm at different decision points or "nodes." The tree breaks up the complex multitissue classification problem into a set of simpler binary decisions. At each node, classes which branch out earlier in the tree are not considered, reducing interference from irrelevant samples and further simplifying the decision. The decision at each node can then be accomplished using only a small number of microRNA biomarkers, which have well-defined roles in the classification (Table 3). The structure of the binary tree was based on a hierarchy of tissue development and morphological similarity[8], which was modified by prominent features of the microRNA expression patterns. For example, the expression patterns of microRNAs indicated a significant difference between liver-cholangio tumors and tumors of non-liver origin, and these are therefore separated at node #1 (FIG. 2) into separate branches (FIG. 1).

For each of the individual nodes logistic regression models were used, a robust family of classifiers which are frequently used in epidemiological and clinical studies to combine continuous data features into a binary decision (FIGS. 2-7 and Methods). Since gene expression classifiers have an inherent redundancy in selecting the gene features, we used bootstrapping on the training sample set as a method to select a stable microRNA set for each node (Methods). This resulted in a small number (usually 2-3) of microRNA features per node, totaling 48 microRNAs for the full classifier (Table 3). This approach provides a systematic process for identifying new biomarkers for differential expression.

Example 3

Defining High-Confidence Classifications

In clinical practice it is often useful to assess information of different degrees of confidence[17,18]. In the diagnosis of tumor origin in particular, a short list of highly probable possibilities is a practical option when no definite diagnosis can be made. Since the decision-tree and the KNN algorithms are designed differently and trained independently, improved accuracy and greater confidence can be obtained by combining and comparing their classifications. When the two classifiers agree, the diagnosis is considered high-confidence and a single origin is identified. When the two disagree, the classification is made with low-confidence and two origins are suggested. Sensitivity of the union refers to the percentage in which at least one of the classifiers (Tree and KLAN) was correct.

Example 4

Performance of the Test in Blinded Validation

The test performance was assessed using an independent set of 204 validation samples. These archival samples included primary as well as metastatic tumor samples, preserved as FFPE blocks, whose original clinical diagnosis ("reference diagnosis") was one of the origins on which the classifier was trained. The samples were processed by personnel who were blinded to the original reference diagnosis for these samples, and classifications were automatically generated by dedicated software. 16 of the 204 samples (8%) failed QA criteria. For 188 samples (92%), including 87 metastatic tumor samples (46% of the samples), the test was completed successfully and produced tissue-of-origin predictions. For 159 of these samples (84%), the reference diagnosis for tissue of origin was predicted by at least one of the two classifiers (Table 4). For 124 samples (66%), the two classifiers agreed, generating a consensus prediction for a single tissue-of-origin. For these single-prediction cases, the sensitivity (positive agreement) was 90% (111/124 of the classifications agreed with the reference diagnosis), and it exceeded 90% for most tissue-types. Specificity (negative agreement) in this group ranged from 94% to 100%.

FFPE sections from 73 of the validation samples were processed independently and blindly in a second laboratory. Data and classifications for these samples were compared between the two laboratories. The mean correlation for the qRT-PCR signals was 0.979 (4 samples had correlation coefficients between 0.91 and 0.95, all other correlations were greater than 0.95). The two labs disagreed on only 4 samples. For another 8, they had one of two answers in common and for the remaining 61, classifications matched perfectly between the two laboratories, demonstrating the precision of the test.

TABLE 3

Nodes of the decision-tree and microRNAs (# SEQ ID NO.) used in each node

| Node Num | Left Node Num Or Class | Right Node Num Or Class | Node miR 1 | Node miR 2 | Node miR3 | Node Beta 0 | Node Beta 1 | Node Beta 2 | Node Beta 3 | Node All Classes Right |
|---|---|---|---|---|---|---|---|---|---|---|
| 1 | 2 | 3 | hsa-miR-200c (#26) | hsa-miR-122 (#6) | — | 9.11E+01 | 4.42E+00 | −8.39E+00 | NaN | biliary tract carcinoma, liver |
| 2 | liver | biliary tract carcinoma | hsa-miR-200b (#25) | hsa-miR-126 (#9) | — | −3.10E+03 | 6.76E+01 | 2.48E+01 | NaN | liver |
| 3 | 4 | 5 | hsa-miR-372 (#41) | — | — | 5.34E+02 | −1.56E+01 | NaN | NaN | testis-non-seminoma, testis-seminoma |
| 4 | testis-non-seminoma | testis-seminoma | hsa-miR-451 (#45) | hsa-miR-221 (#31) | hsa-miR-92b (#48) | −6.13E+02 | −2.10E+01 | −1.59E+01 | 5.68E+01 | testis-non-seminoma |
| 5 | 9 | 6 | hsa-miR-148b (#17) | hsa-miR-200c (#26) | — | 1.18E+02 | 1.63E+00 | −5.26E+00 | NaN | biliary tract carcinoma, bladder, breast, colon, esophagus-squamous, head_neck, lung-adeno large, lung-carcinoid, lung-small_cell, lung-squamous, ovary-endometrioid, ovary-serous, pancreas, prostate, stomach/esophagus-adeno, thymus, thyroid-follicular, thyroid-medullary, thyroid-papillary |
| 6 | melanoma | 7 | hsa-miR-497 (#46) | hsa-miR-146a (#15) | — | −6.61E+02 | 3.58E+01 | −1.54E+01 | NaN | melanoma |
| 7 | 8 | kidney | hsa-miR-9* (#47) | hsa-miR-124 (#7) | — | 6.66E+02 | −1.02E+01 | −8.88E+00 | NaN | brain-astrocytoma, brain-oligodendroglioma |
| 8 | brain-astrocytoma | brain-oligodendroglioma | hsa-miR-497 (#46) | hsa-miR-128 (#10) | — | −3.99E+03 | 7.04E+01 | 5.75E+01 | NaN | brain-astrocytoma |
| 9 | 10 | 12 | hsa-miR-15b (#19) | hsa-miR-152 (#18) | hsa-miR-375 (#42) | 2.56E+01 | −1.20E+00 | 1.29E+00 | −1.22E+00 | lung-carcinoid, lung-small cell, thyroid-medullary |
| 10 | 11 | thyroid-medullary | hsa-miR-222 (#32) | hsa-miR-200a (#24) | — | −3.52E+02 | 2.97E+01 | −1.89E+01 | NaN | lung-carcinoid, lung-small cell |
| 11 | lung-carcinoid | lung-small cell | hsa-miR-106a (#3) | hsa-miR-29c (#36) | — | 2.53E+02 | 2.36E+01 | −3.12E+01 | NaN | lung-carcinoid |
| 12 | 13 | 16 | hsa-miR-106a (#3) | hsa-miR-192 (#21) | — | 7.25E+01 | 3.73E−01 | −2.38E+00 | NaN | Biliary tract carcinoma, colon, pancreas, stomach/esophagus-adeno |
| 13 | 14 | 15 | hsa-miR-21 (#29) | hsa-let-7b (#1) | hsa-miR-30a (#37) | −1.40E+02 | 1.90E−01 | 3.33E+00 | 1.18E+00 | colon, stomach/esophagus-adeno |
| 14 | colon | Stomach esophagus-adeno | hsa-miR-10a (#4) | hsa-miR-92b (#48) | hsa-miR-29a-fw18 (#34) | 9.31E+02 | −1.18E+01 | 1.32E+01 | −3.37E+01 | colon |
| 15 | pancreas | biliary tract carcinoma | hsa-miR-25 (#33) | hsa-miR-200c (#26) | hsa-miR-20a-fw18 (#28) | −2.06E+02 | 9.37E+00 | −6.45E+00 | 3.10E+00 | pancreas |
| 16 | prostate | 17 | hsa-miR-185 (#20) | hsa-miR-375 (#42) | — | 2.68E+02 | 8.84E+00 | −2.10E+01 | NaN | prostate |
| 17 | 18 | 19 | hsa-miR-10b-fw18 (#5) | hsa-miR-130a (#11) | hsa-miR-210 (#30) | 1.35E+02 | −1.53E+00 | −1.63E+00 | −8.83E−01 | ovary-endometrioid, ovary-serous |
| 18 | ovary-endometrioid | ovary-serous | hsa-miR-148b (#17) | hsa-miR-193a-3p (#22) | hsa-let-7f (#2) | −3.81E+02 | 3.64E+00 | 4.26E+00 | 3.38E+00 | ovary-endometrioid |

TABLE 3-continued

Nodes of the decision-tree and microRNAs (# SEQ ID NO.) used in each node

| Node Num | Left Node Num Or Class | Right Node Num Or Class | Node miR 1 | Node miR 2 | Node miR3 | Node Beta 0 | Node Beta 1 | Node Beta 2 | Node Beta 3 | Node All Classes Right |
|---|---|---|---|---|---|---|---|---|---|---|
| 19 | 20 | breast | hsa-miR-193a-3p (#22) | hsa-miR-342-3p (#39) | — | −1.32E+02 | 2.26E+00 | 1.66E+00 | NaN | bladder, esophagus-squamous, head/neck, lung-adeno large, lung-squamous, thymus, thyroid-follicular, thyroid-papillary |
| 20 | 23 | 21 | hsa-miR-205 (#27) | hsa-miR-146b-5p (#16) | — | −2.02E+01 | −1.22E+00 | 1.82E+00 | NaN | bladder, esophagus-squamous, head/neck, lung-squamous, thymus |
| 21 | lung-adeno large | 22 | hsa-miR-125b (#8) | hsa-miR-30a (#37) | — | −3.03E+03 | 3.93E+01 | 6.02E+01 | NaN | lung-adeno large |
| 22 | thyroid-follicular | thyroid-papillary | hsa-miR-31 (#38) | hsa-miR-21 (#29) | — | −1.53E+03 | 2.78E+01 | 2.17E+01 | NaN | thyroid-follicular |
| 23 | 24 | thymus | hsa-miR-29b (#35) | hsa-miR-21 (#29) | — | −9.24E+01 | 5.39E+00 | −2.98E+00 | NaN | bladder, esophagus-squamous, head/neck, lung-squamous |
| 24 | 25 | bladder | hsa-miR-425 (#44) | hsa-miR-10a (#4) | hsa-miR-375 (#42) | −9.03E+01 | 2.70E+00 | 1.79E+00 | −1.73E+00 | esophagus-squamous, head/neck, lung-squamous |
| 25 | lung-squamous | 26 | hsa-miR-10a (#4) | hsa-miR-19b (#23) | hsa-miR-222 (#32) | 2.52E+02 | −2.10E+00 | −3.19E+00 | −2.50E+00 | lung-squamous |
| 26 | esophagus-squamous | head/neck | hsa-miR-143 (#14) | hsa-miR-451 (#45) | hsa-miR-30a (#37) | −1.32E+02 | −1.75E+01 | 4.47E+00 | 1.53E+01 | esophagus-squamous |

Node Num The number of the node (1-26)
Left Node Num Or Class Left branch - the node number or the class reached
Right Node Num Or Class Right branch - the node number or the class reached
Node miR1 miRs used in node - #1
Node miR2 miRs used in node - #2 (could be empty)
Node miR3 miRs used in node - #3 (could be empty)
Node Beta 0 The value of the beta0 (intercept)
Node Beta 1 The value of the beta1, corresponding to nodeMir1
Node Beta 2 The value of the beta2, corresponding to nodeMir2 - could be NaN (empty)
Node Beta 3 The value of the beta3, corresponding to nodeMir3 - could be NaN (empty)
Node All Classes Left A list of all the classes that are on the left branch
Node All Classes Right A list of all the classes that are on the right branch

TABLE 4

Performance of the test in blinded validation

| Class | Successful samples in test set | Sensitivity of union prediction | Specificity of union prediction | Fraction in high confidence | Sensitivity of high confidence | Specificity of high confidence |
|---|---|---|---|---|---|---|
| Biliary tract | 6 | 66.67 | 93.96 | 33.33 | 100 | 98.36 |
| Brain | 10 | 100 | 100 | 80 | 100 | 100 |
| Breast | 33 | 66.67 | 93.55 | 45.45 | 53.33 | 100 |
| Colon | 9 | 88.89 | 94.41 | 66.67 | 83.33 | 99.15 |
| Esophagus | 1 | 100 | 98.4 | 0 | NaN | 100 |
| Head & Neck | 3 | 100 | 92.43 | 100 | 100 | 97.52 |
| Kidney | 8 | 87.5 | 99.44 | 62.5 | 80 | 100 |
| Liver | 8 | 100 | 99.44 | 100 | 100 | 100 |
| Lung | 23 | 91.3 | 84.85 | 86.96 | 95 | 94.23 |
| Melanocyte | 7 | 85.71 | 97.79 | 85.71 | 83.33 | 100 |
| Ovary | 13 | 84.62 | 100 | 38.46 | 100 | 100 |
| Pancreas | 6 | 50 | 97.8 | 16.67 | 100 | 99.19 |
| Prostate | 19 | 89.47 | 99.41 | 57.89 | 100 | 100 |
| Stomach or esophagus | 5 | 40 | 98.91 | 40 | 50 | 100 |
| Testis | 7 | 100 | 100 | 100 | 100 | 100 |

TABLE 4-continued

Performance of the test in blinded validation

| Class | Successful samples in test set | Sensitivity of union prediction | Specificity of union prediction | Fraction in high confidence | Sensitivity of high confidence | Specificity of high confidence |
|---|---|---|---|---|---|---|
| Thymus | 6 | 83.33 | 97.8 | 83.33 | 80 | 100 |
| Thyroid | 24 | 100 | 98.17 | 83.33 | 100 | 100 |
| Total | 188 | 84.57 | 96.91 | 65.96 | 89.52 | 99.34 |

Example 5

Classification Example

One of the training-set samples originally diagnosed in the clinical setting as a metastatic tumor to the brain originating from the lung, was classified by the tree (in leave-one-out cross-validation) as originating from the liver. This classification was traced back to node #1, the branching point where lung and liver origins diverge (FIG. 1). This node uses hsa-miR-122 (SEQ ID NO: 6), together with hsa-miR-200c (SEQ ID NO: 26). The expression of these microRNAs in this sample, in particular the very high expression of hsa-miR-122 (FIG. 8A), are strong indicators of a possible hepatic origin of this sample. Upon re-examination of the clinical record, it was found that this sample was originally classified as a lung metastasis based on the fact that the patient had a known mass in the lung. This disagreement between the original clinical diagnosis and our test was followed up by blinded pathological review. Indeed, the sample's immunohistochemical staining pattern was incompatible with lung adenocarcinoma origin, but was consistent with a diagnosis of hepatocellular carcinoma (FIG. 8B). Thus, the test could suggest an alternative diagnosis for this patient, namely a primary hepatocellular carcinoma with metastatic spread to both lung and brain.

Example 6

Variant microRNAs

For some of the microRNAs in Table 3, other variant microRNAs having a similar seed sequence (identical nucleotides 2-8) are known in the human genome (see Table 5), and are therefore considered to target a very similar set of (mRNA-coding) genes (via the RISC machinery). These microRNAs with identical seed sequence may be substituted for the indicated miRs.

TABLE 5 microRNAs with identical seed sequence

| Indicated miRs | Seed | miRs with same seed | miR sequence | SEQ ID NO: |
|---|---|---|---|---|
| hsa-let-7b | GAGGTAG | hsa-let-7d | AGAGGTAGTAGGTTGCATAGTT | 152 |
|  | GAGGTAG | hsa-let-7e | TGAGGTAGGAGGTTGTATAGTT | 153 |
|  | GAGGTAG | hsa-miR-98 | TGAGGTAGTAAGTTGTATTGTT | 154 |
|  | GAGGTAG | hsa-let-7f | TGAGGTAGTAGATTGTATAGTT | 2 |
|  | GAGGTAG | hsa-let-7a | TGAGGTAGTAGGTTGTATAGTT | 155 |
|  | GAGGTAG | hsa-let-7c | TGAGGTAGTAGGTTGTATGGTT | 156 |
|  | GAGGTAG | hsa-let-7g | TGAGGTAGTAGTTTGTACAGTT | 157 |
|  | GAGGTAG | hsa-let-7i | TGAGGTAGTAGTTTGTGCTGTT | 158 |
| hsa-let-7f | GAGGTAG | hsa-let-7d | AGAGGTAGTAGGTTGCATAGTT | 152 |
|  | GAGGTAG | hsa-let-7e | TGAGGTAGGAGGTTGTATAGTT | 153 |
|  | GAGGTAG | hsa-miR-98 | TGAGGTAGTAAGTTGTATTGTT | 154 |
|  | GAGGTAG | hsa-let-7a | TGAGGTAGTAGGTTGTATAGTT | 155 |
|  | GAGGTAG | hsa-let-7c | TGAGGTAGTAGGTTGTATGGTT | 156 |
|  | GAGGTAG | hsa-let-7b | TGAGGTAGTAGGTTGTGTGGTT | 1 |
|  | GAGGTAG | hsa-let-7g | TGAGGTAGTAGTTTGTACAGTT | 157 |
|  | GAGGTAG | hsa-let-7i | TGAGGTAGTAGTTTGTGCTGTT | 158 |
| hsa-miR-106a | AAAGTGC | hsa-miR-519d | CAAAGTGCCTCCCTTTAGAGTG | 159 |
|  | AAAGTGC | hsa-miR-20b | CAAAGTGCTCATAGTGCAGGTAG | 160 |
|  | AAAGTGC | hsa-miR-93 | CAAAGTGCTGTTCGTGCAGGTAG | 161 |
|  | AAAGTGC | hsa-miR-17 | CAAAGTGCTTACAGTGCAGGTAG | 162 |
|  | AAAGTGC | hsa-miR-526b* | GAAAGTGCTTCCTTTTAGAGGC | 163 |
|  | AAAGTGC | hsa-miR-106b | TAAAGTGCTGACAGTGCAGAT | 164 |
|  | AAAGTGC | hsa-miR-20a | TAAAGTGCTTATAGTGCAGGTAG | 28 |
| hsa-miR-10a | ACCCTGT | hsa-miR-10b | TACCCTGTAGAACCGAATTTGTG | 165 |
| hsa-miR-10b | ACCCTGT | hsa-miR-10a | TACCCTGTAGATCCGAATTTGTG | 4 |
| hsa-miR-124 | AAGGCAC | hsa-miR-506 | TAAGGCACCCTTCTGAGTAGA | 166 |
| hsa-miR-125b | CCCTGAG | hsa-miR-125a-5p | TCCCTGAGACCCTTTAACCTGTGA | 167 |

TABLE 5-continued microRNAs with identical seed sequence

| Indicated miRs | Seed | miRs with same seed | miR sequence | SEQ ID NO: |
|---|---|---|---|---|
| hsa-miR-130a | AGTGCAA | hsa-miR-301a | CAGTGCAATAGTATTGTCAAAGC | 168 |
| | AGTGCAA | hsa-miR-301b | CAGTGCAATGATATTGTCAAAGC | 169 |
| | AGTGCAA | hsa-miR-130b | CAGTGCAATGATGAAAGGGCAT | 170 |
| | AGTGCAA | hsa-miR-454 | TAGTGCAATATTGCTTATAGGGT | 171 |
| hsa-miR-146a | GAGAACT | hsa-miR-146b-5p | TGAGAACTGAATTCCATAGGCT | 16 |
| hsa-miR-146b-5p | GAGAACT | hsa-miR-146a | TGAGAACTGAATTCCATGGGTT | 15 |
| hsa-miR-148b | CAGTGCA | hsa-miR-148a | TCAGTGCACTACAGAACTTTGT | 172 |
| | CAGTGCA | hsa-miR-152 | TCAGTGCATGACAGAACTTGG | 18 |
| hsa-miR-152 | CAGTGCA | hsa-miR-148a | TCAGTGCACTACAGAACTTTGT | 172 |
| | CAGTGCA | hsa-miR-148b | TCAGTGCATCACAGAACTTTGT | 17 |
| hsa-miR-15b | AGCAGCA | hsa-miR-424 | CAGCAGCAATTCATGTTTTGAA | 173 |
| | AGCAGCA | hsa-miR-497 | CAGCAGCACACTGTGGTTTGT | 46 |
| | AGCAGCA | hsa-miR-195 | TAGCAGCACAGAAATATTGGC | 174 |
| | AGCAGCA | hsa-miR-15a | TAGCAGCACATAATGGTTTGTG | 175 |
| | AGCAGCA | hsa-miR-16 | TAGCAGCACGTAAATATTGGCG | 176 |
| hsa-miR-192 | TGACCTA | hsa-miR-215 | ATGACCTATGAATTGACAGAC | 177 |
| hsa-miR-193a-3p | ACTGGCC | hsa-miR-193b | AACTGGCCCTCAAAGTCCCGCT | 178 |
| hsa-miR-19b | GTGCAAA | hsa-miR-19a | TGTGCAAATCTATGCAAAACTGA | 179 |
| hsa-miR-200a | AACACTG | hsa-miR-141 | TAACACTGTCTGGTAAAGATGG | 180 |
| hsa-miR-200b | AATACTG | hsa-miR-200c | TAATACTGCCGGGTAATGATGGA | 26 |
| hsa-miR-200b | AATACTG | hsa-miR-429 | TAATACTGTCTGGTAAAACCGT | 181 |
| hsa-miR-200c | AATACTG | hsa-miR-200b | TAATACTGCCTGGTAATGATGA | 25 |
| | AATACTG | hsa-miR-429 | TAATACTGTCTGGTAAAACCGT | 181 |
| hsa-miR-20a | AAAGTGC | hsa-miR-106a | AAAAGTGCTTACAGTGCAGGTAG | 3 |
| | AAAGTGC | hsa-miR-519d | CAAAGTGCCTCCCTTTAGAGTG | 159 |
| | AAAGTGC | hsa-miR-20b | CAAAGTGCTCATAGTGCAGGTAG | 160 |
| | AAAGTGC | hsa-miR-93 | CAAAGTGCTGTTCGTGCAGGTAG | 161 |
| | AAAGTGC | hsa-miR-17 | CAAAGTGCTTACAGTGCAGGTAG | 162 |
| | AAAGTGC | hsa-miR-526b* | GAAAGTGCTTCCTTTTAGAGGC | 163 |
| | AAAGTGC | hsa-miR-106b | TAAAGTGCTGACAGTGCAGAT | 164 |
| hsa-miR-21 | AGCTTAT | hsa-miR-590-5p | GAGCTTATTCATAAAAGTGCAG | 182 |
| hsa-miR-221 | GCTACAT | hsa-miR-222 | AGCTACATCTGGCTACTGGGT | 32 |
| hsa-miR-222 | GCTACAT | hsa-miR-221 | AGCTACATTGTCTGCTGGGTTTC | 31 |
| hsa-miR-25 | ATTGCAC | hsa-miR-363 | AATTGCACGGTATCCATCTGTA | 184 |
| | ATTGCAC | hsa-miR-367 | AATTGCACTTTAGCAATGGTGA | 185 |
| | ATTGCAC | hsa-miR-32 | TATTGCACATTACTAAGTTGCA | 186 |
| | ATTGCAC | hsa-miR-92b | TATTGCACTCGTCCCGGCCTCC | 48 |
| | ATTGCAC | hsa-miR-92a | TATTGCACTTGTCCCGGCCTGT | 187 |
| hsa-miR-29a | AGCACCA | hsa-miR-29b | TAGCACCATTTGAAATCAGTGTT | 35 |
| | AGCACCA | hsa-miR-29c | TAGCACCATTTGAAATCGGTTA | 36 |
| hsa-miR-29b | AGCACCA | hsa-miR-29a | TAGCACCATCTGAAATCGGTTA | 34 |
| | AGCACCA | hsa-miR-29c | TAGCACCATTTGAAATCGGTTA | 36 |
| hsa-miR-29c | AGCACCA | hsa-miR-29a | TAGCACCATCTGAAATCGGTTA | 34 |
| | AGCACCA | hsa-miR-29b | TAGCACCATTTGAAATCAGTGTT | 35 |
| hsa-miR-30a | GTAAACA | hsa-miR-30d | TGTAAACATCCCCGACTGGAAG | 188 |
| | GTAAACA | hsa-miR-30b | TGTAAACATCCTACACTCAGCT | 189 |
| | GTAAACA | hsa-miR-30c | TGTAAACATCCTACACTCTCAGC | 190 |
| | GTAAACA | hsa-miR-30e | TGTAAACATCCTTGACTGGAAG | 191 |

TABLE 5-continued microRNAs with identical seed sequence

| Indicated miRs | Seed | miRs with same seed | miR sequence | SEQ ID NO: |
|---|---|---|---|---|
| hsa-miR-372 | AAGTGCT | hsa-miR-520a-3p | AAAGTGCTTCCCTTTGGACTGT | 192 |
|  | AAGTGCT | hsa-miR-520b | AAAGTGCTTCCTTTTAGAGGG | 193 |
|  | AAGTGCT | hsa-miR-520c-3p | AAAGTGCTTCCTTTTAGAGGGT | 194 |
|  | AAGTGCT | hsa-miR-520e | AAAGTGCTTCCTTTTTGAGGG | 195 |
|  | AAGTGCT | hsa-miR-520d-3p | AAAGTGCTTCTCTTTGGTGGGT | 196 |
|  | AAGTGCT | hsa-miR-373 | GAAGTGCTTCGATTTTGGGGTGT | 197 |
|  | AAGTGCT | hsa-miR-302e | TAAGTGCTTCCATGCTT | 198 |
|  | AAGTGCT | hsa-miR-302c | TAAGTGCTTCCATGTTTCAGTGG | 199 |
|  | AAGTGCT | hsa-miR-302d | TAAGTGCTTCCATGTTTGAGTGT | 200 |
|  | AAGTGCT | hsa-miR-302b | TAAGTGCTTCCATGTTTTAGTAG | 201 |
|  | AAGTGCT | hsa-miR-302a | TAAGTGCTTCCATGTTTTGGTGA | 202 |
| hsa-miR-378 | CTGGACT | hsa-miR-422a | ACTGGACTTAGGGTCAGAAGGC | 203 |
| hsa-miR-497 | AGCAGCA | hsa-miR-424 | CAGCAGCAATTCATGTTTTGAA | 173 |
|  | AGCAGCA | hsa-miR-195 | TAGCAGCACAGAAATATTGGC | 174 |
|  | AGCAGCA | hsa-miR-15a | TAGCAGCACATAATGGTTTGTG | 175 |
|  | AGCAGCA | hsa-miR-15b | TAGCAGCACATCATGGTTTACA | 19 |
|  | AGCAGCA | hsa-miR-16 | TAGCAGCACGTAAATATTGGCG | 176 |
| hsa-miR-92b | ATTGCAC | hsa-miR-363 | AATTGCACGGTATCCATCTGTA | 184 |
|  | ATTGCAC | hsa-miR-367 | AATTGCACTTTAGCAATGGTGA | 185 |
|  | ATTGCAC | hsa-miR-25 | CATTGCACTTGTCTCGGTCTGA | 33 |
|  | ATTGCAC | hsa-miR-32 | TATTGCACATTACTAAGTTGCA | 186 |
|  | ATTGCAC | hsa-miR-92a | TATTGCACTTGTCCCGGCCTGT | 187 |

For some of the microRNAs in Table 3, other microRNAs that are known in the human genome are located in close proximity on the genome (genomic cluster) (see Table 6), and are co-transcribed with the indicated miRs. These microRNAs from nearly the same genomic location may be substituted for the indicated miRs.

TABLE 6 microRNAs within the same genomic cluster

| Indicated miRs | miRs within the same genomic cluster | miR sequence | SEQ ID NO: |
|---|---|---|---|
| hsa-let-7b | hsa-let-7a | TGAGGTAGTAGGTTGTATAGTT | 155 |
|  | hsa-let-7a* | CTATACAATCTACTGTCTTTC | 204 |
|  | hsa-let-7b* | CTATACAACCTACTGCCTTCCC | 205 |
| hsa-let-7f | hsa-let-7a* | CTATACAATCTACTGTCTTTC | 204 |
|  | hsa-let-7a | TGAGGTAGTAGGTTGTATAGTT | 155 |
|  | hsa-let-7d | AGAGGTAGTAGGTTGCATAGTT | 152 |
|  | hsa-let-7d* | CTATACGACCTGCTGCCTTTCT | 206 |
|  | hsa-let-7f-1* | CTATACAATCTATTGCCTTCCC | 207 |
|  | hsa-let-7f-2* | CTATACAGTCTACTGTCTTTCC | 208 |
|  | hsa-miR-98 | TGAGGTAGTAAGTTGTATTGTT | 154 |
| hsa-miR-106a | hsa-miR-19b-2* | AGTTTTGCAGGTTTGCATTTCA | 209 |
|  | hsa-miR-20b | CAAAGTGCTCATAGTGCAGGTAG | 160 |
|  | hsa-miR-20b* | ACTGTAGTATGGGCACTTCCAG | 210 |
|  | hsa-miR-363 | AATTGCACGGTATCCATCTGTA | 184 |
|  | hsa-miR-363* | CGGGTGGATCACGATGCAATTT | 211 |
|  | hsa-miR-92a | TATTGCACTTGTCCCGGCCTGT | 187 |
|  | hsa-miR-92a-2* | GGGTGGGGATTTGTTGCATTAC | 212 |
|  | hsa-miR-106a* | CTGCAATGTAAGCACTTCTTAC | 213 |
|  | hsa-miR-18b | TAAGGTGCATCTAGTGCAGTTAG | 214 |
|  | hsa-miR-18b* | TGCCCTAAATGCCCCTTCTGGC | 215 |
|  | hsa-miR-19b | TGTGCAAATCCATGCAAAACTGA | 23 |
| hsa-miR-10a | hsa-miR-10a* | CAAATTCGTATCTAGGGGAATA | 216 |
| hsa-miR-10b | hsa-miR-10b* | ACAGATTCGATTCTAGGGGAAT | 217 |
| hsa-miR-122 | hsa-miR-122* | AACGCCATTATCACACTAAATA | 218 |
| hsa-miR-124 | hsa-miR-124* | CGTGTTCACAGCGGACCTTGAT | 219 |

TABLE 6-continued microRNAs within the same genomic cluster

| Indicated miRs | miRs within the same genomic cluster | miR sequence | SEQ ID NO: |
|---|---|---|---|
| hsa-miR-125b | hsa-miR-125b-1* | ACGGGTTAGGCTCTTGGGAGCT | 220 |
| | hsa-miR-125b-2* | TCACAAGTCAGGCTCTTGGGAC | 221 |
| | hsa-miR-99a | AACCCGTAGATCCGATCTTGTG | 222 |
| | hsa-miR-99a* | CAAGCTCGCTTCTATGGGTCTG | 223 |
| | hsa-miR-100 | AACCCGTAGATCCGAACTTGTG | 224 |
| | hsa-miR-100* | CAAGCTTGTATCTATAGGTATG | 225 |
| | hsa-let-7a | TGAGGTAGTAGGTTGTATAGTT | 155 |
| | hsa-let-7c | TGAGGTAGTAGGTTGTATGGTT | 156 |
| | hsa-let-7c* | TAGAGTTACACCCTGGGAGTTA | 226 |
| hsa-miR-126 | hsa-miR-126* | CATTATTACTTTTGGTACGCG | 227 |
| hsa-miR-130a | hsa-miR-130a* | TTCACATTGTGCTACTGTCTGC | 228 |
| hsa-miR-138 | hsa-miR-138-1* | GCTACTTCACAACACCAGGGCC | 229 |
| | hsa-miR-138-2* | GCTATTTCACGACACCAGGGTT | 230 |
| hsa-miR-142-3p | hsa-miR-142-5p | CATAAAGTAGAAAGCACTACT | 231 |
| hsa-miR-143 | hsa-miR-143* | GGTGCAGTGCTGCATCTCTGGT | 232 |
| | hsa-miR-145 | GTCCAGTTTTCCCAGGAATCCCT | 233 |
| | hsa-miR-145* | GGATTCCTGGAAATACTGTTCT | 234 |
| hsa-miR-146a | hsa-miR-146a* | CCTCTGAAATTCAGTTCTTCAG | 235 |
| hsa-miR-146b-5p | hsa-miR-146b-3p | TGCCCTGTGGACTCAGTTCTGG | 236 |
| hsa-miR-148b | hsa-miR-148b* | AAGTTCTGTTATACACTCAGGC | 237 |
| hsa-miR-15b | hsa-miR-15b* | CGAATCATTATTTGCTGCTCTA | 238 |
| | hsa-miR-16 | TAGCAGCACGTAAATATTGGCG | 176 |
| | hsa-miR-16-2* | CCAATATTACTGTGCTGCTTTA | 239 |
| hsa-miR-185 | hsa-miR-185* | AGGGGCTGGCTTTCCTCTGGTC | 240 |
| | hsa-miR-1306 | ACGTTGGCTCTGGTGGTG | 241 |
| hsa-miR-192 | hsa-miR-192* | CTGCCAATTCCATAGGTCACAG | 242 |
| | hsa-miR-194 | TGTAACAGCAACTCCATGTGGA | 243 |
| | hsa-miR-194* | CCAGTGGGGCTGCTGTTATCTG | 244 |
| hsa-miR-193a-3p | hsa-miR-193a-5p | TGGGTCTTTGCGGGCGAGATGA | 245 |
| | hsa-miR-365 | TAATGCCCCTAAAAATCCTTAT | 246 |
| hsa-miR-19b | hsa-miR-19a | TGTGCAAATCTATGCAAAACTGA | 179 |
| | hsa-miR-19a* | AGTTTTGCATAGTTGCACTACA | 247 |
| | hsa-miR-18a | TAAGGTGCATCTAGTGCAGATAG | 248 |
| | hsa-miR-18a* | ACTGCCCTAAGTGCTCCTTCTGG | 249 |
| | hsa-miR-18b | TAAGGTGCATCTAGTGCAGTTAG | 214 |
| | hsa-miR-18b* | TGCCCTAAATGCCCCTTCTGGC | 215 |
| | hsa-miR-17 | CAAAGTGCTTACAGTGCAGGTAG | 162 |
| | hsa-miR-17* | ACTGCAGTGAAGGCACTTGTAG | 250 |
| | hsa-miR-106a | AAAAGTGCTTACAGTGCAGGTAG | 3 |
| | hsa-miR-106a* | CTGCAATGTAAGCACTTCTTAC | 213 |
| | hsa-miR-20a* | ACTGCATTATGAGCACTTAAAG | 251 |
| | hsa-miR-20b | CAAAGTGCTCATAGTGCAGGTAG | 160 |
| | hsa-miR-20b* | ACTGTAGTATGGGCACTTCCAG | 210 |
| | hsa-miR-363 | AATTGCACGGTATCCATCTGTA | 184 |
| | hsa-miR-363 * | CGGGTGGATCACGATGCAATTT | 211 |
| | hsa-miR-92a | TATTGCACTTGTCCCGGCCTGT | 187 |
| | hsa-miR-92a-1* | AGGTTGGGATCGGTTGCAATGCT | 252 |
| | hsa-miR-92a-2* | GGGTGGGGATTTGTTGCATTAC | 212 |
| | hsa-miR-19b-1* | AGTTTTGCAGGTTTGCATCCAGC | 253 |
| | hsa-miR-19b-2* | AGTTTTGCAGGTTTGCATTTCA | 209 |
| | hsa-miR-20a | TAAAGTGCTTATAGTGCAGGTAG | 28 |
| hsa-miR-200a | hsa-miR-200b* | CATCTTACTGGGCAGCATTGGA | 254 |
| | hsa-miR-429 | TAATACTGTCTGGTAAAACCGT | 181 |
| | hsa-miR-200a* | CATCTTACCGGACAGTGCTGGA | 255 |
| | hsa-miR-200b | TAATACTGCCTGGTAATGATGA | 25 |
| hsa-miR-200b | hsa-miR-200a | TAACACTGTCTGGTAACGATGTT | 24 |
| | hsa-miR-200a* | CATCTTACCGGACAGTGCTGGA | 255 |
| | hsa-miR-200b* | CATCTTACTGGGCAGCATTGGA | 254 |
| | hsa-miR-429 | TAATACTGTCTGGTAAAACCGT | 181 |

TABLE 6-continued microRNAs within the same genomic cluster

| Indicated miRs | miRs within the same genomic cluster | miR sequence | SEQ ID NO: |
|---|---|---|---|
| hsa-miR-200c | hsa-miR-200c* | CGTCTTACCCAGCAGTGTTTGG | 256 |
| | hsa-miR-141 | TAACACTGTCTGGTAAAGATGG | 180 |
| | hsa-miR-141* | CATCTTCCAGTACAGTGTTGGA | 257 |
| hsa-miR-20a | hsa-miR-17* | ACTGCAGTGAAGGCACTTGTAG | 250 |
| | hsa-miR-17 | CAAAGTGCTTACAGTGCAGGTAG | 162 |
| | hsa-miR-18a* | ACTGCCCTAAGTGCTCCTTCTGG | 249 |
| | hsa-miR-18a | TAAGGTGCATCTAGTGCAGATAG | 248 |
| | hsa-miR-19a* | AGTTTTGCATAGTTGCACTACA | 247 |
| | hsa-miR-19a | TGTGCAAATCTATGCAAAACTGA | 179 |
| | hsa-miR-20a* | ACTGCATTATGAGCACTTAAAG | 251 |
| | hsa-miR-92a | TATTGCACTTGTCCCGGCCTGT | 187 |
| | hsa-miR-92a-1* | AGGTTGGGATCGGTTGCAATGCT | 252 |
| | hsa-miR-19b-1* | AGTTTTGCAGGTTTGCATCCAGC | 253 |
| | hsa-miR-19b | TGTGCAAATCCATGCAAAACTGA | 23 |
| hsa-miR-21 | hsa-miR-21* | CAACACCAGTCGATGGGCTGT | 258 |
| hsa-miR-221 | hsa-miR-221* | ACCTGGCATACAATGTAGATTT | 259 |
| | hsa-miR-222 | AGCTACATCTGGCTACTGGGT | 183 |
| | hsa-miR-222* | CTCAGTAGCCAGTGTAGATCCT | 260 |
| hsa-miR-222 | hsa-miR-221* | ACCTGGCATACAATGTAGATTT | 259 |
| | hsa-miR-222* | CTCAGTAGCCAGTGTAGATCCT | 260 |
| | hsa-miR-221 | AGCTACATTGTCTGCTGGGTTTC | 31 |
| hsa-miR-25 | hsa-miR-25* | AGGCGGAGACTTGGGCAATTG | 261 |
| | hsa-miR-93 | CAAAGTGCTGTTCGTGCAGGTAG | 161 |
| | hsa-miR-93 * | ACTGCTGAGCTAGCACTTCCCG | 262 |
| | hsa-miR-106b | TAAAGTGCTGACAGTGCAGAT | 164 |
| | hsa-miR-106b* | CCGCACTGTGGGTACTTGCTGC | 263 |
| hsa-miR-29a | hsa-miR-29a* | ACTGATTTCTTTTGGTGTTCAG | 264 |
| | hsa-miR-29b | TAGCACCATTTGAAATCAGTGTT | 35 |
| | hsa-miR-29b-1* | GCTGGTTTCATATGGTGGTTTAGA | 265 |
| hsa-miR-29b | hsa-miR-29a* | ACTGATTTCTTTTGGTGTTCAG | 264 |
| | hsa-miR-29b-1* | GCTGGTTTCATATGGTGGTTTAGA | 265 |
| | hsa-miR-29b-2* | CTGGTTTCACATGGTGGCTTAG | 266 |
| | hsa-miR-29c | TAGCACCATTTGAAATCGGTTA | 36 |
| | hsa-miR-29a | TAGCACCATCTGAAATCGGTTA | 34 |
| | hsa-miR-29c* | TGACCGATTTCTCCTGGTGTTC | 267 |
| hsa-miR-29c | hsa-miR-29b-2* | CTGGTTTCACATGGTGGCTTAG | 266 |
| | hsa-miR-29c* | TGACCGATTTCTCCTGGTGTTC | 267 |
| | hsa-miR-29b | TAGCACCATTTGAAATCAGTGTT | 35 |
| hsa-miR-30a | hsa-miR-30 a* | CTTTCAGTCGGATGTTTGCAGC | 268 |
| | hsa-miR-30c | TGTAAACATCCTACACTCTCAGC | 190 |
| | hsa-miR-30c-2* | CTGGGAGAAGGCTGTTTACTCT | 269 |
| hsa-miR-31 | hsa-miR-31* | TGCTATGCCAACATATTGCCAT | 270 |
| hsa-miR-342-3p | hsa-miR-342-5p | AGGGGTGCTATCTGTGATTGA | 271 |
| hsa-miR-372 | hsa-miR-371-3p | AAGTGCCGCCATCTTTTGAGTGT | 272 |
| | hsa-miR-371-5p | ACTCAAACTGTGGGGGCACT | 273 |
| | hsa-miR-373 | GAAGTGCTTCGATTTTGGGGTGT | 197 |
| | hsa-miR-373* | ACTCAAAATGGGGGCGCTTTCC | 274 |
| hsa-miR-378 | hsa-miR-378* | CTCCTGACTCCAGGTCCTGTGT | 275 |
| hsa-miR-425 | hsa-miR-425* | ATCGGGAATGTCGTGTCCGCCC | 276 |
| | hsa-miR-191 | CAACGGAATCCCAAAAGCAGCTG | 277 |
| | hsa-miR-191* | GCTGCGCTTGGATTTCGTCCCC | 278 |
| hsa-miR-451 | hsa-miR-144 | TACAGTATAGAT GAT GTACT | 279 |
| | hsa-miR-144* | GGATATCATCATATACTGTAAG | 280 |
| hsa-miR-497 | hsa-miR-195 | TAGCAGCACAGAAATATTGGC | 174 |
| | hsa-miR-195* | CCAATATTGGCTGTGCTGCTCC | 281 |
| | hsa-miR-497* | CAAACCACACTGTGGTGTTAGA | 282 |

TABLE 6-continued microRNAs within the same genomic cluster

| Indicated miRs | miRs within the same genomic cluster | miR sequence | SEQ ID NO: |
|---|---|---|---|
| hsa-miR-9* | hsa-miR-9 | TCTTTGGTTATCTAGCTGTATGA | 283 |
| hsa-miR-92b | hsa-miR-92b* | AGGGACGGGACGCGGTGCAGTG | 284 |

For some of the microRNAs in Table 3, other microRNAs that are known in the human genome have similar sequences (less than 6 mismatches in the sequence) (see Table 7), and may therefore also be captured by probes with the same design. These microRNAs with similar overall sequence may be substituted for the indicated miRs.

TABLE 7 microRNAs with similar sequence

| Indicated miRs | miRs in sequence cluster | Sequence | SEQ ID NO: |
|---|---|---|---|
| hsa-let-7b | hsa-let-7a | TGAGGTAGTAGGTTGTATAGTT | 155 |
|  | hsa-let-7e | TGAGGTAGGAGGTTGTATAGTT | 153 |
|  | hsa-let-7c | TGAGGTAGTAGGTTGTATGGTT | 156 |
|  | hsa-let-7f | TGAGGTAGTAGATTGTATAGTT | 2 |
|  | hsa-let-7d | AGAGGTAGTAGGTTGCATAGTT | 152 |
|  | hsa-miR-1827 | TGAGGCAGTAGATTGAAT | 285 |
|  | hsa-let-7g | TGAGGTAGTAGTTTGTACAGTT | 157 |
|  | hsa-miR-98 | TGAGGTAGTAAGTTGTATTGTT | 154 |
| hsa-let-7f | hsa-let-7b | TGAGGTAGTAGGTTGTGTGGTT | 1 |
|  | hsa-let-7c | TGAGGTAGTAGGTTGTATGGTT | 156 |
|  | hsa-miR-1827 | TGAGGCAGTAGATTGAAT | 285 |
|  | hsa-let-7g | TGAGGTAGTAGTTTGTACAGTT | 157 |
|  | hsa-miR-98 | TGAGGTAGTAAGTTGTATTGTT | 154 |
|  | hsa-let-7d | AGAGGTAGTAGGTTGCATAGTT | 152 |
|  | hsa-let-7e | TGAGGTAGGAGGTTGTATAGTT | 153 |
|  | hsa-let-7a | TGAGGTAGTAGGTTGTATAGTT | 155 |
| hsa-miR-106a | hsa-miR-17 | CAAAGTGCTTACAGTGCAGGTAG | 162 |
|  | hsa-miR-93 | CAAAGTGCTGTTCGTGCAGGTAG | 161 |
|  | hsa-miR-106b | TAAAGTGCTGACAGTGCAGAT | 164 |
|  | hsa-miR-20b | CAAAGTGCTCATAGTGCAGGTAG | 160 |
|  | hsa-miR-20a | TAAAGTGCTTATAGTGCAGGTAG | 28 |
| hsa-miR-10a | hsa-miR-10b | TACCCTGTAGAACCGAATTTGTG | 165 |
| hsa-miR-10b | hsa-miR-10a | TACCCTGTAGATCCGAATTTGTG | 4 |
| hsa-miR-130a | hsa-miR-130b | CAGTGCAATGATGAAAGGGCAT | 170 |
| hsa-miR-146a | hsa-miR-146b-5p | TGAGAACTGAATTCCATAGGCT | 16 |
| hsa-miR-146b-5p | hsa-miR-146a | TGAGAACTGAATTCCATGGGTT | 15 |
| hsa-miR-148b | hsa-miR-148a | TCAGTGCACTACAGAACTTTGT | 172 |
| hsa-miR-148b | hsa-miR-152 | TCAGTGCATGACAGAACTTGG | 18 |
| hsa-miR-152 | hsa-miR-148b | TCAGTGCATCACAGAACTTTGT | 17 |
|  | hsa-miR-148a | TCAGTGCACTACAGAACTTTGT | 172 |
| hsa-miR-15b | hsa-miR-15a | TAGCAGCACATAATGGTTTGTG | 175 |
| hsa-miR-192 | hsa-miR-215 | ATGACCTATGAATTGACAGAC | 177 |
| hsa-miR-193a-3p | hsa-miR-193b | AACTGGCCCTCAAAGTCCCGCT | 178 |
| hsa-miR-19b | hsa-miR-19a | TGTGCAAATCTATGCAAAACTGA | 179 |
| hsa-miR-200a | hsa-miR-141 | TAACACTGTCTGGTAAAGATGG | 180 |
| hsa-miR-200b | hsa-miR-200c | TAATACTGCCGGGTAATGATGGA | 26 |
| hsa-miR-200c | hsa-miR-200b | TAATACTGCCTGGTAATGATGA | 25 |

TABLE 7-continued microRNAs with similar sequence

| Indicated miRs | miRs in sequence cluster | Sequence | SEQ ID NO: |
|---|---|---|---|
| hsa-miR-20a | hsa-miR-106b | TAAAGTGCTGACAGTGCAGAT | 164 |
| | hsa-miR-20b | CAAAGTGCTCATAGTGCAGGTAG | 160 |
| | hsa-miR-93 | CAAAGTGCTGTTCGTGCAGGTAG | 161 |
| | hsa-miR-17 | CAAAGTGCTTACAGTGCAGGTAG | 162 |
| | hsa-miR-106a | AAAAGTGCTTACAGTGCAGGTAG | 3 |
| hsa-miR-29a | hsa-miR-29c | TAGCACCATTTGAAATCGGTTA | 36 |
| | hsa-miR-29b | TAGCACCATTTGAAATCAGTGTT | 35 |
| hsa-miR-29b | hsa-miR-29a | TAGCACCATCTGAAATCGGTTA | 34 |
| | hsa-miR-29c | TAGCACCATTTGAAATCGGTTA | 36 |
| hsa-miR-29c | hsa-miR-29b | TAGCACCATTTGAAATCAGTGTT | 35 |
| | hsa-miR-29a | TAGCACCATCTGAAATCGGTTA | 34 |
| hsa-miR-30a | hsa-miR-30d | TGTAAACATCCCCGACTGGAAG | 188 |
| | hsa-miR-30e | TGTAAACATCCTTGACTGGAAG | 191 |
| hsa-miR-378 | hsa-miR-422a | ACTGGACTTAGGGTCAGAAGGC | 203 |
| hsa-miR-92b | hsa-miR-92a | TATTGCACTTGTCCCGGCCTGT | 187 |

The foregoing description of the specific embodiments so fully reveals the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

It should be understood that the detailed description and specific examples, while indicating preferred embodiments of the invention, are given by way of illustration only, since various changes and modifications within the spirit and scope of the invention will become apparent to those skilled in the art from this detailed description.

REFERENCES

1. Bentwich, I. et al. Identification of hundreds of conserved and nonconserved human microRNAs. Nat Genet (2005).
2. Farh, K. K. et al. The Widespread Impact of Mammalian MicroRNAs on mRNA Repression and Evolution. Science (2005).
3. Griffiths-Jones, S., Grocock, R. J., van Dongen, S., Bateman, A. & Enright, A. J. miRBase: microRNA sequences, targets and gene nomenclature. Nucleic Acids Res 34, D140-4 (2006).
4. He, L. et al. A microRNA polycistron as a potential human oncogene. Nature 435, 828-33 (2005).
5. Baskerville, S. & Bartel, D. P. Microarray profiling of microRNAs reveals frequent coexpression with neighboring miRNAs and host genes. Rna 11, 241-7 (2005).
6. Landgraf, P. et al. A Mammalian microRNA Expression Atlas Based on Small RNA Library Sequencing. Cell 129, 1401-14 (2007).
7. Volinia, S. et al. A microRNA expression signature of human solid tumors defines cancer gene targets. Proc Natl Acad Sci USA (2006).
8. Lu, J. et al. MicroRNA expression profiles classify human cancers. Nature 435, 834-8 (2005).
9. Varadhachary, G. R., Abbruzzese, J. L. & Lenzi, R. Diagnostic strategies for unknown primary cancer. Cancer 100, 1776-85 (2004).
10. Pimiento, J. M., Teso, D., Malkan, A., Dudrick, S. J. & Palesty, J. A. Cancer of unknown primary origin: a decade of experience in a community-based hospital. Am J Surg 194, 833-7; discussion 837-8 (2007).
11. Shaw, P. H., Adams, R., Jordan, C. & Crosby, T. D. A clinical review of the investigation and management of carcinoma of unknown primary in a single cancer network. Clin Oncol (R Coll Radiol) 19, 87-95 (2007).
12. Hainsworth, J. D. & Greco, F. A. Treatment of patients with cancer of an unknown primary site. N Engl J Med 329, 257-63 (1993).
13. Blaszyk, H., Hartmann, A. & Bjornsson, J. Cancer of unknown primary: clinicopathologic correlations. Apmis 111, 1089-94 (2003).
14. Bloom, G. et al. Multi-platform, multi-site, microarray-based human tumor classification. Am J Pathol 164, 9-16 (2004).
15. Ma, X. J. et al. Molecular classification of human cancers using a 92-gene real-time quantitative polymerase chain reaction assay. Arch Pathol Lab Med 130, 465-73 (2006).
16. Talantov, D. et al. A quantitative reverse transcriptase-polymerase chain reaction assay to identify metastatic carcinoma tissue of origin. J Mol Diagn 8, 320-9 (2006).
17. Tothill, R. W. et al. An expression-based site of origin diagnostic method designed for clinical application to cancer of unknown origin. Cancer Res 65, 4031-40 (2005).
18. Shedden, K. A. et al. Accurate molecular classification of human cancers based on gene expression using a simple classifier with a pathological tree-based framework. Am J Pathol 163, 1985-95 (2003).
19. Raver-Shapira, N. et al. Transcriptional Activation of miR-34a Contributes to p53-Mediated Apoptosis. Mol Cell (2007).
20. Xiao, C. et al. MiR-150 Controls B Cell Differentiation by Targeting the Transcription Factor c-Myb. Cell 131, 146-59 (2007).

The invention claimed is:

1. A method of identifying a tissue of origin of a cancer sample, the method comprising:
   (a) obtaining a cancer sample from a subject, wherein said sample is of a primary cancer, a metastatic cancer, or a cancer of unknown primary origin;
   (b) determining an expression profile in said sample of nucleic acids comprising SEQ ID NOS: 1-48, wherein said determining an expression profile comprises contacting the sample with a primer comprising a sequence selected from the group consisting of SEQ ID NOs: 73, 74, and 75, or a sequence at least 90% identical thereto;
   (c) comparing said expression profile to a reference expression profile by using a classifier algorithm selected from the group consisting of a decision tree classifier, logistic regression classifier, nearest neighbor classifier, neural network classifier, Gaussian mixture model (GMM), Support Vector Machine (SVM) classifier, nearest centroid classifier, linear regression classifier and random forest classifier; whereby the altered expression of SEQ ID NOs: 1-48 relative to the reference expression profile allows the identification of the tissue of origin of said sample; and
   (d) identifying the tissue of origin of said sample based on the altered expression profile of SEQ ID NOs: 1-48 in said sample.

2. The method of claim 1, wherein said tissue is selected from the group consisting of liver, lung, bladder, prostate, breast, colon, ovary, testis, stomach, thyroid, pancreas, brain, head and neck, kidney, melanocytes, thymus, biliary tract and esophagus.

3. A method of identifying a tissue of origin of a cancer sample, the method comprising:
   (a) obtaining a cancer sample from a subject, wherein said sample is of a primary cancer, a metastatic cancer, or a cancer of unknown primary origin;
   (b) measuring the abundance in said sample of nucleic acids comprising SEQ ID NOS: 1-48, wherein said measuring the abundance comprises contacting the sample with a primer comprising a sequence selected from the group consisting of SEQ ID NOs: 73, 74, and 75, or a sequence at least 90% identical thereto;
   (c) comparing said obtained measurement of abundance to a reference abundance of SEQ ID NOs: 1-48 by using a classifier algorithm selected from the group consisting of a decision tree classifier, logistic regression classifier, nearest neighbor classifier, neural network classifier, Gaussian mixture model (GMM), Support Vector Machine (SVM) classifier, nearest centroid classifier, linear regression classifier and random forest classifier; whereby the relative abundance of SEQ ID NOs: 1-48 in said sample in comparison to said reference abundance allows the identification of said tissue of origin of said sample; and
   (d) identifying the tissue of origin of said sample based on said relative abundance of SEQ ID NOs: 1-48 in said sample.

4. The method of claim 3, wherein said cancer is selected from the group consisting of liver cancer, biliary tract cancer, lung cancer, bladder cancer, prostate cancer, breast cancer, colon cancer, ovarian cancer, testicular cancer, stomach cancer, thyroid cancer, pancreas cancer, brain cancer, head and neck cancer, kidney cancer, melanoma, thymus cancer and esophagus cancer.

5. The method of claim 4, wherein said testicular cancer is selected from the group consisting of testicular non-seminoma and testicular seminoma.

6. The method of claim 4, wherein said lung cancer is selected from the group consisting of lung carcinoid, lung small cell carcinoma, lung adenocarcinoma and lung squamous cell carcinoma.

7. The method of claim 4, wherein said ovarian cancer is selected from the group consisting of ovarian serous and ovarian endometrioid cancer.

8. The method of claim 4, wherein said brain cancer is selected from the group consisting of brain astrocytoma and brain oligodendroglioma.

9. The method of claim 4, wherein said thyroid cancer is selected from the group consisting of thyroid papillary, thyroid follicular and thyroid medullary cancer.

10. The method of any of claim 1 or 3, wherein said biological sample is selected from the group consisting of bodily fluid, a cell line, a tissue sample, a biopsy sample, a needle biopsy sample, a fine needle biopsy (FNA) sample, a surgically removed sample, and a sample obtained by tissue-sampling procedures such as endoscopy, bronchoscopy, or laparoscopic methods.

11. The method of claim 10, wherein said tissue is a fresh, frozen, fixed, wax-embedded or formalin-fixed paraffin-embedded (FFPE) tissue.

12. The method of claim 3 wherein the relative abundance of SEQ ID NOS: 6, 9, 25, and 26 in said sample is indicative of a cancer of liver origin.

13. The method of claim 3 wherein the relative abundance of SEQ ID NOS: 6, 26, and 41 in said sample is indicative of a cancer of testicular origin.

14. The method of claim 3 wherein the relative abundance of SEQ ID NOS: 6, 26, 31, 41, 45, and 48 in said sample is indicative of a cancer of testicular seminoma origin.

15. The method of claim 3 wherein the relative abundance of SEQ ID NOS: 6, 15, 17, 26, 41, and 46 in said sample is indicative of a cancer of melanoma origin.

16. The method of claim 3 wherein the relative abundance of SEQ ID NOS: 6, 7, 15, 17, 26, 41, 46, and 47 in said sample is indicative of a cancer of kidney origin.

17. The method of claim 3 wherein the relative abundance of SEQ ID NOS: 6, 7, 15, 17, 26, 41, 46, and 47 in said sample is indicative of a cancer of brain origin.

18. The method of claim 3 wherein the relative abundance of SEQ ID NOS: 6, 7, 10, 15, 17, 26, 41, 46, and 47 in said sample is indicative of a cancer of brain astrocytoma origin.

19. The method of claim 3 wherein the relative abundance of SEQ ID NOS: 6, 17-19, 24, 26, 32, 41 in said sample is indicative of a cancer of thyroid medullary origin.

20. The method of claim 3 wherein the relative abundance of SEQ ID NOS: 3, 6, 17-19, 24, 26, 32, 36, 41, and 42 in said sample is indicative of a cancer of lung carcinoid origin.

21. The method of claim 3 wherein the relative abundance of SEQ ID NOS: 3, 6, 17-19, 24, 26, 32, 36, 41, and 42 in said sample is indicative of a cancer of lung small cell carcinoma origin.

22. The method of claim 3 wherein the relative abundance of SEQ ID NOS: 1, 3, 4, 6, 17-19, 21, 26, 29, 34, 37, 41, 42, and 48 in said sample is indicative of a cancer of colon origin.

23. The method of claim 3 wherein the relative abundance of SEQ ID NOS: 1, 3, 4, 6, 17-19, 21, 26, 29, 34, 37, 41, 42, and 48 in said sample is indicative of a cancer of stomach origin.

24. The method of claim 3 wherein the relative abundance of SEQ ID NOS: 1, 3, 6, 17-19, 21, 26, 28, 29, 33, 37, 41, and 42 in said sample is indicative of a cancer of pancreas origin.

25. The method of claim 3 wherein the relative abundance of SEQ ID NOS: 1, 3, 6, 9, 17-19, 21, 25, 26, 28, 29, 33, 37, 41, and 42 in said sample is indicative of a cancer of biliary tract origin.

26. The method of claim 3 wherein the relative abundance of SEQ ID NOS: 3, 6, 17-21, 26, 41, and 42 in said sample is indicative of a cancer of prostate origin.

27. The method of claim 3 wherein the relative abundance of SEQ ID NOS: 3, 5, 6, 11, 17-21, 26, 30, 41, and 42 in said sample is indicative of a cancer of ovarian origin.

28. The method of claim 3 wherein the relative abundance of SEQ ID NOS: 2, 3, 5, 6, 11, 17-22, 26, 30, 41, and 42 in said sample is indicative of a cancer of ovarian endometrioid origin.

29. The method of claim 3 wherein the relative abundance of SEQ ID NOS: 3, 5, 6, 11, 17-22, 26, 30, 39, 41, and 42 in said sample is indicative of a cancer of breast origin.

30. The method of claim 3 wherein the relative abundance of SEQ ID NOS: 3, 5, 6, 8, 11, 16-22, 26, 27, 30, 37, 39, 41, and 42 in said sample is indicative of a cancer of lung adenocarcinoma origin.

31. The method of claim 3 wherein the relative abundance of SEQ ID NOS: 3, 5, 6, 8, 11, 16-22, 26, 27, 29, 30, 37-39, 41, and 42 in said sample is indicative of a cancer of papillary thyroid origin.

32. The method of claim 3 wherein the relative abundance of SEQ ID NOS: 3, 5, 6, 8, 11, 16-22, 26, 27, 29, 30, 37-39, 41, and 42 in said sample is indicative of a cancer of follicular thyroid origin.

33. The method of claim 3 wherein the relative abundance of SEQ ID NOS: 3, 5, 6, 11, 16-22, 26, 27, 29, 30, 35, 39, 41, and 42 in said sample is indicative of a cancer of thymus origin.

34. The method of claim 3 wherein the relative abundance of SEQ ID NOS: 3-6, 11, 16-22, 26, 27, 29, 30, 35, 39, 41, 42, and 44 in said sample is indicative of a cancer of bladder origin.

35. The method of claim 3 wherein the relative abundance of SEQ ID NOS: 3-6, 11, 16-23, 26, 27, 29, 30, 32, 35, 39, 41, 42, and 44 in said sample is indicative of a cancer of lung squamous origin.

36. The method of claim 3 wherein the relative abundance of SEQ ID NOS: 3-6, 11, 14, 16-23, 26, 27, 29, 30, 32, 35, 37, 39, 41, 42, 44, and 45 in said sample is indicative of a cancer of head and neck origin.

37. The method of claim 3, wherein the relative abundance of SEQ ID NOS: 3-6, 11, 14, 16-23, 26, 27, 29, 30, 32, 35, 37, 39, 41, 42, 44, and 45 in said sample is indicative of a cancer of esophagus-squamous origin.

38. The method of any of claim 1 or 3, wherein the nucleic acid sequence expression profile or relative abundance is determined by a method selected from the group consisting of nucleic acid hybridization and nucleic acid amplification.

39. The method of claim 38, wherein the nucleic acid hybridization is performed using a solid-phase nucleic acid biochip array or in situ hybridization.

40. The method of claim 38, wherein said nucleic acid amplification method is real-time PCR.

41. The method of claim 40, wherein said real-time PCR comprises forward and reverse primers.

42. The method of claim 41, wherein said forward primer comprises a sequence selected from the group consisting of SEQ ID NOS: 50-98.

43. The method of claim 41, wherein said reverse primer comprises SEQ ID NO: 288.

44. The method of any of claim 42 or 43, wherein said real-time PCR method further comprises probes.

45. The method of claim 44, wherein said probes comprise sequences that are complementary to SEQ ID NOS: 1-48.

46. The method of claim 45, wherein said probes comprise a sequence selected from the group consisting of SEQ ID NOS: 99-149.

47. A kit for identifying a tissue of origin of a cancer, said kit comprising 48 primers, each primer comprising the sequence at least 90% identical to each of SEQ ID NOS: 50-97, respectively.

48. The kit of claim 47, wherein the kit further comprises a probe comprising the sequence selected from the group consisting of SEQ ID NOS: 99-149.

49. The kit of claim 48, wherein said cancer is selected from the group consisting of liver cancer, biliary tract cancer, lung cancer, bladder cancer, prostate cancer, breast cancer, colon cancer, ovarian cancer, testicular cancer, stomach cancer, thyroid cancer, pancreas cancer, brain cancer, head and neck cancer, kidney cancer, melanoma, thymus cancer and esophagus cancer.

* * * * *